US010910087B2

(12) United States Patent
Cho et al.

(10) Patent No.: US 10,910,087 B2
(45) Date of Patent: Feb. 2, 2021

(54) SECURE SECRET-SHARING-BASED CROWDSOURCING FOR LARGE-SCALE ASSOCIATION STUDIES OF GENOMIC AND PHENOTYPIC DATA

(71) Applicants: Hyunghoon Cho, Cambridge, MA (US); Bonnie Berger Leighton, Newton, MA (US); David J. Wu, Stanford, CA (US)

(72) Inventors: Hyunghoon Cho, Cambridge, MA (US); Bonnie Berger Leighton, Newton, MA (US); David J. Wu, Stanford, CA (US)

( * ) Notice: Subject to any disclaimer, the term of this patent is extended or adjusted under 35 U.S.C. 154(b) by 0 days.

(21) Appl. No.: 16/020,058

(22) Filed: Jun. 27, 2018

(65) Prior Publication Data

US 2018/0373834 A1 Dec. 27, 2018

Related U.S. Application Data

(60) Provisional application No. 62/525,446, filed on Jun. 27, 2017.

(51) Int. Cl.
| | | |
|---|---|---|
| *G16B 20/00* | (2019.01) | |
| *G16B 30/00* | (2019.01) | |
| *G16B 50/30* | (2019.01) | |
| *G16B 5/00* | (2019.01) | |
| *G16B 25/00* | (2019.01) | |

(52) U.S. Cl.
CPC ............ *G16B 20/00* (2019.02); *G16B 30/00* (2019.02); *G16B 50/30* (2019.02); *G16B 5/00* (2019.02); *G16B 25/00* (2019.02)

(58) Field of Classification Search
None
See application file for complete search history.

(56) References Cited

U.S. PATENT DOCUMENTS

| | | |
|---|---|---|
| 9,276,911 B2 | 3/2016 | Wang et al. |
| 9,715,574 B2 | 7/2017 | Baym et al. |
| 2014/0075183 A1 | 3/2014 | Wang et al. |
| 2014/0121990 A1 | 5/2014 | Baldi et al. |

OTHER PUBLICATIONS

Kamm, Liina, et al. "A new way to protect privacy in large-scale genome-wide association studies." Bioinformatics 29.7 (2013): 886-893.*
Evangelou, Evangelos, and John PA Ioannidis. "Meta-analysis methods for genome-wide association studies and beyond." Nature Reviews Genetics 14.6 (2013): 379.*
Aliasgari, M., Blanton, M., Zhang, Y., & Steele, A. "Secure Computation on Floating Point Numbers." 18 pp. In Network and Distributed System Security Symposium (NDSS), 2013.*
Demmler, Daniel, Thomas Schneider, and Michael Zohner. "ABY-A Framework for Efficient Mixed-Protocol Secure Two-Party Computation." In Network and Distributed System Security Symposium (NDSS), 2015.*
Beaver, Donald, Silvio Micali, and Phillip Rogaway. "The round complexity of secure protocols." In ACM Symposium on Theory of Computing (STOC), vol. 90, pp. 503-513. vol. 90. 1990.*
Beaver, Donald. "Efficient multiparty protocols using circuit randomization." Annual International Cryptology Conference, pp. 420-432. Springer, Berlin, Heidelberg, 1991.*
Bogdanov, Dan, Sven Laur, and Jan Willemson. "Sharemind: A framework for fast privacy-preserving computations." In European Symposium on Research in Computer Security, pp. 192-206. Springer, Berlin, Heidelberg, 2008.*
Catrina, Octavian, and Sebastiaan De Hoogh. "Improved primitives for secure multiparty integer computation." In International Conference on Security and Cryptography for Networks, pp. 182-199. Springer, Berlin, Heidelberg, 2010.*
Choudhury, Ashish, et al. "Linear Overhead Robust MPC with Honest Majority Using Preprocessing." IACR Cryptology ePrint Archive, p. 705. 2015.*
Cramer, Ronald, Ivan Damgård, and Yuval Ishai. "Share conversion, pseudorandom secret-sharing and applications to secure computation." In Theory of Cryptography Conference, pp. 342-362. Springer, Berlin, Heidelberg, 2005.*
Demmler, D., Schneider, T., & Zohner, M. "Ad-hoc secure two-party computation on mobile devices using hardware tokens." in 23rd {USENIX} Security Symposium ({USENIX} Security 14), pp. 893-908. 2014.*
Eigner, Fabienne, et al. "Differentially private data aggregation with optimal utility." Proceedings of the 30th Annual Computer Security Applications Conference, pp. 316-325. ACM, 2014.*
Pullonen, Pille. "Actively secure two-party computation: Efficient Beaver triple generation." Master's thesis, University of Tartu, 89 pages. Instructor. 2013.*

(Continued)

*Primary Examiner* — G Steven Vanni
(74) *Attorney, Agent, or Firm* — David H. Judson

(57) ABSTRACT

Computationally-efficient techniques facilitate secure crowdsourcing of genomic and phenotypic data, e.g., for large-scale association studies. In one embodiment, a method begins by receiving, via a secret sharing protocol, genomic and phenotypic data of individual study participants. Another data set, comprising results of pre-computation over random number data, e.g., mutually independent and uniformly-distributed random numbers and results of calculations over those random numbers, is also received via secret sharing. A secure computation then is executed against the secretly-shared genomic and phenotypic data, using the secretly-shared results of the pre-computation over random number data, to generate a set of genome-wide association study (GWAS) statistics. For increased computational efficiency, at least a part of the computation is executed over dimensionality-reduced genomic data. The resulting GWAS statistics are then used to identify genetic variants that are statistically-correlated with a phenotype of interest.

8 Claims, 29 Drawing Sheets

(56) References Cited

OTHER PUBLICATIONS

Wang, Rui, et al. "Learning your identity and disease from research papers: information leaks in genome wide association study." In Proceedings of the 16th ACM conference on Computer and communications security, pp. 534-544. ACM, 2009.*

Putnam, P. P., Zhang, G., & Wilsey, P. A. A comparison study of succinct data structures for use in GWAS. BMC bioinformatics, 14(1), 369. 2013.*

Ritchie, M. D. Finding the epistasis needles in the genome-wide haystack. In Epistasis, pp. 19-33. Humana Press, New York, NY. 2015.*

Charikar, et al, "Finding frequent items in data streams," Theoretical Computer Science, 312(1), 2004.

Halko, et al, "Finding structure with randomness: probabilistic algorithms for constructing approximate matrix decompositions," SIAM Review, 53(2), 2011.

Laurie, et al, "Quality control and quality assurance in genotypic data for genome-wide association studies," Genetic Epidemiology, 34(6), 2010.

Markstein, "Software division and square root using Goldschmidt's algorithms," Proceedings of the 6th Conference on Real Numbers And Computers, vol. 123, 2004.

Wang, "Convergence of the tridiagonal QR algorithm," Linear Algebra and Its Applications, 322(103), 2001.

Price et al, "Principal components analysis corrects for stratification in genome-wide association studies," Nature Geneticss, 38(8), 2006.

* cited by examiner

FIG. 3(b)
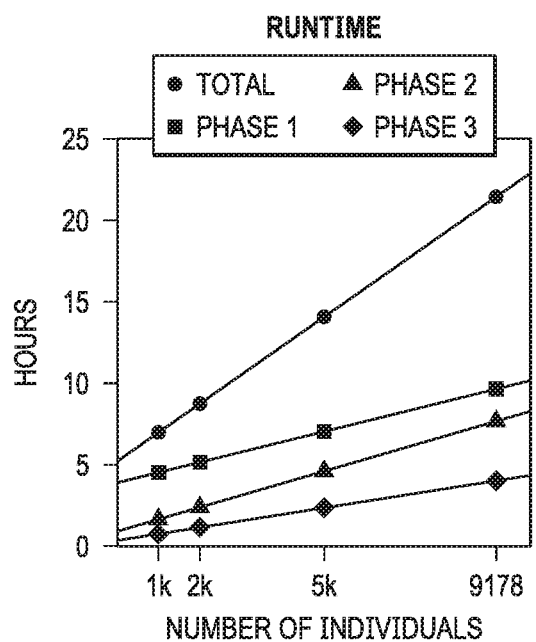
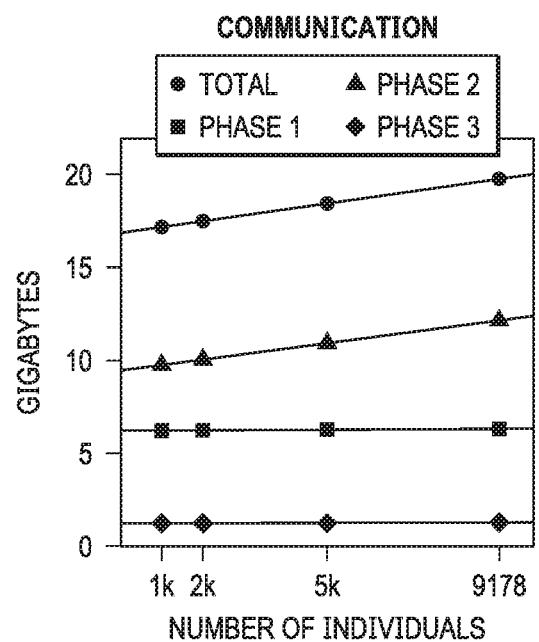
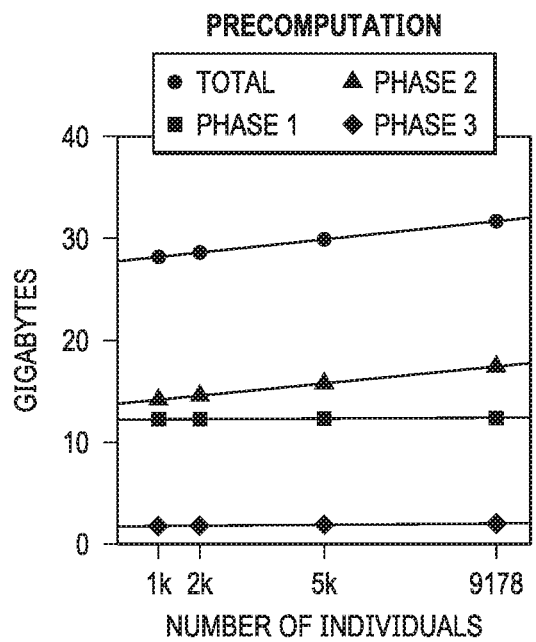
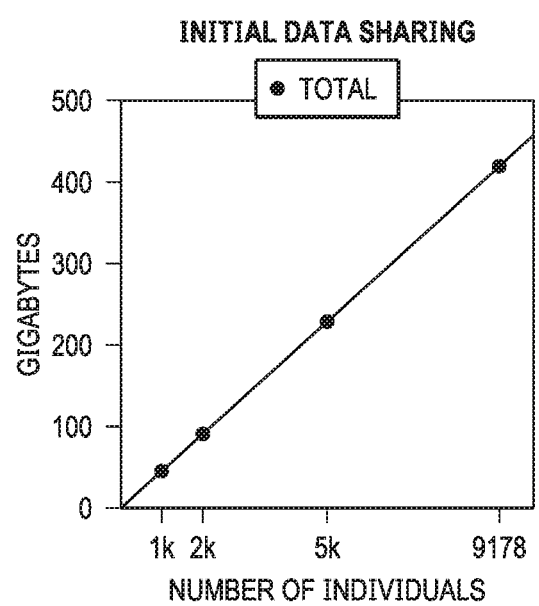

| Notation | Description |
|---|---|
| $\langle a, b, c, d \rangle$ | $CP_1$ sees $a$, $CP_2$ sees $b$, $CP_0$ sees $c$, SP sees $d$ |
| $\langle \perp, a, \perp, a \rangle$ | Both $CP_2$ and SP see $a$ |
| $\langle a, \perp, b \rangle$ | $CP_1$ sees $a$, $CP_0$ sees $b$ |
| $\langle a, b \rangle$ | $CP_1$ sees $a$, $CP_2$ sees $b$ |

Protocol 1: $[x] \leftarrow \mathsf{ShareSecret}(\langle \perp, \perp, \perp, x \rangle)$ (or $\langle \perp, \perp, x \rangle$)

1: SP (or $CP_0$): Sample a uniformly random element $r \xleftarrow{R} \mathbb{Z}_q$
2: SP (or $CP_0$): Send $r$ to $CP_1$ and $x - r$ to $CP_2$
3: return $\langle r, x - r \rangle$

---

Protocol 2: $\langle x, x \rangle \leftarrow \mathsf{ReconstructSecret}([x])$ 1: $CP_1$: Send $[x]_1$ to $CP_2$
2: $CP_2$: Send $[x]_2$ to $CP_1$
3: $CP_1, CP_2$: Compute $x \leftarrow [x]_1 + [x]_2$
4: return $\langle x, x \rangle$

Protocol 3: $[x + y] \leftarrow \mathsf{Add}([x], [y])$ (also written $[x] + [y]$)

1: return $\langle [x]_1 + [y]_1, [x]_2 + [y]_2 \rangle$

---

Protocol 4: $[x + a] \leftarrow \mathsf{AddPublic}([x], \langle a, a \rangle)$ (also written $[x] + a$ or $a + [x]$)

1: return $\langle [x]_1 + a, [x]_2 \rangle$

---

Protocol 5: $[ax] \leftarrow \mathsf{MultiplyPublic}([x], \langle a, a \rangle)$ (also written $a[x]$)

1: return $\langle a[x]_1, a[x]_2 \rangle$

FIG. 6

Protocol 6: $([a], [b], [c]) \leftarrow$ GetMultiplicationTriple()

1: $CP_0$: Sample $a, b \xleftarrow{R} \mathbb{Z}_q$ and compute $c \leftarrow ab$
2: $[a] \leftarrow$ ShareSecret($\langle \perp, \perp, a \rangle$) (in parallel with Lines 3 and 4)
3: $[b] \leftarrow$ ShareSecret($\langle \perp, \perp, b \rangle$)
4: $[c] \leftarrow$ ShareSecret($\langle \perp, \perp, c \rangle$)
5: return $([a], [b], [c])$

---

Protocol 7: $[xy] \leftarrow$ Multiply($[x], [y]$) (also written $[x][y]$)

1: $([a], [b], [c]) \leftarrow$ GetMultiplicationTriple()
2: $\langle x - a, x - a \rangle \leftarrow$ ReconstructSecret($[x] - [a]$) (in parallel with Line 3)
3: $\langle y - b, y - b \rangle \leftarrow$ ReconstructSecret($[y] - [b]$)
4: return $(x - a)(y - b) + (x - a)[b] + (y - b)[a] + [c]$

FIG. 7

Protocol 8: $\langle x-r, x-r \rangle, \langle [r]_1, [r]_2, r \rangle \leftarrow$ BeaverPartition($[x]$)

1: $CP_0$: Sample $r \xleftarrow{R} \mathbb{Z}_q$
2: $[r] \leftarrow$ ShareSecret($\langle \perp, \perp, r \rangle$)
3: $\langle x-r, x-r \rangle \leftarrow$ ReconstructSecret($[x] - [r]$)
4: return $\langle x-r, x-r \rangle, \langle [r]_1, [r]_2, r \rangle$

---

Protocol 9: $[f(x_1, \ldots, x_n)] \leftarrow$ EvaluatePolynomial($f, [x_1], \ldots, [x_n]$)

Require: $f(x_1, \ldots, x_n) = \sum_{t=1}^{T} c^{(t)} x_1^{p_1^{(t)}} \cdots x_n^{p_n^{(t)}}$ where $T$, $c^{(t)}$, and $p_i^{(t)}$ are public for all $i, t$
1: /* Step 1: Input blinding */
2: for each $i$ in $\{1, \ldots, n\}$ do (in parallel)
3:     $\langle x_i - r_i, x_i - r_i \rangle, \langle [r_i]_1, [r_i]_2, r_i \rangle \leftarrow$ BeaverPartition($[x_i]$)
4: end for
5:
6: /* Step 2: Offline computation */
7: $CP_0, CP_1, CP_2$: Rewrite $f$ according to Eq. (1) to obtain $\tilde{T}$ and $\tilde{p}_i^{(t)}$, $\forall i, t$
8: $CP_1, CP_2$: Calculate $\tilde{c}^{(t)}$ and $\tilde{d}_i$, $\forall i, t$, and $f(x_1 - r_1, \ldots, x_n - r_n)$
9: $CP_0$: Calculate $R^{(0)} \leftarrow f(r_1, \ldots, r_n)$ and $R^{(t)} \leftarrow r_1^{\tilde{p}_1^{(t)}} \cdots r_n^{\tilde{p}_n^{(t)}}$ for $t = 1, \ldots, \tilde{T}$
10:
11: /* Step 3: Output reconstruction */
12: for each $t$ in $\{0, \ldots, \tilde{T}\}$ do (in parallel)
13:     $[R^{(t)}] \leftarrow$ ShareSecret($\langle \perp, \perp, R^{(t)} \rangle$)
14: end for
15: $[y] \leftarrow f(x_1 - r_1, \ldots, x_n - r_n) + \sum_{i=1}^{n} \tilde{d}_i [r_i] + \sum_{t=1}^{\tilde{T}} \tilde{c}^{(t)} [R^{(t)}] + [R^{(0)}]$
16: return $[y]$

FIG. 8

|  | Beaver multiplication triples | Our method |
|---|---|---|
| Rounds (online) | $d$ | 1 |
| Bandwidth (online), $CP_1 \leftrightarrow CP_2$ | $2m$ | $k$ |
| Bandwidth (offline), $CP_0 \to CP_{1/2}$ | $3m$ | $k + \ell + \tilde{T}$ |

FIG. 9

|  | Multiplication triples | Our method |
|---|---|---|
| Rounds (online) | 1 | 1 |
| Bandwidth (online), $CP_1 \leftrightarrow CP_2$ | $2d_1d_2d_3$ | $d_1d_2 + d_2d_3$ |
| Bandwidth (offline), $CP_0 \to CP_{1/2}$ | $3d_1d_2d_3$ | $d_1d_2 + d_2d_3 + d_1d_3$ |

FIG. 10

|  | Beaver triples | Our method (without reuse) | Our method (with reuse) |
| --- | --- | --- | --- |
| Rounds (online) | $2T$ | $2T$ | $2T$ |
| Bandwidth (online), $CP_1 \leftrightarrow CP_2$ | $4d_3Td_1d_2$ | $2Td_1d_2 + d_3T(d_1 + d_2)$ | $d_1d_2 + d_3T(d_1 + d_2)$ |
| Bandwidth (offline), $CP_0 \to CP_{1/2}$ | $6d_3Td_1d_2$ | $2Td_1d_2 + 2d_3T(d_1 + d_2)$ | $d_1d_2 + 2d_3T(d_1 + d_2)$ |

FIG. 11

|  | Multiplication triples | Our method |
|---|---|---|
| Rounds (online) | $\alpha - 1$ | 1 |
| Bandwidth (online), $CP_1 \leftrightarrow CP_2$ | $2(\alpha - 1)$ | 1 |
| Bandwidth (offline), $CP_0 \to CP_{1/2}$ | $3(\alpha - 1)$ | $2(\alpha - 1)$ |

FIG. 12

Protocol 10: $[x^2], \ldots, [x^d] \leftarrow \mathsf{Powers}([x], d)$

Require: $d \geq 2$
1: $\langle x - r, x - r \rangle, \langle [r]_1, [r]_2, r \rangle \leftarrow \mathsf{BeaverPartition}([x])$
2: $\mathsf{CP}_0$: Calculate $r^2, \ldots, r^d \in \mathbb{Z}_q$
3: for each $t$ in $\{2, \ldots, d\}$ do (in parallel)
4: $\quad [r^t] \leftarrow \mathsf{ShareSecret}(\langle \bot, \bot, r^t \rangle)$
5: end for
6: for each $t$ in $\{2, \ldots, d\}$ do
7: $\quad [x^t] \leftarrow (x - r)^t + \sum_{i=1}^{t} \binom{t}{i} (x - r)^{t-i} [r^i]$
8: end for
9: return $[x^2], \ldots, [x^d]$

---

Protocol 11: $[T(k)] \leftarrow \mathsf{TableLookup}(T = \{k_i \mapsto v_i\}_{i=1}^{d}, [k])$

Require: $k \in \{k_1, \ldots, k_d\}, d \geq 2$
1: $c_0, \ldots, c_{d-1} \leftarrow \mathsf{LagrangeInterpolation}(T)$
2: $[k^2], \ldots, [k^{d-1}] \leftarrow \mathsf{Powers}([k], d-1)$
3: return $c_0 + c_1 [k] + \cdots + c_{d-1} [k^{d-1}]$

FIG. 13

Protocol 12: $[\vee_{i=1}^n a_i] \leftarrow$ FanInOr($\{[a_i]\}_{i=1}^n$) (based on [11])

Require: $a_i \in \{0,1\}, \forall i$
1: $[s] \leftarrow 1 + \sum_{i=1}^n [a_i]$
2: $[v] \leftarrow$ TableLookup($\{1 \to 0\} \cup \{i \to 1\}_{i=2}^{n+1}, [s]$)
3: return $[v]$

---

Protocol 13: $\{[\vee_{j=1}^i a_j]\}_{i=1}^L \leftarrow$ PrefixOr($\{[a_i]\}_{i=1}^L$) (based on [11])

Require: $a_i \in \{0,1\}, \forall i$ and assume $L = \ell^2$ for an integer $\ell$ (if not, pad with leading zeros)
1: Reshape input as a $\ell$-by-$\ell$ matrix $[A]$ where $[A_{i,j}] = [a_{(i-1)\ell+j}]$
2: for each $i$ in $\{1, \ldots, \ell\}$ do (in parallel)
3: $\quad [x_i] \leftarrow$ FanInOr($\{[A_{i,t}]\}_{t=1}^\ell$)
4: end for
5: for each $i$ in $\{1, \ldots, \ell\}$ do (in parallel)
6: $\quad [y_i] \leftarrow$ FanInOr($\{[x_t]\}_{t=1}^i$)
7: end for
8: $[f_1] \leftarrow [x_1]$
9: for each $i$ in $\{2, \ldots, \ell\}$ do
10: $\quad [f_i] \leftarrow [y_i] - [y_{i-1}]$
11: end for
12: for each $j$ in $\{1, \ldots, \ell\}$ do (in parallel)
13: $\quad [c_j] \leftarrow \sum_{i=1}^\ell [f_i][A_{i,j}]$
14: end for
15: for each $j$ in $\{1, \ldots, \ell\}$ do (in parallel)
16: $\quad [d_j] \leftarrow$ FanInOr($\{[c_t]\}_{t=1}^j$)
17: end for
18: for each $(i,j)$ in $\{1, \ldots, \ell\}^2$ do (in parallel)
19: $\quad [b_{(i-1)\ell+j}] \leftarrow [f_i][d_j] + [y_i] - [f_i]$
20: end for
21: return $\{[b_i]\}_{i=1}^L$

FIG. 14

Protocol 14: $[a <_? b] \leftarrow$ BinaryLessThan($\{[a_i]\}_{i=1}^{L}, \{[b_i]\}_{i=1}^{L}$) (based on [11])

Require: $a_i, b_i \in \{0,1\}, \forall i$, and index starts from the most significant bit
1: for each $i$ in $\{1, \ldots, L\}$ do (in parallel)
2: $\quad [a_i \oplus b_i] \leftarrow [a_i] - 2[a_i][b_i] + [b_i]$
3: end for
4: $\{[f_i]\}_{i=1}^{L} \leftarrow$ PrefixOr($\{[a_i \oplus b_i]\}_{i=1}^{L}$)
5: $[c] \leftarrow [b_1][f_1] + \sum_{i=2}^{L}[b_i]([f_i] - [f_{i-1}])$
6: return $[c]$

---

Protocol 15: $[a <_? b] \leftarrow$ BinaryLessThanPublic($\{[a_i]\}_{i=1}^{L}, \{\langle b_i, b_i \rangle\}_{i=1}^{L}$)

Require: $a_i, b_i \in \{0,1\}, \forall i$, and index starts from the most significant bit
1: for each $i$ in $\{1, \ldots, L\}$ do
2: $\quad [a_i \oplus b_i] \leftarrow [a_i] - 2b_i[a_i] + b_i$
3: end for
4: $\{[f_i]\}_{i=1}^{L} \leftarrow$ PrefixOr($\{[a_i \oplus b_i]\}_{i=1}^{L}$)
5: $[c] \leftarrow b_1[f_1] + \sum_{i=2}^{L} b_i([f_i] - [f_{i-1}])$
6: return $[c]$

FIG. 15

Protocol 16: $[x_{\text{trunc}}] \leftarrow \text{Truncate}([x], b, s)$

Require: Number of bits to mask $b$, number of least significant bits to truncate $s$, and a statistical security parameter $\kappa$ 1: $CP_0$: Sample $r \xleftarrow{R} \{0, \ldots, 2^{b+\kappa} - 1\}$
2: $CP_0$: Calculate $r_{\text{tail}} \leftarrow r \mod 2^s$
3: $[r] \leftarrow \text{ShareSecret}(\langle \bot, \bot, r \rangle)$ (in parallel with Line 4)
4: $[r_{\text{tail}}] \leftarrow \text{ShareSecret}(\langle \bot, \bot, r_{\text{tail}} \rangle)$
5: $\langle x + r, x + r \rangle \leftarrow \text{ReconstructSecret}([x] + [r])$
6: $CP_1, CP_2$: Calculate $(x + r)_{\text{tail}} \leftarrow x + r \mod 2^s$
7: return $(2^s)^{-1} \cdot ([x] + [r_{\text{tail}}] - (x + r)_{\text{tail}})$, where $(2^s)^{-1}$ denotes the inverse of $2^s$ in $\mathbb{Z}_q$

---

Protocol 17: $[xy]^{(f)} \leftarrow \text{MultiplyFP}([x]^{(f)}, [y]^{(f)})$ 1: $[z]^{(2f)} \leftarrow [x]^{(f)}[y]^{(f)}$
2: $[w]^{(f)} \leftarrow \text{Truncate}([z]^{(2f)}, k + f, f)$
3: return $[w]^{(f)}$

FIG. 16

Protocol 18: $[v] \leftarrow \text{TableLookupWithFieldConversion}(T = \{k_i \mapsto v_i\}_{i=1}^d, [[k]])$

Require: $k \in \{k_1, \ldots, k_d\}$, $d \geq 2$, $[[x]]$ secret-shared in $\mathbb{Z}_{q'}$ with $q' \ll q$
1: $T' \leftarrow T \cup \{(k_i + q') \mapsto v_i : (k_i \mapsto v_i) \in T\}$
2: $[k'] \leftarrow \langle [[k]]_1, [[k]]_2 \rangle$
3: $[v] \leftarrow \text{TableLookup}(T', [k'])$
4: return $[v]$

---

Protocol 19: $[x >_? 0] \leftarrow \text{IsPositive}([x]^{(f)})$ (based on [15])

Require: Base prime of main field $q$, base prime of auxiliary field $q_2$
1: $L \leftarrow \text{BitLength}(q)$
2: $\text{CP}_0$: Sample $r \xleftarrow{R} \mathbb{Z}_q$
3: $\text{CP}_0$: Calculate $\{a_i\}_{i=1}^L \leftarrow \text{BinaryRepresentation}(r, L)$
4: $[r] \leftarrow \text{ShareSecret}(\langle \perp, \perp, r \rangle)$
5: for each $i$ in $\{1, \ldots, L\}$ do (in parallel, including Line 4)
6:     $[[a_i]] \leftarrow \text{ShareSecretSmallField}(\langle \perp, \perp, a_i \rangle, q_2)$
7: end for
8: $\langle 2 \cdot E_f(x) + r, 2 \cdot E_f(x) + r \rangle \leftarrow \text{ReconstructSecret}(2[x]^{(f)} + [r])$
9: $\text{CP}_{1,2}$: Calculate $\{b_i\}_{i=1}^L \leftarrow \text{BinaryRepresentation}(2E_f(x) + r, L)$
10: $[[a <_? b]] \leftarrow \text{BinaryLessThanPublic}(\{[[a_i]]\}_{i=1}^L, \{\langle b_i, b_i \rangle\}_{i=1}^L)$
11: $[[a_L \oplus b_L]] \leftarrow [[a_L]] - 2b_L[[a_L]] + b_L$
12: $[[u]] \leftarrow [[a_L \oplus b_L]] \cdot [[a <_? b]]$
13: $[s] \leftarrow \text{TableLookupWithFieldConversion}(\{1 \to 1, 2 \to 0\}, [[u]] + 1)$
14: return $[s]$

FIG. 17

Protocol 20: $[x <_? y] \leftarrow \text{LessThan}([x]^{(f)}, [y]^{(f)})$

Require: $x$ and $y$ have the same sign
1: $[c] \leftarrow \text{IsPositive}([x]^{(f)} - [y]^{(f)})$
2: return $1 - [c]$

---

Protocol 21: $[x <_? y] \leftarrow \text{LessThanPublic}([x]^{(f)}, \langle y, y \rangle)$

Require: $x$ and $y$ have the same sign, $y \in \mathcal{D}$
1: $[c] \leftarrow \text{IsPositive}([x]^{(f)} - E_f(y))$
2: return $1 - [c]$

FIG. 18

Protocol 22: $[2^{2t}], [2^t] \leftarrow$ NormalizerEvenExponent($[x]$) (adapts the bit-length protocol of [17])

Require: Data range $|x| < 2^{k-f-1}$ for even $k$, statistical security parameter $\kappa$, base prime of auxiliary field $q_1$ 1: $CP_0$: Sample a random element $r \xleftarrow{R} \{0, \ldots, 2^{k+\kappa} - 1\}$
2: $CP_0$: $\{r_i\}_{i=1}^{k} \leftarrow$ BinaryRepresentation($r, k$)
3: $[r] \leftarrow$ ShareSecret($\langle \perp, \perp, r \rangle$)
4: for each $i$ in $\{1, \ldots, k\}$ do (in parallel, including Line 3)
5:     $[[r_i]] \leftarrow$ ShareSecretSmallField($\langle \perp, \perp, r_i \rangle, q_1$)
6: end for
7: $\langle x + r, x + r \rangle \leftarrow$ ReconstructSecret($[x] + [r]$)
8: $CP_{1,2}$: $\{z_i\}_{i=1}^{k} \leftarrow$ BinaryRepresentation($x + r, k$)
9: $[[c]] \leftarrow$ BinaryLessThanPublic($\{[[r_i]]\}_{i=1}^{k}, \{\langle z_i, z_i \rangle\}_{i=1}^{k}$)
10: $[[z'_1]] \leftarrow 1 - [[c]]$
11: for each $i$ in $\{2, \ldots, k+1\}$ do
12:     $[[z'_i]] \leftarrow [[r_{i-1}]] - 2z_{i-1}[[r_{i-1}]] + z_{i-1}$
13: end for
14: $\{[[Z_i]]\}_{i=1}^{k+1} \leftarrow$ PrefixOr($\{[[z'_i]]\}_{i=1}^{k+1}$)
15: for each $i$ in $\{1, \ldots, k\}$ do
16:     $[[t_i]] \leftarrow [[Z_i]] - (1 - z_i)[[r_i]]$
17: end for
18: $\{[[T_i]]\}_{i=1}^{k} \leftarrow$ PrefixOr($\{[[t_i]]\}_{i=1}^{k}$)
19: $[[f_i]] \leftarrow z_i[[T_i]]$
20: $[[g_i]] \leftarrow [[r_i]] \cdot [[T_i]]$
21: $[[w]] \leftarrow$ BinaryLessThan($\{[[f_i]]\}_{i=1}^{k}, \{[[g_i]]\}_{i=1}^{k}$)
22: $[[b_{\text{odd}}]] \leftarrow \sum_{i=1}^{k/2}(1 - [[T_{2i}]])$
23: $[[b_{\text{even}}]] \leftarrow \sum_{i=1}^{k/2-1}(1 - [[T_{2i+1}]])$
24: $[[b]] \leftarrow 1 + [[w]] \cdot ([[b_{\text{odd}}]] - [[b_{\text{even}}]]) + [[b_{\text{even}}]]$
25: $[2^{2t}] \leftarrow$ TableLookupWithFieldConversion($\{i \mapsto 2^{2(i-1)}\}_{i=1}^{k/2+1}, [[b]]$)
26: $[2^t] \leftarrow$ TableLookupWithFieldConversion($\{i \mapsto 2^{i-1}\}_{i=1}^{k/2+1}, [[b]]$) (in parallel with Line 26)
27: return $[2^{2t}], [2^t]$

FIG. 19

Protocol 23: $[a/b]^{(f)} \leftarrow \text{Divide}([a]^{(f)}, [b]^{(f)})$ (based on [13])

Require: $|a|, |b| < 2^{k-f-1}$ for even $k$, $b$ strictly positive
1: $\theta \leftarrow 2\lceil \log_2(k/3.5) \rceil + 1$
2: $[2^{2t}], [2^t] \leftarrow \text{NormalizerEvenExponent}([b]^{(f)})$
3: $[\bar{b}]^{(f)} \leftarrow \text{Truncate}([2^{2t}][b]^{(f)}, k, k - f)$
4: $[\bar{b}^2]^{(f)} \leftarrow \text{MultiplyFP}([\bar{b}]^{(f)}, [\bar{b}]^{(f)})$
5: $[\bar{w}_0]^{(f)} \leftarrow E_f(5.9430) - 10[\bar{b}]^{(f)} + 5[\bar{b}^2]^{(f)}$
6: $[w_0]^{(f)} \leftarrow \text{Truncate}([2^{2t}][\bar{w}_0]^{(f)}, k + f + 2, k - f)$
7: $[x_0]^{(f)} \leftarrow \text{MultiplyFP}([a]^{(f)}, [w_0]^{(f)})$
8: $[y_0]^{(f)} \leftarrow E_f(1) - \text{MultiplyFP}([b]^{(f)}, [w_0]^{(f)})$
9: for each $t$ in $\{1, \ldots, \theta\}$ do
10: $\quad [x_t]^{(f)} \leftarrow \text{MultiplyFP}([x_{t-1}]^{(f)}, E_f(1) + [y_{t-1}]^{(f)})$
11: $\quad [y_t]^{(f)} \leftarrow \text{MultiplyFP}([y_{t-1}]^{(f)}, [y_{t-1}]^{(f)})$
12: end for
13: return $[x_\theta]^{(f)}$

---

Protocol 24: $[\sqrt{a}]^{(f)}, [1/\sqrt{a}]^{(f)} \leftarrow \text{SqrtAndSqrtInverse}([a]^{(f)})$

Require: $|a| < 2^{k-f-1}$ for even integers $k$ and $f$, $a$ strictly positive
1: $\theta \leftarrow 2\lceil \log_2(k/3.5) \rceil$
2: $[2^{2t}], [2^t] \leftarrow \text{NormalizerEvenExponent}([a]^{(f)})$
3: $[\bar{a}]^{(f)} \leftarrow \text{Truncate}([2^{2t}][a]^{(f)}, k, k - f)$
4: $[\bar{a}^2]^{(f)} \leftarrow \text{MultiplyFP}([\bar{a}]^{(f)}, [\bar{a}]^{(f)})$
5: $[\bar{w}_0]^{(f)} \leftarrow E_f(2.9581) - 4[\bar{a}]^{(f)} + 2[\bar{a}^2]^{(f)}$
6: $[w_0/2]^{(f)} \leftarrow \text{Truncate}([2^t][\bar{w}_0]^{(f)}, k/2 + f + 2, (k - f)/2 + 1)$
7: $[x_0]^{(f)} \leftarrow \text{MultiplyFP}([a]^{(f)}, 2[w_0/2]^{(f)})$
8: $[y_0]^{(f)} \leftarrow [w_0/2]^{(f)}$
9: for each $t$ in $\{1, \ldots, \theta\}$ do
10: $\quad [z_t]^{(f)} \leftarrow E_f(1.5) - \text{MultiplyFP}([x_{t-1}]^{(f)}, [y_{t-1}]^{(f)})$
11: $\quad [x_t]^{(f)} \leftarrow \text{MultiplyFP}([z_t]^{(f)}, [x_{t-1}]^{(f)})$
12: $\quad [y_t]^{(f)} \leftarrow \text{MultiplyFP}([z_t]^{(f)}, [y_{t-1}]^{(f)})$ (in parallel with Line 11)
13: end for
14: return $[x_\theta]^{(f)}, 2[y_\theta]^{(f)}$

FIG. 20

Protocol 25: $[x] \leftarrow \text{ShareSecretSharedPRG}(\langle \bot, \bot, \bot, x \rangle)$ (or $\langle \bot, \bot, x \rangle$)

1: SP (or $CP_0$): Compute $r \in \mathbb{Z}_q$ using $\text{PRG}_{SP,CP_1}$ (or $\text{PRG}_{CP_0,CP_1}$)
2: $CP_1$: Compute $r \in \mathbb{Z}_q$ using $\text{PRG}_{SP,CP_1}$ (or $\text{PRG}_{CP_0,CP_1}$)
3: SP (or $CP_0$): Send $x - r$ to $CP_2$
4: return $\langle r, x - r \rangle$

---

Protocol 26: $\langle x - r, x - r \rangle, \langle [r]_1, [r]_2, r \rangle \leftarrow \text{BeaverPartitionSharedPRG}([x])$ 1: $CP_{0,1}$: Compute $[r]_1 \in \mathbb{Z}_q$ using $\text{PRG}_{CP_0,CP_1}$
2: $CP_{0,2}$: Compute $[r]_2 \in \mathbb{Z}_q$ using $\text{PRG}_{CP_0,CP_2}$
3: $CP_0$: Calculate $r \leftarrow [r]_1 + [r]_2$
4: $\langle x - r, x - r \rangle \leftarrow \text{ReconstructSecret}([x] - [r])$
5: return $\langle x - r, x - r \rangle, \langle [r]_1, [r]_2, r \rangle$

FIG. 22

|  | Arith. circuit (FIG. 9) | Matrix mult. (FIG. 10) | Power iteration (FIG. 11) |
|---|---|---|---|
| Rounds (online) | 1 | 1 | $2T$ |
| Bandwidth (online), $CP_1 \leftrightarrow CP_2$ | $k$ | $d_1 d_2 + d_2 d_3$ | $d_1 d_2 + d_3 T(d_1 + d_2)$ |
| Bandwidth (offline), $CP_0 \to CP_{1/2}$ | $m + \tilde{T}$ | $d_1 d_3$ | $d_3 T(d_1 + d_2)$ |

FIG. 23

Protocol 27: $[v]^{(f)} \leftarrow \text{Householder}([x]^{(f)})$

Require: $x \in \mathbb{R}^d$

1: $[c] \leftarrow \text{IsPositive}([x_1]^{(f)})$
2: $[\text{sign}(x_1)] \leftarrow 2[c] - 1$
3: $[\|x\|^2]^{(f)} \leftarrow \text{Truncate}([x^T]^{(f)}[x]^{(f)}, k+f, f)$
4: $[\|x\|]^{(f)}, [1/\|x\|]^{(f)} \leftarrow \text{SqrtAndSqrtInverse}([\|x\|^2]^{(f)})$
5: $[u]^{(f)} \leftarrow [x]^{(f)} + [\text{sign}(x_1)][\|x\|]^{(f)} e_1$.
6: $[\|u\|^2]^{(f)} \leftarrow \text{Truncate}([u^T]^{(f)}[u]^{(f)}, k+f, f)$
7: $[\|u\|]^{(f)}, [1/\|u\|]^{(f)} \leftarrow \text{SqrtAndSqrtInverse}([\|u\|^2]^{(f)})$
8: $[v]^{(f)} \leftarrow \text{Truncate}([1/\|u\|]^{(f)}[u]^{(f)}, k+f, f)$.
9: return $[v]^{(f)}$

FIG. 24

Protocol 28: $[\mathbf{Q}]^{(f)}, [\mathbf{R}]^{(f)} \leftarrow \mathsf{QRFactorizeSquare}([\mathbf{A}]^{(f)})$

Require: $\mathbf{A} \in \mathbb{R}^{d \times d}$
1: $[\mathbf{Q}]^{(f)} \leftarrow \langle \mathbf{0}_{d \times d}, E_f(\mathbf{I}_{d \times d}) \rangle$, where $\mathbf{I}_{d \times d} \in \mathbb{R}^{d \times d}$ is the identity matrix of dimension $d$
2: $[\mathbf{R}]^{(f)} \leftarrow \langle \mathbf{0}_{d \times d}, \mathbf{0}_{d \times d} \rangle$
3: $[\mathbf{A}^{(1)}]^{(f)} \leftarrow [\mathbf{A}]^{(f)}$
4: for $i = 1, \ldots, d-1$ do
5:     $[\mathbf{v}]^{(f)} \leftarrow \mathsf{Householder}([\mathbf{A}_{:,1}^{(i)}]^{(f)})$
6:
7:     /* Householder-transform $\mathbf{A}^{(i)}$ and $\mathbf{Q}_{:,i:}$ */
8:     $[\mathbf{v}^T \mathbf{A}^{(i)}]^{(f)} \leftarrow \mathsf{Truncate}([\mathbf{v}^T]^{(f)}[\mathbf{A}^{(i)}]^{(f)}, k+f, f)$ (in parallel with Line 9)
9:     $[\mathbf{Q}_{:,i:}\mathbf{v}]^{(f)} \leftarrow \mathsf{Truncate}([\mathbf{Q}_{:,i:}]^{(f)}[\mathbf{v}]^{(f)}, k+f, f)$
10:     $[\mathbf{v}\mathbf{v}^T \mathbf{A}^{(i)}]^{(f)} \leftarrow \mathsf{Truncate}([\mathbf{v}]^{(f)}[\mathbf{v}^T \mathbf{A}^{(i)}]^{(f)}, k+f, f)$ (in parallel with Line 11)
11:     $[\mathbf{Q}_{:,i:}\mathbf{v}\mathbf{v}^T]^{(f)} \leftarrow \mathsf{Truncate}([\mathbf{Q}_{:,i:}\mathbf{v}]^{(f)}[\mathbf{v}^T]^{(f)}, k+f, f)$
12:     $[\mathbf{A}^{(i)}]^{(f)} \leftarrow [\mathbf{A}^{(i)}]^{(f)} - 2[\mathbf{v}\mathbf{v}^T \mathbf{A}^{(i)}]^{(f)}$
13:     $[\mathbf{Q}_{:,i:}]^{(f)} \leftarrow [\mathbf{Q}_{:,i:}]^{(f)} - 2[\mathbf{Q}_{:,i:}\mathbf{v}\mathbf{v}^T]^{(f)}$
14:
15:     $[\mathbf{R}_{i,i:}]^{(f)} \leftarrow [\mathbf{A}_{1,:}^{(i)}]^{(f)}$
16:     $[\mathbf{A}^{(i+1)}]^{(f)} \leftarrow [\mathbf{A}_{2:,2:}^{(i)}]^{(f)}$
17: end for
18: $[\mathbf{R}_{d,d}]^{(f)} \leftarrow [\mathbf{A}_{1,1}^{(d)}]^{(f)}$
19: return $[\mathbf{Q}]^{(f)}$ and $[\mathbf{R}]^{(f)}$

FIG. 25

Protocol 29: $[\mathbf{Q}]^{(f)}, [\mathbf{R}]^{(f)} \leftarrow$ QRFactorizeRectangle($[\mathbf{A}]^{(f)}$)

Require: $\mathbf{A} \in \mathbb{R}^{d \times r}$ where $r \ll d$, and $d \times d$ matrix is too large to fit in memory 1: $[\mathbf{R}]^{(f)} \leftarrow \langle \mathbf{0}_{r \times r}, \mathbf{0}_{r \times r} \rangle$
2: $[\mathbf{A}^{(1)}]^{(f)} \leftarrow [\mathbf{A}]^{(f)}$
3: for $i = 1, \ldots, r$ do
4: $\quad [\mathbf{v}^{(i)}]^{(f)} \leftarrow$ Householder($[\mathbf{A}^{(i)}_{:,1}]^{(f)}$)
5:
6: $\quad$ /* Householder-transform $\mathbf{A}^{(i)}$ */
7: $\quad [(\mathbf{v}^{(i)})^T A^{(i)}]^{(f)} \leftarrow$ Truncate($[(\mathbf{v}^{(i)})^T]^{(f)}[\mathbf{A}^{(i)}]^{(f)}, k+f, f$)
8: $\quad [\mathbf{v}^{(i)}(\mathbf{v}^{(i)})^T \mathbf{A}^{(i)}]^{(f)} \leftarrow$ Truncate($[\mathbf{v}^{(i)}]^{(f)}[(\mathbf{v}^{(i)})^T \mathbf{A}^{(i)}]^{(f)}, k+f, f$)
9: $\quad [\mathbf{A}^{(i)}]^{(f)} \leftarrow [\mathbf{A}^{(i)}]^{(f)} - 2[\mathbf{v}\mathbf{v}^T \mathbf{A}^{(i)}]^{(f)}$
10:
11: $\quad [\mathbf{R}_{i,i:}]^{(f)} \leftarrow [\mathbf{A}^{(i)}_{1,:}]^{(f)}$
12: $\quad [\mathbf{A}^{(i+1)}]^{(f)} \leftarrow [\mathbf{A}^{(i)}_{2:,2:}]^{(f)}$
13: end for
14: $[\mathbf{Q}]^{(f)} \leftarrow \langle \mathbf{0}_{d \times r}, E_f(\mathbf{I}_{d \times r}) \rangle$
15: for $i = r, \ldots, 1$ do
16: $\quad$ /* Householder-transform $\mathbf{Q}_{i:,:}$ */
17: $\quad [(\mathbf{v}^{(i)})^T \mathbf{Q}_{i:,:}]^{(f)} \leftarrow$ Truncate($[(\mathbf{v}^{(i)})^T]^{(f)}[\mathbf{Q}_{i:,:}]^{(f)}, k+f, f$)
18: $\quad [\mathbf{v}^{(i)}(\mathbf{v}^{(i)})^T \mathbf{Q}_{i:,:}]^{(f)} \leftarrow$ Truncate($[\mathbf{v}^{(i)}]^{(f)}[(\mathbf{v}^{(i)})^T \mathbf{Q}_{i:,:}]^{(f)}, k+f, f$)
19: $\quad [\mathbf{Q}_{i:,:}]^{(f)} \leftarrow [\mathbf{Q}_{i:,:}]^{(f)} - 2[\mathbf{v}\mathbf{v}^T \mathbf{Q}_{i:,:}]^{(f)}$
20: end for
21: return $[\mathbf{Q}]^{(f)}, [\mathbf{R}]^{(f)}$

FIG. 26

Protocol 30: $[\mathbf{Q}]^{(f)}, [\mathbf{T}]^{(f)} \leftarrow$ Tridiagonalize$([\mathbf{A}]^{(f)})$ (based on [33])

Require: $\mathbf{A} \in \mathbb{R}^{d \times d}$ symmetric

1: $[\mathbf{Q}]^{(f)} \leftarrow \langle \mathbf{0}_{d \times d}, E_f(\mathbf{I}_{d \times d}) \rangle$
2: $[\mathbf{T}]^{(f)} \leftarrow \langle \mathbf{0}_{d \times d}, \mathbf{0}_{d \times d} \rangle$
3: $[\mathbf{A}^{(1)}]^{(f)} \leftarrow [\mathbf{A}]^{(f)}$
4: for $i = 1, \ldots, d-2$ do
5:    $[\mathbf{v}]^{(f)} \leftarrow$ Householder$([\mathbf{A}^{(i)}_{2:,1}]^{(f)})$
6:    $[\mathbf{vv}^T]^{(f)} \leftarrow$ Truncate$([\mathbf{v}]^{(f)}[\mathbf{v}^T]^{(f)}, k+f, f)$
7:    $[\mathbf{P}]^{(f)} \leftarrow \begin{bmatrix} \langle 0,1 \rangle & \langle 0,0 \rangle \\ \langle 0,0 \rangle & \mathbf{I}_{(d-i) \times (d-i)} - 2[\mathbf{vv}^T]^{(f)} \end{bmatrix}$
8:    $[\mathbf{PA}^{(i)}]^{(f)} \leftarrow$ Truncate$([\mathbf{P}]^{(f)}[\mathbf{A}^{(i)}]^{(f)}, k+f, f)$ (in parallel with Line 9)
9:    $[\mathbf{PQ}_{i:,:}]^{(f)} \leftarrow$ Truncate$([\mathbf{P}]^{(f)}[\mathbf{Q}_{i:,:}]^{(f)}, k+f, f)$
10:   $[\mathbf{PA}^{(i)}\mathbf{P}^T]^{(f)} \leftarrow$ Truncate$([\mathbf{PA}^{(i)}]^{(f)}[\mathbf{P}^T]^{(f)}, k+f, f)$
11:   $[\mathbf{A}^{(i)}]^{(f)} \leftarrow [\mathbf{PA}^{(i)}\mathbf{P}^T]^{(f)}$
12:   $[\mathbf{Q}_{i:,:}]^{(f)} \leftarrow [\mathbf{PQ}_{i:,:}]^{(f)}$
13:   $[\mathbf{T}_{i,i}]^{(f)} \leftarrow [\mathbf{A}^{(i)}_{1,1}]^{(f)}$, $[\mathbf{T}_{i,i+1}]^{(f)} \leftarrow [\mathbf{A}^{(i)}_{1,2}]^{(f)}$, and $[\mathbf{T}_{i+1,i}]^{(f)} \leftarrow [\mathbf{A}^{(i)}_{2,1}]^{(f)}$
14:   $[\mathbf{A}^{(i+1)}]^{(f)} \leftarrow [\mathbf{A}^{(i)}_{2:,2:}]^{(f)}$
15: end for
16: $[\mathbf{T}_{d-1:,d-1:}]^{(f)} \leftarrow [\mathbf{A}^{(d-1)}]^{(f)}$
17: return $[\mathbf{Q}]^{(f)}, [\mathbf{T}]^{(f)}$

FIG. 27

Protocol 31: $[\mathbf{Q}]^{(f)}, [\mathbf{L}]^{(f)} \leftarrow$ Eigendecompose($[\mathbf{A}]^{(f)}$)

Require: $A \in \mathbb{R}^{d \times d}$ symmetric, number of QR iterations per eigenvalue $\omega$
1: $[\mathbf{Q}]^{(f)}, [\mathbf{T}]^{(f)} \leftarrow$ Tridiagonalize($[A]^{(f)}$)
2: $[\mathbf{Q}]^{(f)} \leftarrow [\mathbf{Q}^T]^{(f)}$
3: $[\mathbf{L}]^{(f)} \leftarrow [\mathbf{T}]^{(f)}$
4: for $i = d \ldots 1$ do
5:    for $j = 1 \ldots \omega$ do
6:       $[\mu]^{(f)} \leftarrow [\mathbf{L}_{i,i}]^{(f)}$
7:       $[\mathbf{Q'}]^{(f)}, [\mathbf{R'}]^{(f)} \leftarrow$ QRFactorizeSquare($[\mathbf{L}_{:i,:i}]^{(f)} - [\mu]^{(f)}\mathbf{I}_{i \times i}$)
8:       $[\mathbf{R'Q'}]^{(f)} \leftarrow$ Truncate($[\mathbf{R'}]^{(f)}[Q']^{(f)}, k+f, f$)
9:       $[\mathbf{L}_{:i,:i}]^{(f)} \leftarrow [\mathbf{R'Q'}]^{(f)} + [\mu]^{(f)}\mathbf{I}_{i \times i}$
10:      $[\mathbf{Q}_{:,:i}\mathbf{Q'}]^{(f)} \leftarrow$ Truncate($[\mathbf{Q}_{:,:i}]^{(f)}[Q']^{(f)}, k+f, f$)
11:      $[\mathbf{Q}_{:,:i}]^{(f)} \leftarrow [\mathbf{Q}_{:,:i}\mathbf{Q'}]^{(f)}$
12:    end for
13: end for
14: return $[\mathbf{Q}]^{(f)}, [\mathbf{L}]^{(f)}$

FIG. 28

Protocol 32: $[\mathbf{U}_\psi]^{(f)} \leftarrow$ RandomizedPCA($[\mathbf{A}]^{(f)}, \psi$)

Require: $\mathbf{A} \in \mathbb{R}^{n \times m}$, number of top principal components (of columns in $A$) to output $\psi$, oversampling parameter $\alpha$, number of power iterations $\rho$ 1: /\* Random projection \*/
2: $CP_0, CP_1, CP_2$: Sample a $(\psi + \alpha) \times n$ random sketch matrix $\Pi$ from $PRG_{CP_0, CP_1, CP_2}$
3: $[\mathbf{\Pi A}]^{(f)} \leftarrow \Pi[A]^{(f)}$
4:
5: /\* Power iteration \*/
6: for $i = 1, \ldots, \rho$ do
7: $\quad [\mathbf{\Pi A}(\mathbf{A}^T\mathbf{A})^{i-1}\mathbf{A}^T]^{(f)} \leftarrow$ Truncate($[\mathbf{\Pi A}(\mathbf{A}^T\mathbf{A})^{i-1}]^{(f)}[\mathbf{A}^T]^{(f)}, k+f, f$)
8: $\quad [\mathbf{\Pi A}(\mathbf{A}^T\mathbf{A})^i]^{(f)} \leftarrow$ Truncate($[\mathbf{\Pi A}(\mathbf{A}^T\mathbf{A})^{i-1}\mathbf{A}^T]^{(f)}[\mathbf{A}]^{(f)}, k+f, f$)
9: end for
10: $[\mathbf{Y}]^{(f)} \leftarrow [\mathbf{\Pi} A(A^T A)^\rho]^{(f)}$
11:
12: /\* Dimensionality reduction \*/
13: $[\mathbf{Q}]^{(f)}, [\mathbf{R}]^{(f)} \leftarrow$ QRFactorizeRectangle($[\mathbf{Y}^T]^{(f)}$)
14: $[\mathbf{Z}]^{(f)} \leftarrow$ Truncate($[\mathbf{A}]^{(f)}[\mathbf{Q}]^{(f)}, k+f, f$)
15: $[\mathbf{Z}^T\mathbf{Z}]^{(f)} \leftarrow$ Truncate($[\mathbf{Z}^T]^{(f)}[\mathbf{Z}]^{(f)}, k+f, f$)
16:
17: /\* Eigendecomposition of reduced matrix \*/
18: $[\mathbf{Q'}]^{(f)}, [L']^{(f)} \leftarrow$ Eigendecompose($[\mathbf{Z}^T\mathbf{Z}]^{(f)}$)
19: $[\mathbf{Q'}]^{(f)} \leftarrow [\mathbf{Q'}_{:,:\psi}]^{(f)}$ and $[\mathbf{L'}]^{(f)} \leftarrow [L'_{:\psi,:\psi}]^{(f)}$
20:
21: /\* Reconstruction of principal components \*/
22: $[(\mathbf{L'})^{1/2}]^{(f)}, [(\mathbf{L'})^{-1/2}]^{(f)} \leftarrow$ SqrtAndSqrtInverse($[L']^{(f)}$) (only on diagonal elements)
23: $[\mathbf{ZQ'}]^{(f)} \leftarrow$ Truncate($[\mathbf{Z}]^{(f)}[\mathbf{Q'}]^{(f)}, k+f, f$)
24: $[\mathbf{ZQ'}(\mathbf{L'})^{-1/2}]^{(f)} \leftarrow$ Truncate($[\mathbf{ZQ'}]^{(f)}[(\mathbf{L'})^{-1/2}]^{(f)}, k+f, f$)
25: return $[\mathbf{ZQ'}(\mathbf{L'})^{-1/2}]^{(f)}$

FIG. 29

Protocol 33: $[r^2]^{(f)} \leftarrow \text{CochranArmitage}([\mathbf{X}], [\mathbf{y}], [\mathbf{U}_\psi]^{(f)}, [\mathbf{C}])$

Require: Genotype matrix $\mathbf{X} \in \{0,1,2\}^{n \times m}$, phenotype vector $\mathbf{y} \in \{0,1\}^{n \times 1}$, top $\psi$ principal components $\mathbf{U}_\psi \in \mathbb{R}^{n \times \psi}$, additional covariate matrix $\mathbf{C} \in \{0,1\}^{n \times \ell}$ 1: /* Obtain covariate subspace */
2: $[\mathbf{U}']^{(f)} \leftarrow [[\mathbf{U}]^{(f)} \quad 2^f[\mathbf{C}]] \in \mathbb{Z}_q^{n \times (\psi + \ell)}$
3: $[\mathbf{Q}]^{(f)}, [\mathbf{R}]^{(f)} \leftarrow \text{QRFactorizeRectangle}([\mathbf{U}']^{(f)})$
4:
5: /* Calculate corrected phenotypes */
6: $[\mathbf{Q}^T\mathbf{y}]^{(f)} \leftarrow [\mathbf{Q}^T]^{(f)}[\mathbf{y}]$
7: $[\mathbf{Q}\mathbf{Q}^T\mathbf{y}]^{(f)} \leftarrow \text{Truncate}([\mathbf{Q}]^{(f)}[\mathbf{Q}^T\mathbf{y}]^{(f)}, k+f, f)$
8: $[\hat{\mathbf{y}}]^{(f)} \leftarrow 2^f[\mathbf{y}] - [\mathbf{Q}\mathbf{Q}^T\mathbf{y}]^{(f)}$
9: $[\mathbf{u}]^{(f)} \leftarrow \text{Truncate}([\mathbf{Q}]^{(f)}[\mathbf{Q}^T]^{(f)}\mathbf{1}_{(\psi+\ell)}, k+f, f)$
10:
11: /* Calculate summary statistics */
12: $[\mathbf{s}^x]^{(f)} \leftarrow 2^f \mathbf{1}_{n_{qc}}^T[\mathbf{X}] - [\mathbf{u}^T]^{(f)}[\mathbf{X}]$
13: $[\mathbf{s}^{xy}]^{(f)} \leftarrow [\hat{\mathbf{y}}^T]^{(f)}[\mathbf{X}]$
14: $[\mathbf{s}^{xx}]^{(f)} \leftarrow \mathbf{1}_n^T([\mathbf{X}] \circ [\mathbf{X}])$, where $[\mathbf{X}] \circ [\mathbf{X}]$ denotes the *element-wise* product of $\mathbf{X}$ with $\mathbf{X}$
15: $[\mathbf{B}]^{(f)} \leftarrow [\mathbf{Q}^T]^{(f)}[\mathbf{X}]$
16: $[\text{diag}(\mathbf{B}^T\mathbf{B})]^{(f)} \leftarrow \text{Truncate}(\mathbf{1}_{(\psi+\ell)}^T([\mathbf{B}]^{(f)} \circ [\mathbf{B}]^{(f)}), k+f, f)$
17: $[\mathbf{s}^{xx}]^{(f)} \leftarrow [\mathbf{s}^{xx}]^{(f)} - [\text{diag}(\mathbf{B}^T\mathbf{B})]^{(f)}$
18: $[\mathbf{s}^y]^{(f)} \leftarrow [\hat{\mathbf{y}}^T]^{(f)}\mathbf{1}_n$
19: $[\mathbf{s}^{yy}]^{(f)} \leftarrow \text{Truncate}([\hat{\mathbf{y}}^T]^{(f)}[\hat{\mathbf{y}}]^{(f)}, k+f, f)$
20:
21: /* Calculate test statistics */
22: $[\bar{\mathbf{s}}^y]^{(f)} \leftarrow \text{Truncate}(E_f(\frac{1}{N})[\mathbf{s}^y]^{(f)}, k+f, f)$
23: $[\bar{\mathbf{s}}^x]^{(f)} \leftarrow \text{Truncate}(E_f(\frac{1}{N})[\mathbf{s}^x]^{(f)}, k+f, f)$
24: $[\mathbf{a}]^{(f)} \leftarrow [\mathbf{s}^{xy}]^{(f)} - N \cdot \text{Truncate}([\bar{\mathbf{s}}^x]^{(f)}[\bar{\mathbf{s}}^y]^{(f)}, k+f, f)$
25: $[\mathbf{b}_1]^{(f)} \leftarrow [\mathbf{s}^{yy}]^{(f)} - N \cdot \text{Truncate}([\bar{\mathbf{s}}^p]^{(f)}[\bar{\mathbf{s}}^y]^{(f)}, k+f, f)$
26: $[\mathbf{b}_2]^{(f)} \leftarrow [\mathbf{s}^{xx}]^{(f)} - N \cdot \text{Truncate}([\bar{\mathbf{s}}^x]^{(f)}[\bar{\mathbf{s}}^x]^{(f)}, k+f, f)$
27: $[\sqrt{\mathbf{b}_1}]^{(f)}, [1/\sqrt{\mathbf{b}_1}]^{(f)} \leftarrow \text{SqrtAndSqrtInverse}([\mathbf{b}_1]^{(f)})$ (in parallel with Line 28)
28: $[\sqrt{\mathbf{b}_2}]^{(f)}, [1/\sqrt{\mathbf{b}_2}]^{(f)} \leftarrow \text{SqrtAndSqrtInverse}([\mathbf{b}_2]^{(f)})$
29: $[1/\sqrt{\mathbf{b}}]^{(f)} \leftarrow \text{Truncate}([1/\sqrt{\mathbf{b}_1}]^{(f)}[1/\sqrt{\mathbf{b}_2}]^{(f)}, k+f, f)$
30: $[\mathbf{r}]^{(f)} \leftarrow \text{Truncate}([\mathbf{a}]^{(f)}[1/\sqrt{\mathbf{b}}]^{(f)}, k+f, f)$
31: $[\mathbf{r}^2]^{(f)} \leftarrow \text{Truncate}([\mathbf{r}]^{(f)}[\mathbf{r}]^{(f)}, k+f, f)$
32: return $[\mathbf{r}^2]^{(f)}$

FIG. 30

SECURE SECRET-SHARING-BASED CROWDSOURCING FOR LARGE-SCALE ASSOCIATION STUDIES OF GENOMIC AND PHENOTYPIC DATA

STATEMENT OF FEDERALLY SPONSORED RESEARCH OR DEVELOPMENT

This invention was in part made with government support under GM108348 awarded by Department of Health and Human Services, National Institutes of Health. The government has certain rights in the invention.

TECHNICAL FIELD

This application relates generally to data sharing and collaboration in biomedicine.

BACKGROUND

We are entering the age where everyone will have a copy of his or her own genome sequence. Allowing researchers to tap into this vast source of information would spur scientific and medical breakthroughs. Currently, however, most sequenced genomes reside in strict access-controlled repositories.

Genome-wide association studies (GWAS) aim to identify genetic variants that are statistically correlated with phenotypes of interest (e.g., disease status). Analyzing a large number of individuals in a GWAS is critical for detecting elusive causal variants that are rare or have small effect sizes. To this end, several research groups have been coordinating efforts to amass large genomic and phenotypic databases. With the advent of large centralized databases, however, comes severe privacy concerns. In an era where companies' sensitive user data are routinely leaked in bulk, a breach of genomic and clinical data is becoming increasingly probable. Adding to the concern, a leak of genomic data permanently affects the individuals whose data is released, and their descendants. Unfortunately, it is challenging to accurately assess, let alone contain, the risks associated with genomic breaches, due to our incomplete understanding of what is encoded in one's genome.

Modern cryptography offers a means to substantially reduce the likelihood of a devastating leak. In particular, secure multiparty computation (MPC) frameworks enable researchers to collaboratively perform analyses over encrypted data without having direct access to the underlying input. Because no entity is given trust to handle the raw data, the breach or corruption of a single party no longer compromises the privacy of study participants. Despite its promises, conducting GWAS via any such framework to date has not been possible, at least in part due to major technical challenges. Existing proposals either consider vastly simplified versions of the task or require overwhelming runtime or resource constraints for modern data sets with a large number of individuals. Alternative cryptographic systems for secure computation, such as homomorphic encryption, or garbled circuits, currently impose even greater computational burden and thus are not viable for large-scale GWAS.

A major computational bottleneck for secure GWAS is identifying population structure within the study cohort, which can cause spurious associations that are linked to inter-population differences rather than the phenotype of interest. A widely used procedure for accounting for such confounding is to use principal component analysis (PCA) to capture broad patterns of genetic variation in the data. The top principal components, which are thought to be representative of population-level differences among the individuals, are included as covariates in the subsequent statistical tests to correct for bias. Performing PCA on very large matrices, however, is a highly challenging task for secure computation, which to our knowledge has never been successfully addressed. This shortcoming is mainly due to the iterative nature of algorithms for PCA, which significantly increases the communication cost and the overall complexity of the computation (e.g., the multiplicative depth). In addition, PCA requires the support of fractional numbers with a relatively high precision, which adds nontrivial overhead to most MPC frameworks that are inherently based on integer operations.

BRIEF SUMMARY

This disclosure provides for enhanced computational techniques that are leveraged to facilitate secure crowdsourcing of genomic and phenotypic data, e.g., for large-scale association studies. According to one embodiment, a method for securely crowdsourcing genomic and phenotypic data for large-scale association studies involves a set of high-level operations. In particular, the method begins by receiving, via secret sharing, genomic and phenotypic data of individual study participants in a manner that preserves privacy of individual genomic and phenotypic data. Such data is a "first data set." Then, a "second data set" is received. The second data set preferably is also received via secret sharing. The second data set comprises results of pre-computation over random number data, e.g., mutually independent and uniformly-distributed random numbers and results of calculations over those random numbers. Then, a secure computation is executed against the secretly-shared genomic and phenotypic data, using the secretly-shared results of the pre-computation over random number data, to generate a set of genome-wide association study (GWAS) statistics. For increased computational efficiency, at least a part of the computation is executed over dimensionality-reduced genomic data. The resulting GWAS statistics are then used to identify genetic variants that are statistically-correlated with a phenotype of interest.

The foregoing has outlined some of the more pertinent features of the subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the subject matter and the advantages thereof, reference is now made to the following descriptions taken in conjunction with the accompanying drawings, in which:

FIG. 4 depicts a table illustrating several examples of the nomenclature describe the protocols of this disclosure;

FIG. 5 describes respective protocols for sharing a secret and reconstructing the secret;

FIG. 6 depicts a set of primitive operations for securely adding two secret-shared numbers and securely adding/multiplying a secret-shared number with a public scalar;

FIG. 7 depicts a set of primitive operations for generating a Beaver multiplication triple and securely multiplying two secret-shared numbers;

FIG. 8 depicts a set of protocols for securely evaluating an arbitrary arithmetic circuit over the secret-shared data based on the Beaver-partitioning approach;

FIG. 9 depicts a table comparing the communication complexity between the Beaver-partitioning approach and Beaver triples with respect to evaluating an arbitrary arithmetic circuit;

FIG. 10 depicts a table comparing the communication complexity between the Beaver-partitioning approach and Beaver triples for performing secure matrix multiplication;

FIG. 11 depicts a table comparing the communication complexity between the Beaver-partitioning approach and Beaver triples for the power iteration procedure;

FIG. 12 depicts a table comparing the communication complexity between the Beaver-partitioning approach and Beaver triples for securely computing the powers of a secret-shared number;

FIG. 13 depicts a protocol for computing the powers of a secret-shared number and a protocol for looking up an element in a table, in which the target index is secret-shared;

FIG. 14 depicts a set of primitive operations for computing the logical-OR of the whole or all prefixes of a secret-shared bit vector;

FIG. 15 depicts a set of secure comparison subroutines, whereby a secret-shared number is compared to another secret-shared or public number, both given as bit vectors;

FIG. 16 depicts a set of primitive operations for discarding a given number of least significant bits from a secret-shared number and securely multiplying two secret-shared fixed-point numbers;

FIG. 17 depicts a protocol for looking up a table element given a secret-shared index in the setting where the base finite field of the index is different from that of the table elements, and a protocol for testing whether a given fixed-point number is positive;

FIG. 18 depicts a set of subroutines for securely comparing a secret-shared number with a secret-shared or public number;

FIG. 19 depicts a protocol for securely finding the position of the most significant bit of a secret-shared number;

FIG. 20 depicts a set of operations for securely dividing two secret-shared fixed-point numbers and computing the square-root of a secret-shared fixed-point number;

FIG. 22 depicts a set of protocols for secret-sharing or Beaver-partitioning a private number using the shared pseudorandom number generators;

FIG. 23 describes the communication complexity of subroutines using the shared pseudorandom number generators;

FIG. 24 depicts a subroutine for securely computing the Householder reflection of a secret-shared vector;

FIG. 25 depicts a protocol for securely performing the QR-factorization of a square secret-shared matrix;

FIG. 26 depicts a protocol for securely performing the QR-factorization of a rectangular secret-shared matrix;

FIG. 27 depicts a subroutine for finding the tridiagonalization of a secret-shared matrix;

FIG. 28 depicts a protocol for securely computing the Eigen decomposition of a secret-shared matrix;

FIG. 29 depicts a protocol for securely performing randomized principal component analysis over the secret-shared genotype data; and FIG. 30 depicts a protocol for performing Cochran-Armitage association tests over the secret-shared genotype and phenotype data.

DETAILED DESCRIPTION

The technique herein provides for a secure multiparty communication protocol for GWAS that accounts for population stratification while achieving practical performance at scale. Several technical advances enable this breakthrough. First, a core multiparty computation (MPC) technique known as Beaver triples, which was initially developed for pairwise multiplications, is generalized to arbitrary arithmetic circuits. The generalized method is used to construct efficient subroutines for matrix multiplication, exponentiation, and iterative algorithms with data reuse. Second, random projection techniques are then provided to significantly reduce the complexity of a Principal Component Analysis (PCA) procedure, e.g., during a population stratification analysis.

Figure 1:
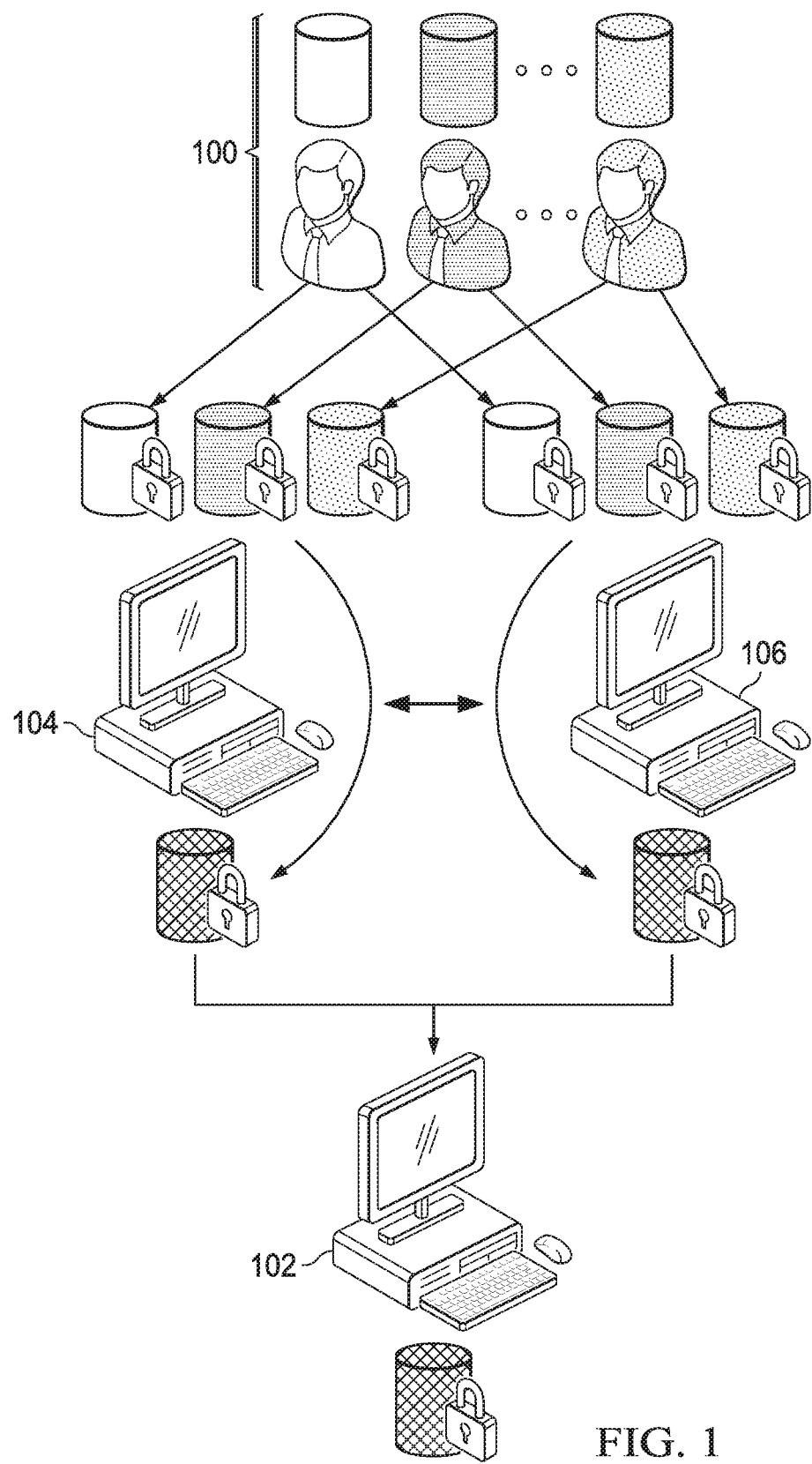
FIG. 1 is a multi-computing entity implementation environment in which the techniques of this disclosed may be practiced.

In one embodiment, the overall workflow of our MPC protocol is illustrated in FIG. 1. In addition to individuals or institutions 100 with privately-owned or controlled genomes and phenotypes (referred to as study participants [SPs]), the framework preferably involves the cooperation of at least three computing parties or entities (CP0 102, CP1 104, and CP2 106). Academic research groups, consortia, relevant government agencies (e.g., NIH), and the like, are suitable for these roles, but this is not a limitation. During the initial phase of protocol, SPs 100 share data with CP1 104 and CP2 106 in a way that enables computation, but does not reveal any information to either party 104 or 106, using a cryptographic tool called secret sharing. Next, CP1 104 and CP2 106 jointly execute an interactive protocol to perform GWAS over the private input without gaining any information about the underlying data. During this step, preferably pre-computed data from CP0 102 is used to greatly speed up the process. The information from CP0 also preferably is secretly-shared with the computing entities CP1 and CP2. Importantly, CP0 102 does not see the private input in any form and preferably is involved only during pre-processing. Lastly, CP1 104 and CP2 106 combine their results to construct final GWAS statistics. These statistics may also be published.

Figure 2:
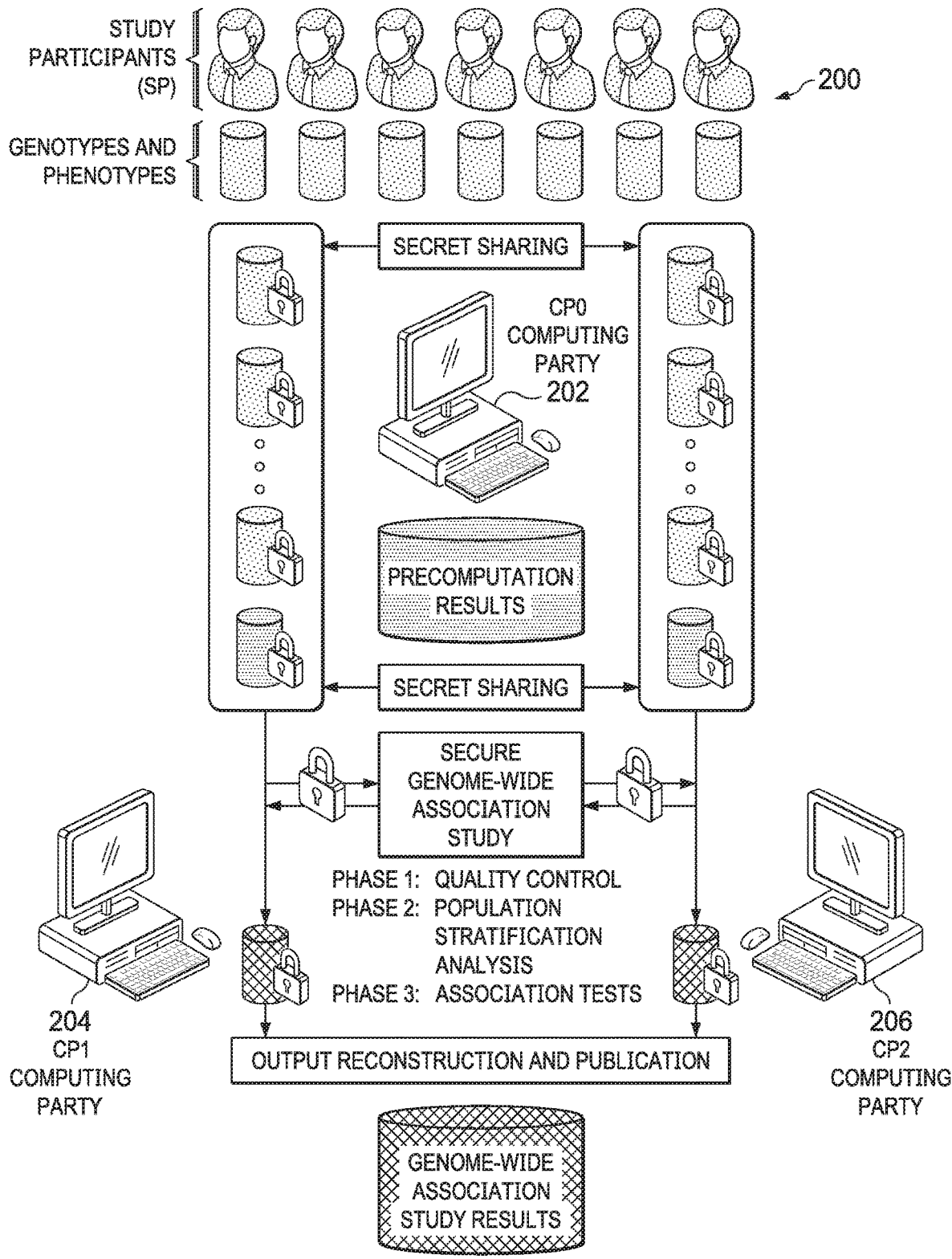
FIG. 2 depicts another view of the secure GWAS pipeline according to the techniques of this disclosure.

FIG. 2 depicts another view of the GWAS pipeline approach of this disclosure. As depicted, study participants (e.g., private individuals or institutes) 200 secretly share their genotypes and phenotypes with computing parties (e.g., research groups or government agencies), denoted CP1 204 and CP2 206, who jointly carry out the below-described secure GWAS protocol to obtain association statistics without revealing the underlying data to any party involved. An auxiliary computing party (CP0) 202 performs input-independent pre-computation to greatly speed up the main computation.

FIGS. 3(*a*) and (*b*) depicts how the technique secure GWAS protocol obtains accurate results within a practical runtime.

Figure 3A:
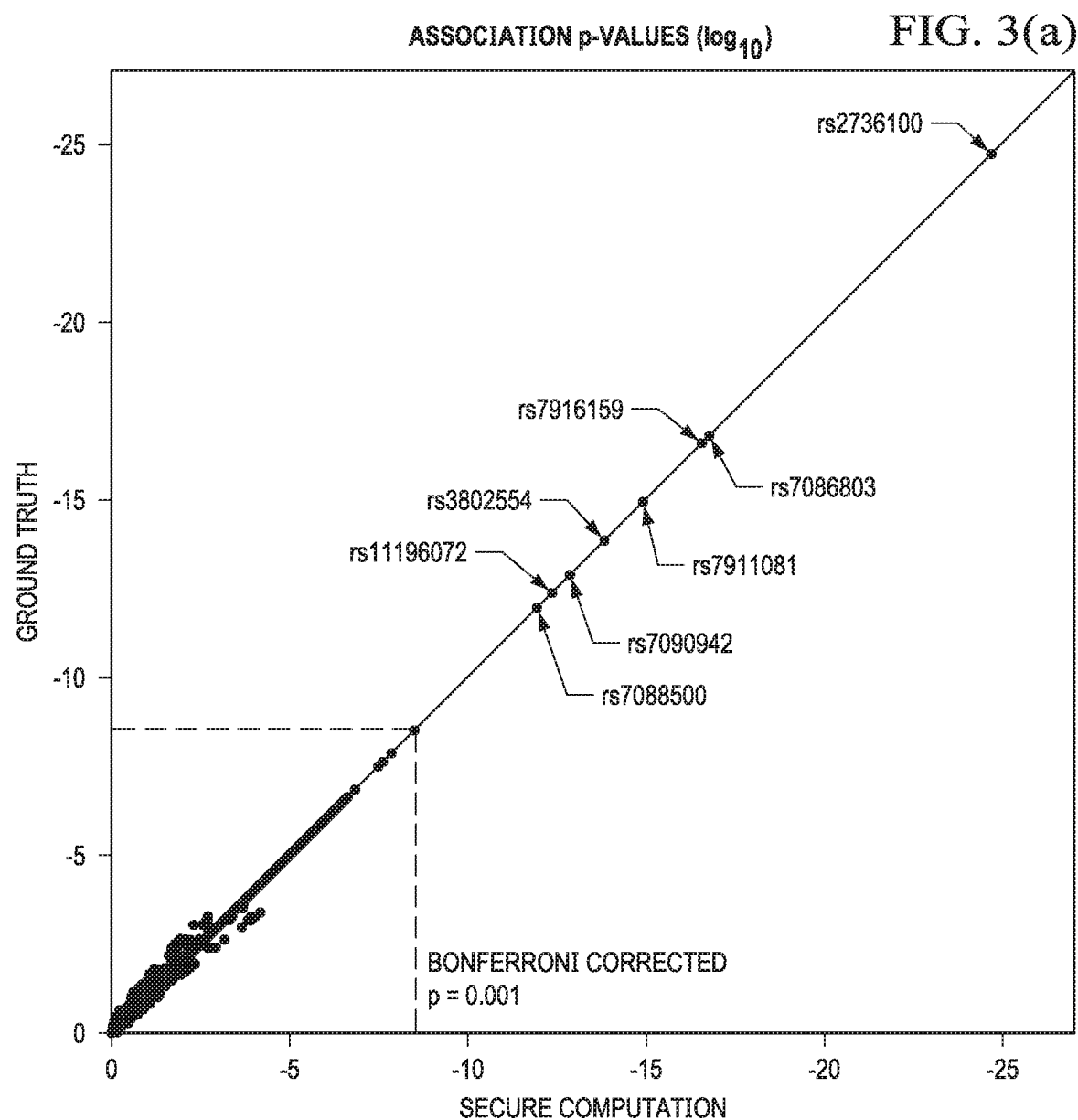
FIGS. 3(a) and (b) depict how the secure GWAS technique of this disclosure produces accurate results with a practical runtime.

The success of the MPC protocol on a real lung-cancer GWAS data set with 9,178 individuals (5,088 cases and 4,090 controls) and 612,794 genomic loci has been demonstrated. In this example, a common quality control procedure for GWAS, which includes filters for missing rate, departure from Hardy-Weinberg equilibrium, heterozygosity, and minor allele frequency, was incorporated with the MPC protocol. In addition, population bias was corrected by computing the top five principal components and including them in the association tests as covariates. As shown in FIG. 3(a), the secure MPC protocol accurately recapitulates the results obtained using the raw data. The top hits in the association tests also closely match the ones reported by the original publication, despite minor differences in the analysis. Furthermore, the approach achieved efficient runtime, communication bandwidth, and disk usage. Further, the pipeline's performance remained practical and computationally-efficient even when the number of individuals was increased to a million. These results establish that performing large-scale GWAS via secure MPC according to the techniques of this disclosure provides significant advantages.

In particular, in this example the secure GWAS protocol accurately recapitulated the ground truth association scores calculated based on the plaintext data ($r^2$=1.00; FIG. 3(a)). Moreover, the results closely matched what was presented in the original publication; the two strongest associations securely identified by the protocol, rs2736100 (p=4.76×10$^{-24}$) and rs7086803 (p=5.95×10$^{-16}$), were also the top two findings in prior work. rs2736100 maps to telomerase reverse transcriptase (TERT), whose association with lung cancer is well-established in the literature. On the other hand, rs7086803, which maps to an intracellular trafficking gene named VTI1A, was one of the three novel susceptibility loci identified by the previous study. Notably, the other two loci were originally reported with substantially weaker associations than rs7086803 and thus are likely to have been more sensitive to minor differences in the data and analysis.

In addition to obtaining accurate association statistics, the secure GWAS protocol achieved a practical runtime of one day (see FIG. 3(b)). To assess the scalability of the framework, various scalability metrics (see the discussion below titled "Methods"), which included runtime, communication bandwidth, the size of pre-computed data, and the size of initial data sharing, for subsampled data sets with varying numbers of individuals, were measured. As shown in FIG. 3(b), all metrics showed a clear linear dependence on the number of individuals in the data set. By extrapolation, the framework requires 74.6 days of computation for a data set with a million individuals. As a point of reference, the average processing time of access requests for controlled-access genomic data by NIH Data Access Committee was 80 days in 2009-2010, although this has been reduced to 14 days in 2016. Other metrics also showed reasonable and computationally-efficient scaling; for a million individuals, initial data sharing of 44.6 TB (46.8 MB data upload for each SP), a transfer of 470.3 GB of pre-computed data from CP0 to CP1 or CP2, and a communication of 346.7 GB between CP1 and CP2 during the main computation, are representative. Notably, experiments were performed with co-located servers, which enjoy communication speeds faster than in a typical real-world scenario. Even with the lower transfer rates (e.g., coast-to-coast transfer rates of 5 MB per second in United States), expected increase in runtime is at most a day.

Methods

A primary GWAS data set was obtained via dbGaP Authorized Access (study accession: phs000716.v1.p1). Retaining only autosomal SNPs, the combined data across seven study groups consisted of 612,794 genotyped loci over 9,178 individuals (5,088 cases and 4,090 controls). The study cohort was divided into five age groups: <40, 40-50, 50-60, 60-70, and >70. Binary membership vectors for age and study group were utilized as additional covariates for the association tests (ten linearly independent features). To generate smaller data sets for scalability analysis, the individuals were randomly subsampled to obtain data sets with 1 k, 2 k, and 5 k individuals.

Following the original study, the following filters were incorporated for quality control: genotype missing rate per individual <0.05 and per SNP <0.1, individual heterozygosity rate >0.25 and <0.30, minor allele frequency >0.1, and Hardy-Weinberg equilibrium test $\chi^2$ statistic <28.3740 (p-value <$10^{-7}$). All of these filters were evaluated securely without revealing the underlying data. The resulting inclusion/exclusion status for each individual and SNP is revealed to allow the CPs to reduce subsequent computation. In the experiment, the reduced data included 9,098 individuals and 378,493 loci.

For population stratification analysis, a subset of SNPs with low levels of linkage disequilibrium by imposing a pairwise distance threshold of >100 kb was used, which resulted in 23,723 loci. Genomic positions of the SNPs in the data are considered public, because it does not contain any private information. Therefore, this filtering step is performed in plaintext. Genotypes of each SNP were standardized before PCA was performed. Following previous work, this was achieved by subtracting the mean and dividing by the standard deviation of a Bernoulli variable representing an allele at the given locus being the non-reference type. This random variable is treated as being sampled twice per individual to give rise to the observed genotypes. As explained in the Supplementary Information (see below), this standardization was performed indirectly (i.e., computation results were adjusted after the fact) to avoid the size of pre-computed data being quadratic in genotype matrix dimensions. The top five principal components were then kept for the subsequent analysis.

As proof of concept, a Cochran-Armitage trend test was used to assess the association between each SNP and the disease status. In the presence of covariates, which in the example case consisted of top principal components and age/study group memberships, the desired test statistic is equivalent to the squared Pearson correlation coefficient between the genotype and phenotype vectors, where the subspace defined by the covariates are projected out from both vectors before computing the correlation. The resulting correlations were then revealed as the final output of the secure protocol. Note the mapping between test statistics and significance scores (p-values) did not reveal any additional information about the input and thus can be performed in plaintext.

To assess the scalability of the protocol, several aspects of the experiments were quantified, namely: runtime, communication bandwidth, the size of pre-computed data, and the size of initial data sharing. Runtime refers to only the main computation phase after initial data sharing, because the initial transfer is heavily dependent upon the study setup given the distributed nature of data ownership. Instead, the total size of initial data, which consists of a genotype vector, disease status, and covariate phenotypes collected from each study participant, is presented. Note that initial data sharing includes (i) distributed data transfer from each SP to CP1 or CP2 (one party receives only a few bytes for the pseudo-random generator key) and (ii) an equal-sized data exchange between CP1 and CP2 for the "Beaver partitioning" of input data (see the detailed discussion below titled "Supplementary Information").

Because the exchange between CP1 and CP2 during this procedure can be coalesced into a single batch transfer, physical shipment is a potential alternative to online data transfer at the scale of tens of terabytes corresponding to millions of genomes. Next, communication bandwidth refers to the total amount of data exchanged between CP1 and CP2 during the main computation phase. Finally, the size of pre-computed data is the amount of data transferred from CP0 to either CP1 or CP2 during the pre-computation phase.

Notably, the protocol achieves communication bandwidth (total amount of data transferred) linear in the number of individuals (n) and the number of variants (m). This excludes the initial data-sharing phase, which is necessarily quadratic due to the size of the genotype matrix. In comparison, existing frameworks lead to quadratic bandwidths with large multiplier constants, which are infeasible at scale, e.g., where both n and m are close to a million. A comprehensive description of the technical contributions, protocol details, and security and complexity analyses are provided in the Supplementary Information that follows below.

In a standard honest-but-curious security model, all parties are assumed to faithfully follow the prescribed protocol, but are free to inspect and analyze any portion of the data they observe to gain information about the input. Under this model, the described protocol guarantees that the computing parties do not learn anything about the raw genotypes or phenotypes other than what can be inferred from the final results. Notably, this security guarantee rests upon the assumption that the CPs do not collude with one another. This no-collusion assumption can be further relaxed by introducing more CPs at the expense of efficiency (see the Supplementary Information below). The protocol as described above is based on two main CPs and an auxiliary one to perform the pre-processing, but this implementation is not intended to be limiting. There may be a different number of entities in these roles, and one or more entities may have shared responsibility.

As will be described in further detail, a number of techniques that are summarized here are provided to achieve scalability. A first technique improves upon an existing building block for secure computation, known as Beaver triples. Beaver triples were originally developed for carrying out secure pairwise multiplications; according to this disclosure, they are extended to arbitrary arithmetic circuits to thereby obtain more efficient subroutines for various operations such as matrix multiplication and exponentiation. Another technique involves using a random projection-based algorithm for PCA so that the scale of the data is greatly reduced for performing population stratification correction (a known computational bottleneck of secure GWAS). An additional technique provides for the notion of shared pseudorandom number generators (PRGs) between pairs of computing entities; the use of shared PRGs obviates transferring a stream of random numbers, which is a frequent operation in the protocol, by enabling each party to independently draw the random numbers from the same PRG. Collectively, these techniques (namely, improved secure computation building blocks, randomized PCA for population stratification, and shared PRGs) enable the provision of a secure protocol that achieves practical scalability.

As will be described in more detail in the Supplementary Information that follows, the technique of this disclosure leverages building blocks that enable arbitrary arithmetic functions, i.e., addition and multiplication, over the private input, to be securely evaluated. As will be seen, the approach avoids the requirement of generating a Beaver triple for every pairwise multiplication, which is computationally-efficient especially if the overall computation contains many multiplications. As will be described, the MPC technique of this disclosure works with elements in a finite field, and there are additional high-level routines for various bit operations like bit shift, bit comparison, etc., which preferably are also written as arithmetic functions so that they can be efficiently-implemented. To address the problem (of having to generate a Beaver triple for every pairwise multiplication), the approach herein generalizes Beaver triples so that auxiliary random numbers, which enable the secure evaluation of nonlinear functions, are generated for groups of operations at a time, rather than for each individual multiplication. In particular, the generalized Beaver tuple preferably includes a random number for each input value, and some function of these random numbers for each of the output values of a desired computation. Thus, in this operation-centric to data-centric view, the total amount of auxiliary data to be generated and secret-shared depends on the size of input and output, rather than the number of pairwise multiplications, and this leads to significant computational efficiency. Although there are many ways to generate the Beaver triple, according to the protocol herein preferably a third party (CP0) is used to perform this task. As noted, the third-party preferably does not observe the input data in any way and is able to finish its task before the main protocol, as a pre-processing step.

Variants, Extensions and Applications

This work is complementary to existing literature on differential privacy techniques in biomedicine, whose aim is to control the privacy leak in the published summary statistics (i.e., association p-values), the output of a GWAS. While the amount of sensitive information revealed by the final statistics will only decrease as the size of the GWAS data sets grow, any existing method for slightly perturbing the statistics for privacy protection also can be used in conjunction with the protocol as a post-processing step.

The technical advances in achieving a scalable MPC protocol for GWAS as described herein may be extended for use with diverse applications in biomedicine and other disciplines. As an example, insights from the PCA protocol may be directly applied to drug-target interaction prediction, e.g., by casting it as a low-rank matrix factorization problem. The computational approach herein allows pharmaceutical companies and academic researchers to pool their data for more accurate predictions while keeping the raw data private. Further, the methods for secure computation as described herein removes obstacles for data sharing and, as a result, enable new workflows and opportunities for scientific collaboration.

In summary, and in the illustrative embodiment, the technique herein provides an end-to-end protocol (e.g., for secure GWAS) that provably reveals no information about input genotypes and phenotypes, except for the final association statistics.

Supplementary Information

The following Supplementary Information comprises a set of Notes that describe further technical aspects of the MPC protocol of this disclosure.

Supplementary Note 1: Protocol Setup

There are four parties in our GWAS protocol: study participants (SP), two main computing parties ($CP_1$ and $CP_2$), and an auxiliary computing party ($CP_0$). The auxiliary computing party $CP_0$ only participates in a precomputation (or preprocessing) phase of the protocol, and in particular, does not participate in the main protocol execution. For simplicity, we take SP to be a single entity that possesses all of the input genomes and phenotypes. As we discuss in Supplementary Note 9, this setting naturally generalizes to the crowdsourcing scenario where SP represents many independent participants, each securely contributing their own genome to the computing parties.

Overview.

The overall workflow of our GWAS protocol is as follows. First, using a cryptographic technique called secret sharing, the study participants SP share their data (i.e., their genome and associated phenotypes) with $CP_1$ and $CP_2$ in such a way that enables computation over the shared data, but does not reveal any information to either $CP_1$ or $CP_2$. Next, $CP_1$ and $CP_2$ engage in an interactive protocol to perform GWAS over the private inputs without learning anything about the underlying data. During this computation, $CP_1$ and $CP_2$ leverage pre-computed data from $CP_0$ (which is input-agnostic) to greatly speed up the computation. Finally, $CP_1$ and $CP_2$ combine their outputs to reconstruct the final GWAS statistics from secret shares and publish the results. We work in the general paradigm of computing on secret-shared data first formalized by Ben-Or et. al [1], and subsequently extended in a number of works [2, 3, 4, 5, 6].

Security Model.

In this paper, we assume that the protocol participants are semi-honest (i.e., honest-but-curious). In other words, all parties follow the protocol exactly as specified, but at the end of the protocol execution, parties may try to infer additional information about other parties' private inputs based on their view of the protocol execution. Informally, we say that a cryptographic protocol is secure in the semi-honest model if all of the information a party is able to learn from the protocol execution can be expressed as a function of just the party's input to the protocol execution and the output of the computation (i.e., the GWAS results). In Supplementary Note 10, we briefly describe ways of extending our protocol to relax our security assumptions and additionally provide security against malicious adversaries in the online phase of the protocol by applying the techniques from the SPDZ online protocol [3].

Communication Model.

In our protocol, we assume that every pair of parties communicate over a secure and authenticated channel (e.g., over the TLS protocol). Concretely, this means that if $CP_1$ sends a message to $CP_2$ during the protocol execution, only $CP_2$ can read the message; other parties (such as SP, $CP_0$, or an eavesdropper on the network) are unable to do so.

Supplementary Note 2: Secure Multiparty Computation Review

Here, we formally describe a cryptographic framework known as secure multiparty computation (MPC) based on secret sharing, which provides the foundation for our secure GWAS protocol.

2.1 Notation

We begin by introducing some notation that we use throughout this work. For a prime q, we write $\mathbb{Z}_q$ to denote the integers modulo q. For a finite set S, we write $$x \xleftarrow{R} S$$

to denote that x is sampled uniformly at random from S. Our protocols consist of a sequence of operations performed by multiple parties. We annotate each operation with the relevant party or parties that is responsible for performing the operation (unless the operation applies to all parties). We write a tuple with angle brackets (e.g., $\langle a, b, c, d \rangle$) to represent data that are visible to only a subset of the parties in the protocol. The ordering we adopt is $\langle CP_1, CP_2, CP_0, SP \rangle$. In other words, these tuples are placeholders that take on different values depending on which party is executing the corresponding line of the protocol. We write $\perp$ to denote an empty slot, and we adopt the following abbreviations for compactness:

$$\langle a,b \rangle = \langle a,b,\perp,\perp \rangle \text{ and } \langle a,b,c \rangle = \langle a,b,c,\perp \rangle.$$

We give a few examples of our notation in FIG. 4.

2.2 Secret Sharing

Our protocol relies on secret sharing—a cryptographic technique that allows two or more parties to collectively represent a private value without having any knowledge about it individually. The underlying secret is reconstructed only when a prescribed set of parties (e.g., all of them) combine their respective shares. In our setting, the study participants first secret share their data to the two computing parties $CP_1$ and $CP_2$. The protocol execution consists of an interactive protocol where $CP_1$ and $CP_2$ jointly compute over the secret-shared data.

Our protocol relies on a two-party additive secret sharing scheme. A two-party additive sharing of a value $x \in \mathbb{Z}_q$ consists of a pair of values (r, x−r) where $$r \xleftarrow{R} \mathbb{Z}_q$$

is a uniformly random field element. By construction, each share (either r or x−r) individually reveals no information about the value x. However, given both shares r and x−r, it is possible to recover the secret value x by adding together the two shares (hence the name, additive secret sharing). In this work, we denote the two shares (r, x−r) of a value $x \in \mathbb{Z}_q$ by $([x]_1, [x]_2)$, respectively. Using our tuple notation, a secret sharing [x] of a value $x \in \mathbb{Z}_q$ can be written as $$[x] := \langle [x]_1, [x]_2 \rangle.$$

In words, $[x]_1$ and $[x]_2$ are shares of x individually owned by $CP_1$ and $CP_2$, respectively. Adding the two shares together yields the value x. Since $CP_1$ and $CP_2$ each only sees a single share of x, individually, they have no information about the value of x. The procedures for sharing and reconstructing a secret are summarized in Protocols 1 and 2, shown in FIG. 5. Note that the return value of Protocol 2 is $\langle x, x \rangle$, which in our notation, means that both $CP_1$ and $CP_2$ learn the shared value x.

2.3 Computing on Secret-Shared Data

Not only do secret sharing schemes allow data to be shared across multiple parties in a privacy-preserving manner, the parties can exploit the structure of the shared data to additionally compute over the private inputs without learning anything about the underlying inputs [1]. Intuitively, this is akin to manipulating objects while blindfolded. Secure computation of an arbitrary function is typically implemented as a composition of subprotocols that are each defined for primitive operations (e.g., addition and multiplication). Each subprotocol takes secret-shared values as input and outputs the intended result also as secret shares, while ensuring that no information about the private input is leaked in between.

Affine Functions Over Shared Values.

First, consider the case of adding two secret-shared values [x] and [y] without revealing x and y. This is possible by having each party add their own shares. Note that the resulting shares $[x]_1+[y]_1 \in \mathbb{Z}_q$ and $[x]_2+[y]_2 \in \mathbb{Z}_q$ add up to $x+y \in \mathbb{Z}_q$. As long as the shares of $[x]$ and $[y]$ were constructed independently, the resulting shares contain no information about $x+y$. Similarly, adding or multiplying by a public field element $a \in \mathbb{Z}_q$ (represented as $\langle a, a \rangle$ using our notation) is also possible. We describe these basic subroutines in Protocols 3-5, shown in FIG. 6.

Protocols 3-5 together enable secure computation of any affine function over the private input. For notational simplicity, we write affine functions directly in terms of the secret shares [•] without explicitly showing how the basic subroutines are invoked. For instance, we can express the composite protocol for securely evaluating $f(x, y)=ax-y+b$ given shared inputs $[x]$ and $[y]$ and public values a and b as $$[f(x,y)] \leftarrow a[x]-[y]+b.$$

Multiplication of Shared Values.

Multiplication of secret-shared values is more complicated. We adopt a useful tool known as Beaver multiplication triples [7], which are triples of (correlated) random values that can be used for secure multiplication. More precisely, a Beaver multiplication triple is a secret-sharing of a random product: namely, a triple ([a], [b], [c]) where $$a, b \xleftarrow{R} \mathbb{Z}_q$$

are random field elements and $c=ab \in \mathbb{Z}_q$. The key observation is that if two parties possess a secret-sharing of a random multiplication triple, it is possible to compute a secret-sharing of an arbitrary product with a small amount of communication. In this work, we take a server-aided approach [8] to generate the multiplication triples, where we essentially outsource the generation of the multiplication to an auxiliary party (namely, $CP_0$) during a preprocessing step. The Sharemind framework [9] for multiparty computation uses a similar technique in their share multiplication protocol. Protocol 6 outlines the generation of a multiplication triple, and Protocol 7 shows how it is used to perform secure multiplication on shared values. Both protocols are provided in FIG. 7.

Correctness.

Correctness of Protocol 7 follows from the fact that $$xy = ((x-a)+a)((y-b)+b)$$
$$= (x-a)(y-b) + (x-a)b + (y-b)a + ab.$$

Because this expression is affine over the values in a multiplication triple (a, b, and c=ab), it can be securely computed given only the secret-shared triple using Protocols 3-5. Note that x–a and y–b can be treated as public since they are revealed to both parties in Lines 2 and 3 of Protocol 7.

Security.

Unlike previous subroutines, Protocol 7 is interactive, so each party sees additional information beyond their initial input shares. Thus, its security needs to be analyzed more carefully. Consider the view of $CP_1$ in Protocol 7. It observes the secret shares of the multiplication triple ($[a]_1$, $[b]_1$, and $[c]_1$) and the data sent by $CP_2$ in Lines 2 and 3 ($[x]_2-[a]_2$ and $[y]_2-[b]_2$). First, note that $[a]_1$, $[b]_i$, and $[c]_1$ are fresh shares of a, b, and c, and thus are independent of a and b. In addition, a and b are each independently random and unknown to $CP_1$. This means that $[x]_2-[a]_2=([x]_2+[a]_1)-a$ and $[y]_2-[b]_2=([y]_2+[b]_i)-b$ are independent and uniformly random. Thus, the view of $CP_1$ during the protocol execution contain no information about x and y (all the values $CP_1$ sees are distributed uniformly and independently random). The same argument holds for $CP_2$. Overall, neither party learns anything about x and y during Protocol 7 that was not previously known.

With the addition of secure multiplication subroutine (Protocol 7), we now have a general-purpose secure computation framework for arbitrary arithmetic circuits (polynomial functions). In the following, we extend our shorthand notation for composite protocols to include multiplication:

[a][b]:=Secure multiplication of [a] and [b].

Supplementary Note 3: Generalization of Beaver Multiplication Triples

Multiplication triples are traditionally used to compute a product of two secret-shared values. In many scenarios, the direct application of multiplication triples to more complex computations (where each multiplication operation invokes Protocol 7) leads to highly inefficient protocols, especially when there are a large number of multiplications. Here, we describe how to generalize multiplication triples to facilitate the evaluation of arithmetic circuits (i.e., polynomials) on secret-shared data. Our approach is much more practical for complex computations such as computing GWAS statistics, and thus, may be of independent interest. We begin by giving an outline of our method:

1. Input blinding: First, the computing parties $CP_1$ and $CP_2$ "blind" their input value [x] (secret-shared) by subtracting from it a secret random value [r] (also secret-shared). Then, the computing parties publish their shares of [x–r] to reveal the blinded value x–r. Here, the blinding factor r is randomly chosen by $CP_0$ and is secret-shared with $CP_1$ and $CP_2$. We refer to this procedure as Beaver partition (Protocol 8, provided in FIG. 8).
2. Offline computation: All parties ($CP_0$, $CP_1$, and $CP_2$) compute over the Beaver-partitioned data according to the function specification. This step is non-interactive.
3. Output reconstruction: $CP_0$ secret shares the results of its computation (over the blinding factors) with $CP_1$ and $CP_2$. These shares enable $CP_1$ and $CP_2$ to reconstruct the desired output without interaction.

Notably, $CP_0$'s task does not depend on any (secret) input value and thus, can be precomputed and secret-shared in advance. This leads to an efficient protocol where $CP_1$ and $CP_2$ only needs to communicate in the first step of the computation. The core of the computation is non-interactive.

More formally, let $f$ be the arithmetic circuit (represented as a polynomial) that we want to evaluate:

$$f(x_1, \ldots, x_n) := \sum_{t=1}^{T} c^{(t)} x_1^{p_1^{(t)}} \ldots x_n^{p_n^{(t)}},$$

where the number of monomials T, the coefficients $c^{(t)}$, and the exponents $p_i^{(t)}$ are public, and the input is given as secret shares $[x_1], \ldots, [x_n]$.

Input Blinding.

In the first step, the inputs are Beaver-partitioned into (i) public values $x_1-r_1, \ldots, x_n-r_n$ and (ii) hidden (secret-shared) blinding factors $[r_i], \ldots, [r_n]$ (Protocol 8). The computing parties $CP_1$ and $CP_2$ receive $x_1-r_1, \ldots, x_n-r_n$ as well as shares of the blinding factors $[r_1], \ldots, [r_n]$. The auxiliary party $CP_0$ chooses the blinding factors $r_1, \ldots, r_n$.

Next, we re-express the function $f$ as a polynomial in the variables $r_1, \ldots, r_n$ using the substitution $x_i \mapsto r_i + (x_i - r_i)$. Moreover, we treat the values $x_i - r_i$ as a constant for all $i$ (since this value is publicly known to $CP_1$ and $CP_2$):

$$g(r_1, \ldots, r_n) := \sum_{t=1}^{T} c^{(t)} (r_1 + (x_1 - r_1))^{p_1^{(t)}} \ldots (r_n + (x_n - r_n))^{p_n^{(t)}} = \quad (1)$$

$$\underbrace{f(x_1 - r_1, \ldots, x_n - r_n)}_{\text{degree } 0} + \underbrace{\sum_{i=1}^{n} \tilde{d}_i r_i}_{\text{degree } 1} +$$

$$\underbrace{\sum_{t=1}^{\tilde{T}} \tilde{c}^{(t)} r_1^{\tilde{p}_1^{(t)}} \ldots r_n^{\tilde{p}_n^{(t)}}}_{1 < \text{degree} < \deg(f)} + \underbrace{f(r_1, \ldots, r_n)}_{\text{degree } \deg(f)},$$

where we introduce a new set of parameters: coefficients $\tilde{c}^{(t)}$ and $\tilde{d}_i$, exponents $\tilde{p}_i^{(t)}$, and $\tilde{T}$ denoting the number of intermediate-degree terms (between 1 and $\deg(f)$). We separately group degree-one terms and the terms corresponding to $f(r_1, \ldots, r_n)$ and $f(x_1 - r_1, \ldots, x_n - r_n)$ to simplify our subsequent analysis. We enforce that $(\tilde{p}_1^{(t)}, \ldots, \tilde{p}_n^{(t)})$ be unique for each $t = 1, \ldots, \tilde{T}$, and assume that there is a canonical structure for $g$ that is fixed and known to all of the parties. In other words, $\tilde{T}$ and the new exponents $\tilde{p}_i^{(t)}$ are fixed and known to all parties.

Offline Computation.

In the second step, $CP_1$ and $CP_2$ compute the values of $\tilde{c}^{(t)}$, $\tilde{d}_i$, and $f(x_1 - r_1, \ldots, x_n - r_n)$ from the blinded input $x_1 - r_1, \ldots, x_n - r_n$, derived in the first step of the computation. Meanwhile, $CP_0$ computes $$R^{(0)} := f(r_1, \ldots, r_n) \text{ and } R^{(t)} := r_1^{\tilde{p}_1^{(t)}} \ldots r_n^{\tilde{p}_n^{(t)}}, \quad (2)$$

$$\forall t \in \{t, \ldots, \tilde{T}\},$$

which is possible because $CP_0$ knows the blinding values $r_1, \ldots,$

Output Reconstruction.

Finally, $CP_0$ secret shares $R^{(0)}, \ldots, R^{(\tilde{T})}$ with $CP_1$ and $CP_2$. Then, $CP_1$ and $CP_2$ compute $$f(x_1 - r_1, \ldots, x_n - r_n) + \sum_{i=1}^{n} \tilde{d}_i [r_i] + \sum_{t=1}^{\tilde{T}} \tilde{c}^{(t)} [R^{(t)}] + [R^{(0)}], \quad (3)$$

which is $[g(x_1, \ldots, x_n)]$ by Eq. (1). Note this function is affine over the secret inputs $[r_1], \ldots, [r_n]$ and $[R^{(0)}], \ldots, [R^{(\tilde{T})}]$. Therefore, it can be computed non-interactively using Protocols 3-5.

The overall procedure for securely evaluating a polynomial given a secret-shared input is provided in Protocol 9, as shown in FIG. 8. When $f(x_1, x_2) = x_1 x_2$, this procedure reduces to the standard Beaver multiplication protocol (Protocol 7).

Security.

Security of this protocol follows analogously to that for the Beaver multiplication protocol. Namely, the additional data observed by each party in the protocol execution consists entirely of independent random values in $\mathbb{Z}_q$, and thus, do not reveal any information about any secret input. As before, consider the view of each party. In the first step (BeaverPartition), $CP_1$ sees values $[x]_2 - [r]_2 = ([x]_2 + [r]_1) - r$ and $[r]_1$, which are distributed uniformly and independently over $\mathbb{Z}_q$ (since $r$ and $[r]_1$ are independent, uniformly random values of $\mathbb{Z}_q$). An analogous argument holds for $CP_2$. The second step is non-interactive. In the final step, $CP_1$ and $CP_2$ receive secret shares of $CP_0$'s computation results, which individually are independent and uniform over $\mathbb{Z}_q$. Therefore, the views of both $CP_1$ and $CP_2$ in the protocol execution consists of uniformly random values. To conclude the argument, we note that $CP_0$ does not receive any messages from any other party in Protocol 9 (so its view is trivially independent of any secret inputs).

Circuits with Multiple Outputs.

Our method can be further generalized to arithmetic circuits with more than one output as follows. Suppose the circuit has $l$ output gates. We can represent each output by a polynomial $f_1, \ldots, f_l$ on a common set of inputs $x_1, \ldots, x_n$. To avoid redundant computation, we first write out Eq. (1) for each polynomial, and take the union over all intermediate-degree terms to obtain a set $\mathcal{P}$ of exponents $(\tilde{p}_1, \ldots, \tilde{p}_n)$ that include all intermediate-degree terms that emerge in the circuit. During the second step, $CP_0$ calculates $r_1^{\acute{p}_1} \ldots r_n^{\acute{p}_n}$ for each $(\acute{p}_1, \ldots, \acute{p}_n) \in \mathcal{P}$ as well as $f_j(r_1, \ldots, r_n)$ for each $j \in \{1, \ldots, l\}$ and secret-shares these results with $CP_1$ and $CP_2$ in the final step. This provides all necessary terms for $CP_1$ and $CP_2$ to non-interactively compute $[f_j(x_1, \ldots, x_n)]$ for every $j \in \{1, \ldots, l\}$ using Eq. (3).

The Linearization Cost.

We define the linearization cost $\tilde{T}$ of an arithmetic circuit to be the cardinality of the aforementioned union set $\mathcal{P}$ of intermediate-degree terms. Intuitively, $\tilde{T}$ represents the number of extra terms that need to be calculated by $CP_0$ (over the blinding factors) and secret-shared with $CP_1$ and $CP_2$ as a consequence of linearizing the function as in Eq. (3). This notion will be useful in analyzing the efficiency of our Beaver partitioning approach when applied to various arithmetic circuits.

3.1 Comparison with Beaver Multiplication Triples

In FIG. 9, we compare the communication complexity of our method with the standard Beaver multiplication triple method that invokes Protocol 7 for each multiplication gate in the arithmetic circuit. For both approaches, we allow $CP_0$ to precompute all required operations and transfer the shares to $CP_1$ and $CP_2$ in advance, since its computation is input-independent. Also, we allow data transfer to be performed in batches to minimize communication rounds. For instance, this allows the baseline approach to achieve communication rounds equal to the multiplicative depth of the circuit, by batching Lines 2 and 3 of Protocol 7 across different multiplication gates that lie in the same "layer" of the circuit (mutually independent given the output of previous layers).

The key advantage of our generalized method is that irrespective of the number of multiplication gates and depth of the circuit, the online phase only requires a single round of communication and bandwidth equal to the input size. As a tradeoff, however, we incur a potentially large offline communication cost that includes $\tilde{T}$, which is $O(2^d)$ in general. We address this tradeoff by employing our method only in situations where the benefits clearly outweigh the costs. In the following, we highlight three concrete scenarios where our generalized Beaver partitioning approach is useful in the context of performing large-scale GWAS.

3.2 Scenario 1: Depth-One Circuits (e.g., Matrix Multiplication)

When the multiplicative depth of the circuit is at most one ($\deg(f) \leq 1$), there are no intermediate-degree terms in Eq. (1), and the linearization cost becomes zero ($\tilde{T}=0$). A frequent operation in GWAS for which this property holds is matrix multiplication. Suppose we want to compute the product of two secret-shared matrices with dimensions $d_1 \times d_2$ and $d_2 \times d_3$. Even though this operation requires evaluating $m=d_1 d_2 d_3$ pairwise multiplications, the multiplicative depth d of the overall computation is 1. Moreover, the arithmetic circuit for performing matrix multiplication contains $d_1 d_2 + d_2 d_3$ inputs and $d_1 d_3$ outputs. Substituting these values into the expression in FIG. 9, we obtain complexities as shown in FIG. 10. Notably, using our Beaver partitioning technique, both the online and offline bandwidth is proportional to the size of the matrices (i.e., quadratic in the dimensions) rather than the number of multiplications (i.e., cubic in the dimensions). This difference is critical for building a practical GWAS protocol that can support millions of individuals and SNPs.

3.3 Scenario 2: Variable Reuse

Because our generalized Beaver partitioning method can evaluate circuits with multiple outputs, multiple operations (each represented as a circuit) that share common inputs can be combined into a single circuit for joint evaluation. In doing so, each input only needs to be Beaver partitioned once, which is more efficient than constructing a fresh Beaver partition for each operation individually. In fact, we can implicitly combine circuits operating on common inputs by reusing the Beaver partitions on the common inputs across multiple invocations of Protocol 9.

More precisely, given a secret-shared input [x] involved in the evaluation of $f_1(x, \ldots)$ followed by $f_2(x, \ldots)$, we can simulate the joint evaluation of $f_1$ and $f_2$ by obtaining the Beaver partition of [x] during the evaluation of $f_1$ and reusing the results, namely $\langle x-r, x-r \rangle$ and $\langle [r]_1, [r]_2, r \rangle$ for a uniformly and independently random $r \in \mathbb{Z}_q$, for $f_2$. Note this does not affect the security of our method, because in every invocation of BeaverPartition or ShareSecret in the overall protocol, the views of $CP_1$ and $CP_2$ still consist only of uniform and independent values in $\mathbb{Z}_q$.

As a concrete example, consider the following power iteration procedure that appears in our randomized PCA protocol (Protocol 32):

for each t in 1, . . . ,T do
    $A^{(t)} \leftarrow G^T G A^{(t-1)}$
end for where G is $d_1 \times d_2$ and $A^{(t)}$ is $d_2 \times d_3$ for all t. In practice, $d_1$ and $d_2$ are large while $d_3$ is small. Even with our improved method for secure matrix multiplication (Scenario 1), carrying out this computation by considering each multiplication separately would require Beaver partitioning G a total of 2T times—a prohibitive cost for a large G. With the reuse of Beaver partitioned data, we need to Beaver partition G only once. This is another key factor in achieving practicality for large-scale GWAS. The complexity comparison for this example is shown in FIG. 11.

3.4 Scenario 3: Exponentiation

Exponentiation is a special case where the linearization cost grows linearly with the circuit depth. Specifically, consider a circuit that takes a single value x as input and outputs all powers of x up to a known parameter $\alpha \geq 2$: $x^2, \ldots, x^\alpha$. For simplicity, assume that the circuit is naïvely represented as a sequence of $\alpha-1$ pairwise multiplications. In this case, the circuit has 1 input, $\alpha-1$ outputs, depth $\alpha-1$, and consists of $\alpha-1$ multiplication gates. Its linearization cost $\tilde{T}$ is $\tilde{T}=\alpha-2$, since there are $\alpha-2$ intermediate powers of the blinding factor (from 2 to $\alpha-1$) that needs to be calculated and shared by $CP_0$. Using the asymptotic analysis given in FIG. 9, we compare our Beaver partitioning method to the standard method of directly applying multiplication triples in FIG. 12. Our method has the advantage that it is single-round (compared to $\alpha-1$ rounds), and the online communication consists of a single field element (compared to $2(\alpha-1)$). The offline bandwidth is still linear in the exponent $\alpha$, though the constants are modestly smaller. The online savings in communication and round complexity leads to a significant increase in efficiency in our GWAS protocol, as this subroutine (Protocol 10) is frequently invoked as part of the secure table lookup operation (Protocol 11), both shown in FIG. 13.

Supplementary Note 4: Protocol Building Blocks

Here, we introduce a number of protocol building blocks that we leverage when constructing our GWAS protocol.

4.1 Table Lookup

Let $T=\{k_i \mapsto v_i\}_{i=1}^d$ be a public table that maps keys $k_i$ to values $v_i$, where $k_i, v_i \in \mathbb{Z}_q$ for all $i \in \{1, \ldots, d\}$. The table lookup functionality takes as input a key $k \in \mathbb{Z}_q$ and returns a value $v \in \mathbb{Z}_q$, where $v=T(k)$ if k is in the table. If k is not present in the table, then the output of the table lookup is undefined (can be an arbitrary field element). A table lookup on secret-shared inputs corresponds to the setting where the input key [k] is secret-shared, and the output should be a secret sharing of the value [v]. Table lookups can be implemented by representing the entries in the table as points on a polynomial $f$. Then, looking up a key k in T just corresponds to evaluating the polynomial on k. We write LagrangeInterpolation to denote an algorithm that takes as input a table T of d values and outputs a polynomial (of degree d−1) that interpolates the mappings in T:

LagrangeInterpolation(T)→$c_0, \ldots, c_{d-1}$: On input a table $T=\{k_i \mapsto v_i\}_{i=1}^d$, the Lagrange interpolation algorithm return the coefficients $c_0, \ldots, c_{d-1}$ of a polynomial $f(x)=\Sigma_{i=0}^{d-1} c_i x^i$ where $f(k_i)=v_i$ for all $i \in \{1, \ldots, d\}$.

By representing tables as polynomials, table lookup just corresponds to polynomial evaluation. To perform polynomial evaluation on a secret-shared input, we first define a subprotocol Powers that securely computes all powers of input up to a given exponent (Protocol 10) using our generalized Beaver partitioning approach (Supplementary Note 3). After obtaining $[k^t]$ for $t=2, \ldots, d-1$ via this subroutine, the interpolated polynomial can be easily evaluated as an affine function $\Sigma_{t=0}^{d-1} c_t[k^t]$. This procedure is summarized in Protocol 11.

4.2 Bitwise Operations

We now describe several protocols for performing bitwise operations on secret-shared inputs. Let $\{[a_i]\}_{i=1}^L := \{[a_1], \ldots, [a_L]\}$ be a secret L-bit vector where $a_i \in \{0, 1\}$ for all i, and every individual bit is secretly shared.

The FanInOr subroutine (Protocol 12, FIG. 14) securely computes the disjunction ("or" operation) of all of the bits by performing a table lookup using the sum of bits as the key (i.e., a table where the value 0 maps to 0 and all other values map to 1).

Next, the PrefixOr subroutine (Protocol 13, FIG. 14) efficiently computes FanInOr of all L prefixes of the bit vector in a way that does not require invoking FanInOr on each prefix [10]. The communication in the optimized protocol scales linearly in L (instead of quadratically in L in the case of the nave protocol). Note that Lines 12-14 of Protocol 13 can be carried out as a group using our Beaver partitioning method to increase efficiency, since it is a depth-one circuit (Supplementary Note 3, Section 3.2). The same optimization applies to Lines 18-20.

BinaryLessThan (Protocol 14, FIG. 15) is a subroutine that takes the binary representation of two integers (i.e., bit vectors) and returns a share of the comparison result. Our protocol is based on Damgård et. al [11]. The main technique used is drawn from a well-known solution of Yao's millionaire problem [12]. Note that the Lines 1-3 and 5 of Protocol 14 are depth-1 arithmetic computations, and thus, can be more efficiently implemented using our Beaver partitioning method. Moreover, when one of the numbers being compared is known to both $CP_1$ and $CP_2$, both Lines 1-3 and 5 turn into affine functions over the secret inputs, and thus can be calculated non-interactively. This special case is described in BinaryLessThanPublic (Protocol 15, FIG. 15).

Supplementary Note 5: Computing with Fixed-Point Numbers

To use secret sharing in practice, we need to define a mapping between data values and field elements. In this work, we use a fixed-point (FP) representation [13] to represent real-valued numbers that appear during the GWAS computation. Various building blocks for secure computation with FP numbers, including division, have been proposed by Catrina and Saxena [13]. Here, we recall their protocols and describe several optimizations that we make in our work (namely, using a server-aided design and removing the dependence on the secure bit-decomposition subroutine). We additionally describe novel square-root and square-root inversion subroutines, which are frequently invoked in GWAS.

5.1 Data Representation

Let k be the number of bits we use to represent a signed real number, of which $f$ bits are allocated to the fractional domain (referred to as the precision). The values of k and $f$ are chosen such that any real number we expect to encounter during the protocol falls in the range $$\mathcal{D} := [-2^{k-f-1}, 2^{k-f-1}) \subset \mathbb{R}.$$

We map each $x \in \mathcal{D}$ to an element in the finite field $\mathbb{Z}_q$ using the encoding function $$E_f(x) = \lfloor x \cdot 2^f \rfloor \bmod q,$$

where $\lfloor \cdot \rfloor$ denotes the floor function. Conversely, each field element $z \in \mathbb{Z}_q$ is mapped back to real data space $\mathcal{D} \cup \{NaN\}$ using the following decoding function:

$$D_f(z) = \begin{cases} z \cdot 2^{-f} & \text{if } 0 \le z < 2^{k-1}, \\ -(q-z) \cdot 2^{-f} & \text{if } q - 2^{k-1} \le z \le q - 1, \\ NaN & \text{otherwise}. \end{cases}$$

Intuitively, this representation corresponds to taking a real number in $\mathcal{D}$ and truncating it to the closest multiple of $2^{-f}$.

Notation.

We write $[E_f(x)]$ to denote a secret-share of a value $x \in \mathcal{D}$. We alternatively express this as $$[x]^{(f)} := [E_f(x)] \text{ for } x \in \mathcal{D}.$$

We use the same base field $\mathbb{Z}_q$ for all values of $f$ for interoperability. We choose q to be large enough for the highest precision required. Secret sharing of integers $x \in \mathcal{D}$ with an identity encoding function (i.e., $[x]^{(0)}$) is denoted without the superscript as $[x]$, i.e., $$[x] := [x]^{(0)} \text{ for } x \in \mathcal{D} \cap \mathbb{Z},$$

since it is equivalent to directly treating the integer as an element in $\mathbb{Z}_q$.

5.2 Arithmetic Operations

Addition and subtraction of secret-shared fixed-point values correspond to addition and subtraction on the underlying secret-shared field elements, provided that the fixed-point values are encoded with the same precision. In particular, we define $$[x \pm y]^{(f)} := [x]^{(f)} \pm [y]^{(f)} \text{ and } [x \pm a]^{(f)} := [x]^{(f)} \pm E_f(a),$$

for secret-shared values x, $y \in \mathcal{D}$ and public constant $a \in \mathcal{D}$. Unlike the case of adding and subtracting shares of field elements, adding and subtracting shares of encoded fixed point values introduces a small amount of error (bounded by $\frac{1}{2}^{f-1}$). To see why, observe that by construction, the shared value $[x]^{(f)} + [y]^{(f)}$ is an additive sharing of $D_f(E_f(x)) + D_f(E_f(y))$. Due to the imprecision introduced by the fixed-point encoding, this value is close to $[x \pm y]^{(f)} = D_f(E_f(x+y))$, but there is some error due to the non-linearity of the encoding/decoding procedures.

Multiplying two FP numbers requires an additional step. Note that directly multiplying two encoded FP numbers outputs a result with precision $2f$ instead of $f$. In particular, we write $$[xy]^{(2f)} := [x]^{(f)} [y]^{(f)}.$$

To scale the precision back to $f$, we use the Truncate subroutine (Protocol 16) from Catrina and Saxena [13], as shown in FIG. 16. Given public values b and s, this protocol truncates the s least significant bits of a secret-shared integer (in our case, the encoding of a FP number). The output is a secret-sharing of the most significant b bits of the truncated input. The resulting secure multiplication protocol for FP numbers, MultiplyFP, is shown as Protocol 17 in FIG. 16.

Security.

Notably, Line 5 of Truncate reveals the value x+r in the clear (to $CP_1$ and $CP_2$), where r is uniform over the set $\{0, \ldots, 2^{b+\kappa}+1\}$, and $x \in \{0, \ldots, 2^b-1\}$. Assume that the base prime q is large enough such that x+r does not overflow. Then, the distribution of x+r is statistically close to the uniform distribution over $\{0, \ldots, 2^{b+\kappa}-1\}$. More precisely, the statistical distance between the two distributions is bounded by $2^{-\kappa}$ for all $x \in \{0, \ldots, 2^b-1\}$. (Note that the statistical distance between two distributions $\mathcal{D}_1$ and $\mathcal{D}_2$ over a common finite domain $\chi$ is defined to be $$\frac{1}{2} \sum_{x \in \chi} |Pr[\mathcal{D}_1(x)] - Pr[\mathcal{D}_2(x)]|.$$

This implies no adversary (including computationally unbounded ones) is able to distinguish x+r from a uniformly random field element r', except with an advantage $2^{-\kappa}$—i.e., the difference in the a posteriori guessing probability of a given candidate being a real message (i.e., x+r) between the two candidates (i.e., r' and x+r, randomly shuffled) is upper-bounded by $2^{-\kappa}$, where 0 corresponds to perfect indistinguishability. Thus, $CP_1$ and $CP_2$ effectively sees x+r as a uniformly random element, and do not learn anything about x from it as a result.

Our overall GWAS protocol requires multiple invocations of the Truncate protocol, which increases the adversary's distinguishing advantage by a multiplicative factor v equal to the total number of invocations (based on a standard hybrid argument; cf. [14, § 3.2.3]). In practice, we choose our statistical security parameter κ such that the adversary's distinguishing advantage $v \cdot 2^{-\kappa} < 2^{-30}$, or equivalently, $\kappa - \log_2(v) > 30$. This ensures that the view of each party in the overall protocol is statistically indistinguishable from a sequence of uniformly random field elements.

Next, since $2^{b+\kappa}$ lower-bounds the base prime q we use for the overall protocol, which in turn determines the overall efficiency, we choose the smallest possible b for each invocation of Truncate. For example, in Line 2 of MultiplyFP, we choose $b = k + f$. Recall that by assumption, every value encountered during the protocol lies in $\mathcal{D}$. This means that $xy \in \mathcal{D}$, which implies $E_{2f}(xy)$ has effective bit-length at most $k + f$.

5.3 Field Conversion

The following sections describe protocols in which individual bits of a secret integer are separately secret-shared. To exploit the smaller field size needed for bit operations compared to FP operations, we instead perform operations over an auxiliary field $\mathbb{Z}_{q'}$, where $q' \ll q$. We write $[[x]] := \langle [[x]]_1, [[x]]_2 \rangle$ to denote a secret sharing over $\mathbb{Z}_{q'}$. Because our use of the auxiliary field is limited to unsigned integers, the mapping between the data space and the auxiliary field is simply the identity map over $\{0, \ldots, q'-1\}$. When appropriate, we invoke subroutines previously defined over [.] with the secret shares [[•]]. In our protocols, secret shares over $\mathbb{Z}_{q'}$ are constructed using the function ShareSecretSmallField defined as follows:

ShareSecretSmallField($\langle \perp, \perp, x \rangle$, q') → [[x]]: Same as ShareSecret (Protocol 1) except x is shared in the smaller field $\mathbb{Z}_{q'}$.

After operating on the secret-shared bits, the resulting secret shares can be mapped back into the large field $\mathbb{Z}_q$ via TableLookupWithFieldConversion (Protocol 18, shown in FIG. 17). In other words, the TableLookupWithFieldConversion algorithm converts a secret sharing of $x \in \mathbb{Z}_{q'}$ into a secret-sharing of $x \in \mathbb{Z}_q$. The field conversion algorithm relies on the observation that if we simply view [[x]] as a secret sharing of x over the large field $\mathbb{Z}_q$, then performing the reconstruction (namely, computing $[[x]]_1 + [[x]]_2$ in $\mathbb{Z}_q$) either yields the value $x \in \mathbb{Z}_q$ or the value $x + q' \in \mathbb{Z}_q$. We can thus use TableLookup to map each of these two possibilities for x' to the value $x \in \mathbb{Z}_q$. Of course, this approach is efficient only if there are just a few possible values to convert (e.g., if $\mathbb{Z}_{q'}$ is small). This is indeed the setting of our protocol, since the outputs of bit operations lie in a small range.

5.4 Comparison

To implement a comparison protocol on secret-shared fixed-point values, we first implement a secure sign test for FP values (i.e., a comparison with zero). Here, we use the technique of Nishide and Ohta [15] for comparing elements of $\mathbb{Z}_q$ to the value q/2 (as a real number). Given a secret-shared FP value $[x]^{(f)}$, the idea is to securely retrieve the least significant bit of $2 \cdot E_f(x)$. If x is negative, then $E_f(x) > q/2$, and thus $2 \cdot E_f(x)$ wraps around and results in an odd integer (since $q > 2$ is odd). On the other hand, if x is positive, then $E_f(x) < q/2$, which implies $2 \cdot E_f(x)$ is even. Thus, retrieving the least significant bit of $2 \cdot E_f(x)$ is equivalent to performing a sign test on x. The least significant bit is securely obtained by manipulating the binary representation of $2 \cdot E_f(x) + r$, where the blinding factor r is sampled uniformly at random and secret-shared by $CP_0$. The overall procedure is shown in IsPositive (Protocol 19), provided in FIG. 17. Note we make use of the following helper functions:

BitLength(x) → l: Returns the bit length of an integer x.

BinaryRepresentation(x, L) $\{a_i\}_{i=1}^L$: Takes a field element $x \in \mathbb{Z}_q$ and returns the L least significant bits $a_1, \ldots, a_L$ of its binary representation in decreasing order of significance.

Security.

The security of IsPositive follows from the security of secret sharing (Lines 4-7) and the fact that $2E_f(x) \times r$ in Line 8 does not reveal any information about x to either party, since r is uniformly random and independent from all other values.

Comparing Secret-Shared FP Values.

The IsPositive protocol can be used to compare two secret-shared FP values $[x]^{(f)}$ and $[y]^{(f)}$ by casting the problem as a sign test of the difference $[y]^{(f)} - [x]^{(f)}$. This extended protocol is named LessThan (Protocol 20). Additionally, we define LessThanPublic (Protocol 21) for the setting where one of the input values is known to both $CP_1$ and $CP_2$. Both protocols are provided in FIG. 18.

5.5 Division and Square Root

We implement division and square root routines (for FP values) using Goldschmidt's algorithm [16], which approximates the desired operation as a series of multiplications. Each iteration quadratically reduces the relative approximation error.

Goldschmidt's Algorithm for Division.

Take two real numbers a, $b \in \mathbb{R}$. We describe Goldschmidt's algorithm for approximating the quotient $a/b \in \mathbb{R}$. Let $w_0$ be an initial approximation of 1/b and let $\epsilon_0 := 1 - bw_0$ be the relative error for the approximation $w_0$. We require that $|\epsilon_0| < 1$. The algorithm iteratively computes the following:

$$x_t \leftarrow x_{t-1}(1 + y_{t-1})$$

$$y_t \leftarrow y_{t-1} y_{t-1}$$

with $x_0 = aw_0$ and $y_0 = \epsilon_0$. Here, $x_t$ converges to a/b [16].

Goldschmidt's Algorithm for Square Root.

For computing the square root of a value $a \in \mathbb{R}$, Goldschmidt's algorithm starts with an initial approximation $w_0$ of $1/\sqrt{a}$. As before, let $\epsilon_0 := 1 - aw_0^2$ denote the relative error in the approximation. We require that $|\epsilon_0| < 1$. The algorithm then iteratively computes $$z_{t-1} \leftarrow 1.5 - x_{t-1} y_{t-1}$$

$$x_t \leftarrow z_{t-1} x_{t-1}$$

$$y_t \leftarrow z_{t-1} y_{t-1}$$

with $x_0 = aw_0$ and $y_0 = w_0/2$. Here, $x_t$ converges to $\sqrt{a}$ and $2y_t$ converges to $1/\sqrt{a}$ [16]. Note we obtain the square root inverse of a for free.

Choosing the Number of Iterations.

Normally, if the input is available in the clear, we would iterate Goldschmidt's algorithm until the values satisfy some convergence criterion. However, this strategy does not extend to the secure computation setting when the number of iterations needed before convergence could itself reveal information about the underlying inputs. In our protocol execution, we thus take an oblivious evaluation approach and instead fix the number of iterations in advance and always iterate the algorithm for that many rounds. We choose the number of iterations to be sufficiently large to ensure the desired level of accuracy. In this work, we follow the recommendation from a previous work [13] and use $2\lceil\log_2(k/3.5)\rceil$ iterations for both the division and square root routines. An extra iteration is added for division protocol to account for our initial approximation (described below) being slightly less accurate, albeit more efficient, than what was proposed in the original work.

Computing the Initial Approximations.

For both the division and square root routines, we require a suitable initial approximation $w_0$ of $1/x$ or $1/\sqrt{x}$ to ensure convergence of the iterative procedure. We achieve this by first scaling the input to be within $[0.25, 1)$ and evaluating a quadratic polynomial that approximates the desired function within that range. Reverse scaling is performed to map the approximation back to the scale of input.

We introduce a new protocol NormalizerEvenExponent (Protocol 22, shown in FIG. 19) to efficiently handle the scaling operation, which is based on the constant-round bit length protocol of Dahl et. al [17]. Notably, our protocol replaces the expensive bit decomposition routine that previous work relied on [13]. The protocol NormalizerEvenExponent takes as input a secret-shared integer $[z]$, and returns two secret numbers $[2^{2t}]$ and $[2^t]$ such that $2^{k-2} \leq 2^{2t} z < 2^k$. Since the algorithm is rather involved, we refer the readers to the [17, Appendix A.1] for a description of the technique. In this work, we modify their algorithm to return the normalization factor instead of the bit-length of the input and added an extra step of finding the closest even power of two, which is achieved by splitting a bit vector into even and odd bits (Lines 22 and 23 of NormalizerEvenExponent). Similar to Truncate, the NormalizerEvenExponent protocol achieves statistical security (with statistical security parameter κ) as opposed to perfect security. In particular, Line 7 of NormalizerEvenExponent blinds the input value x (which has at most k bits) with a uniformly random value from $\{0, \ldots, 2^{k+\kappa}1\}$. The distribution of the blinded value $x+r$ is at least $2\kappa$-close to the uniform distribution over $\{0, \ldots, 2^{k+\kappa}1\}$.

After obtaining $[2^{2t}]$ and $[2^t]$ where $2^{k-2} \leq 2^{2t} \cdot z < 2^k$ for the input value $[x]^{(f)}$, we scale x to $[0.25, 1)$ by truncating $k-f$ bits of $[2^{2t}][x]^{(f)}$ with Truncate. The resulting scaled input is denoted $[\overline{x}]^{(f)}$. We only need to mask k bits during Truncate (i.e., b=k), since $2^{2t} \cdot E_f(x) < 2^k$. Note that we assume $x>0$ during this process, which is always the case in our GWAS protocol. One can additionally support $x<0$ by performing an additional sign test and providing $[|x|]^{(f)}$ as input to NormalizerEvenExponent.

Given the scaled input $[\overline{x}]^{(f)}$, we approximate the desired function by securely evaluating the quadratic polynomials $$\frac{1}{\overline{x}} \approx 5.9430 - 10\overline{x} + 5\overline{x}^2 \text{ and } \frac{1}{\sqrt{\overline{x}}} \approx 2.9581 - 4\overline{x} + 2\overline{x}^2,$$

where the coefficients of non-constant terms are chosen to be integers to avoid adding an extra call to Truncate. The resulting estimate, denoted $[\overline{w}_0]$, is scaled back to match the input as follows. For division, as noted in previous work [13], we can exploit the fact that $$\frac{1}{x} = 2^{2t-(k-f)} \frac{1}{2^{2t-(k-f)}x} = 2^{2t-(k-f)} \frac{1}{\overline{x}} \approx 2^{2t-(k-f)} \tilde{w}_0.$$

Thus, we approximate $1/x$ as $$[w_0]^{(f)} \leftarrow \text{Truncate}([2^{2t}][\overline{w}_0]^{(f)}, k+f+2, k-f).$$

Note our scaled approximation $\overline{w}_0 < 4$ for $\overline{x} \in [0.25, 1)$. Thus, we set $b=k+f+2$ for Truncate since $2^{2t} E_f(\overline{w}_0)$ has at most $k+f+2$ bits.

Adapting the above approach for the inverse square root, we observe $$\frac{1}{\sqrt{x}} = 2^{t-\frac{k-f}{2}} \frac{1}{\sqrt{2^{2t-(k-f)}x}} \approx 2^{t-\frac{k-f}{2}} \tilde{w}_0,$$

which leads to $$[w_0]^{(f)} \leftarrow \text{Truncate}([2^t][\overline{w}_0]^{(f)}, \lfloor k/2 \rfloor + f + 2, (k-f)/2)$$

for approximating $1/\sqrt{x}$. Here, $b=\lfloor k/2 \rfloor +f+2$ is sufficient, since $2^t$ is at most $\lfloor k/2 \rfloor$ bits and $\overline{w}_0 < 4$ as before. Importantly, we require $k-f$ to be even in order to ensure $(k-f)/2$ is an integer.

The resulting subroutines Divide and SqrtAndSqrtInverse are shown as Protocols 23 and 24 in FIG. 20. The security of both subroutines follow from the security of individual building blocks that are invoked during the procedure.

Supplementary Note 6: Choice of Base Primes

Here, we describe how we choose the size of finite fields (e.g., $\mathbb{Z}_q$) for secret sharing.

Choosing the Primary Field $\mathbb{Z}_q$.

Recall first that our supported data range $\mathcal{D} \subset \mathbb{R}$ is defined to be $[-2^{k-f-1}, 2^{k-f-1})$, where k is the total number of bits used for the fixed point representation and $f<k$ is the number of bits assigned to the fractional range. Also, κ is the statistical security parameter for the subroutines that provide statistical security guarantees (i.e., Truncate and NormalizerEvenExponent). Whenever we multiply two secret-shared FP values, we obtain the value $[x]^{(2f)}$ for some $x \in \mathcal{D}$. This means q must have at least $k+f$ bits. Moreover, invoking Truncate subroutine on $[x]^{(2f)}$ to obtain $[x]^{(f)}$ requires us to generate a $(k+f+\kappa)$-bit random number (Line 1 of Truncate, with $b=k+f$), which lower bounds q at $2^{k+f+\kappa}$. We ensure that the maximum precision of a secret FP number in our protocol is $2f$ (by invoking Truncate when necessary), although one could use higher precisions at the expense of increasing q. In our setting, the highest lower bound on q is introduced by Line 6 of Divide where we invoke Truncate with $k+f+2$. Thus, our final requirement for q is $$q > k+f+\kappa+2.$$

Choosing the Auxiliary Fields.

Figure 21:
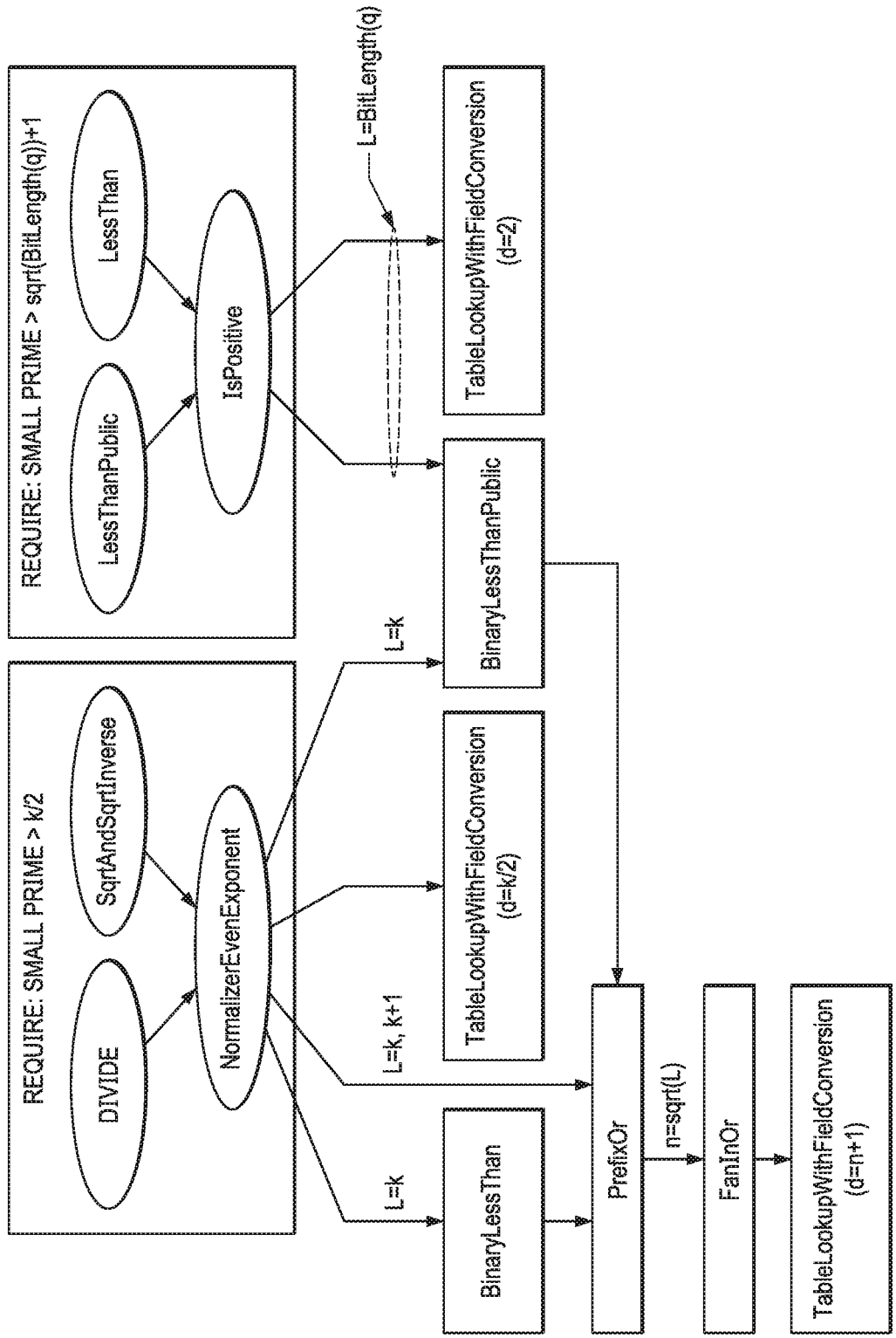
FIG. 21 depicts a call graph of subroutines that utilize an auxiliary finite field.

For the small auxiliary field for bit operations, we choose two different base primes $q_1$ and $q_2$ for maximal efficiency. FIG. 21 shows the call graph of subroutines that involve bit operations.

In our protocols, TableLookupWithFieldConversion imposes a lower bound on the small prime, as the size of the field must be at least as large as the number of entries in the table. When the secret shares are being constructed in the auxiliary field, we find all associated table lookups and choose the smallest prime that is larger than the largest table size. In summary, NormalizerEvenExponent, which Divide and SqrtAndSqrtInverse depend on, uses $$q_1 > k/2,$$

whereas IsPositive, which LessThanPublic and LessThan depend on, uses $$q_2 > \sqrt{\text{BitLength}(q)}+1.$$

Note that $q_2$ is often much smaller than $q_1$, and thus our use of two auxiliary fields leads to a substantial improvement in efficiency compared to a one-size-fits-all approach.

In addition, we note that our use of NormalizerEvenExponent for Divide, as opposed to the more natural normalization routine without the requirement of the exponent being even, is intended for efficiency. If we were to take the alternative approach, the size of the table lookup at the end of the procedure becomes k instead of k/2. This doubles the size of the small field used for the entire protocol execution, which in turn, effectively doubles the amount of communication.

Parameters for experiments.

The parameter setting we used for our benchmark experiments is as follows: $k=60$, $f=30$, $\kappa=64$, $q=2^{160}-47$, $q_1=31$, and $q_2=17$. Base primes $q$, $q_1$, and $q_2$ are chosen to satisfy the requirements above. The data range parameters k and $f$ naturally depend on the input data dimensions and the required level of precision. Our choice was sufficient to obtain accurate results for the benchmark data sets. While larger data may require higher precision, we note that even doubling the precision (e.g., $k=120$ and $f=60$) increases the size of each field element (the bit length of q) by only roughly 40%, and thus maintains the practical feasibility of our protocol.

Supplementary Note 7: Further Optimization with Shared Random Streams

To further improve performance, we use a pseudorandom generator (PRG) to generate the random bits (used primarily for secret sharing and Beaver partitioning). At a high level, a PRG takes as input a short uniformly random seed (e.g., 128-bits) and outputs a long stream of random-looking bits (e.g., $2^{64}$ bits). The security guarantee is that no "efficient" adversary (i.e., a polynomial-time algorithm) is able to distinguish the output of the PRG from a uniformly random sequence of random bits. Using a PRG to derive a random stream of bits allows us to significantly reduce the communication needed in the protocol. For instance, instead of sending a party a long stream of uniformly random bits, one can instead send a short PRG seed and have the receiving party derive the random bits by evaluating the PRG.

This optimization significantly improves the performance of ShareSecret and BeaverPartition. Protocols 25 and 26, provided in FIG. 22, show the improved versions of the respective protocols using shared random streams, which are denoted as $PRG_\mathcal{P}$ := An instance of pseudorandom generator shared among the parties in $\mathcal{P}$.

In ShareSecretSharedPRG, the data owner (either SP or $CP_0$) communicates with one of the main computing parties only, since the other party can obtain its share from the shared random stream. Next, in BeaverPartitionSharedPRG, we replace $CP_0$'s sampling of r with an implicit sampling procedure, where $CP_1$ and $CP_2$ randomly chooses the respective shares $[r]_1$ and $[r]_2$ first and $CP_0$ retroactively recovers r by adding the two shares obtained offline via the shared random streams. Since $[r]_1$ and $[r]_2$ are uniformly random, we maintain the property that r is uniformly random. Note $CP_0$ does not communicate with $CP_1$ or $CP_2$ in this modified protocol neither online nor offline (precomputation). We summarize the improved communication complexities of our method for previously described settings in FIG. 23.

Using PRGs to construct the random streams significantly reduces the bandwidth of our overall protocol. In particular, the initial Beaver partitioning of the input genotype matrix (a matrix with a million rows and a million columns) no longer requires $CP_0$ to send an equally-large random matrix to each of the main computing parties ($CP_1$ and $CP_2$). In fact, because the communication needed for matrix multiplication in our Beaver partitioning framework is proportional to the size of the output matrix (FIG. 23), this yields a considerable communication reduction if we ensure that all matrix multiplications involving the genotype matrix outputs a thin (but long) matrix or a short (but fat) matrix. In this way, we effectively reduce the communication complexity for Beaver partitioning the initial genotype matrix from quadratic to linear in the dimensions of the genotype matrix (which constitutes a million-fold improvement in many realistic scenarios).

Supplementary Note 8: Secure Linear Algebra Subroutines

Here, we describe the subroutines for linear algebraic operations that we developed and used to implement principal component analysis (PCA) in GWAS.

Notation.

We extend our previous notation for secret sharing to matrices (which includes vectors and scalars as special cases). Typically, we will use bold-faced uppercase letters (e.g., A, B) to denote matrices and bold-faced lowercase letters (e.g., u, v) to denote vectors. For a matrix $A \in \mathbb{R}^{n \times m}$ and an index $1 \leq i \leq n$ we write $A_{i,:}$ to denote the submatrix corresponding to the bottom $n-i+1$ rows of A (namely, the matrix consisting of rows $i, i+1, \ldots, n$ of A). We write $A_{:i,:}$ to denote the submatrix consisting of the top i rows of A. Similarly, for a column index $1 \leq j \leq m$, we write $A_{:,j:}$ to denote the submatrix consisting of the rightmost $m-j+1$ columns of A, and $A_{:,:j}$ to denote the leftmost j columns of A. In some cases, we also combine the two; for instance, we write $k_{:i,:j}$ to denote the submatrix of A containing the first i rows and j columns of A.

For a real-valued matrix $A \in \mathbb{R}^{n \times m}$, we define its secret sharing to be a secret-sharing of the fixed-point encoding of A:

$$[A]^{(f)} := \begin{bmatrix} [A_{1,1}]^{(f)} & \cdots & [A_{1,m}]^{(f)} \\ \vdots & \ddots & \vdots \\ [A_{n,1}]^{(f)} & \cdots & [A_{n,m}]^{(f)} \end{bmatrix}.$$

We also extend our previously-defined protocols and functions that operate on scalar values to operate component-wise on matrices. For instance, invoking ShareSecret or ShareSecretSharedPRG on a matrix is equivalent to invoking the protocol on each element in parallel so that every element is individually secret shared.

Secure Arithmetic with Matrices.

Much of our previous discussion in Supplementary Note 2 naturally extends to arithmetic operations with matrices. For example, affine functions over secret-shared matrices can be performed non-interactively, since each element of the resulting matrix is an affine function over the secret-shared elements in the input. Secure multiplication of two matrices is efficiently handled by our generalized Beaver partitioning method (Supplementary Note 3, Section 3.2). Furthermore, if the same matrix is used across multiple multiplications, its Beaver-partitioned data can be reused (Supplementary Note 3, Section 3.3). Note that to simplify the protocol description, we do not explicitly describe how the variable reuse optimization is applied in our protocol.

Protocols.

We now describe the subroutines used for PCA. All of the protocols described here implement secure computations over secret-shared real values (represented as fixed-point values, as described in Supplementary Note 5).

Householder($[x]^{(f)}$)→$[v]^{(f)}$: On input a secret-shared vector $[x]^{(f)}$ where $x \in \mathbb{R}^d$, the Householder protocol (Protocol 27, shown in FIG. 24) outputs a share $[v]^{(f)}$ of a unit vector $V \in \mathbb{R}^d$ such that the reflection of x about the hyperplane associated with v (this is also known as the "Householder reflection") yields a vector that is a multiple of the elementary vector $e_1$ (i.e., only the first element is non-zero). In other words, $(1-vv^T)x = \alpha e_1$ for some $\alpha \in \mathbb{R}$.

QRFactorizeSquare($[A]^{(f)}$) ($[Q]^{(f)}$, $[R]^{(f)}$): On input a secret-shared matrix $[A]^{(f)}$ where $A \in \mathbb{R}^{d \times d}$, the QRFactorizeSquare protocol (Protocol 28, shown in FIG. 25) securely executes a standard QR factorization algorithm, which applies d−1 Householder transformations $Q_1, \ldots, Q_{d-1}$ to A to obtain an upper-triangular matrix $R = Q_{d-1} \ldots Q_1 A$. Setting $Q := Q_1 \ldots Q_{d-1}$ yields the QR factorization A=QR. The output of the protocol are secret shares $[Q]^{(f)}$ and $[R]^{(f)}$ of Q and R, respectively. We also present a modified protocol QRFactorizeRectangle (Protocol 29, shown in FIG. 26) for tall and skinny matrices A where the number of rows d is large enough that storing a d-by-d matrix in memory (as in QRFactorizeSquare) is not feasible. This is the case in our GWAS application.

Tridiagonalize($[A]^{(f)}$)→($[Q]^{(f)}$, $[T]^{(f)}$): On input a secret-shared symmetric matrix $[A]^{(f)}$ where $A \in \mathbb{R}^{d \times d}$ the Tridiagonalize protocol (Protocol 30, shown in FIG. 27) computes matrices Q and T such that $T = QAQ^T$ and T is tridiagonal (namely, it only has non-zero elements along the diagonal, subdiagonal and superdiagonal). Similar to the QR factorization algorithm, tridiagonalization is achieved by iteratively applying Householder transformation to portions of A so that any element outside of the tridiagonal region becomes zero. The output of the algorithm is secret shares $[Q]^{(f)}$ and $[T]^{(f)}$ of Q and T, respectively.

Eigendecompose($[A]^{(f)}$) ($[Q]^{(f)}$, $[L]^{(f)}$): On input a secret-shared symmetric matrix $[A]^{(f)}$ where $A \in \mathbb{R}^{d \times d}$ the Eigendecompose protocol (Protocol 31, shown in FIG. 28) applies the QR algorithm for eigendecomposition to A [18]. First, A is transformed using Tridiagonalize to improve the convergence of the subsequent steps. Next, a QR iteration is iteratively applied to the matrix until convergence, where each iteration consists of first QR factorizing the matrix as QR, then updating the matrix as RQ. Repeating this procedure pushes the last diagonal element towards the smallest eigenvalue of A, and upon convergence, the last row and column are deleted to repeat this procedure on the remaining eigenvalues until all of them are obtained. Notably, the eigenvalues revealed by this procedure are already sorted. We use the standard technique of "shifting" the matrix by the last diagonal element before and after each QR factorization to achieve cubic convergence [19]. Instead of testing for convergence, which may leak information, we fix the number of iterations per eigenvalue to a pre-determined value. In our experiments, five QR iterations per eigenvalue were sufficient to obtain accurate results.

Supplementary Note 9: Secure GWAS Protocol

Now we describe how we build a secure and efficient GWAS protocol using the tools described in the previous Supplementary Notes. We work in the crowdsourcing scenario where there are n study participants, denoted $SP_1, \ldots, SP_n$, and m candidate SNPs to be tested for association. For simplicity, we assume each SP owns the data of a single individual. In addition, we assume that the mapping from SNP indices $\{1, \ldots, m\}$ to known SNP identifiers (e.g., rsids) is fixed and public. The individuals' genotypes at each position are of course hidden.

9.1 Input Data

We represent the input data owned by each $SP_i$ as follows:

$g_i^{AA}$, $g_i^{Aa}$, $g_i^{aa} \in \{0, 1\}^m$: $g_{ij}^{AA}$, $g_{ij}^{Aa}$, $g_{ij}^{aa}$ represents whether the $j^{th}$ SNP of $SP_i$ is homozygousreference allele, heterozygous, homozygous-alternative allele, respectively $h_i \in \{0, 1\}$m: $h_{ij}$ represents whether the $j^{th}$ SNP of $SP_i$ is missing $c_i \in \{0, 1\}^l$: covariate features (e.g., age group membership) for $SP_i$ $y_i \in \{0, 1\}$: phenotype of interest (e.g., disease status) for $SP_i$ We let $g_{ij}^{AA} = g_{ij}^{Aa} = g_{ij}^{aa} = 0$ if the genotype is missing (i.e., $h_{ij}=1$). In addition, minor allele dosages $x_i \in \{0, 1, 2\}^m$ are defined as $$x_i := g_i^{Aa} + 2 \cdot g_i^{aa},$$

which can be easily computed from the above data. We use a one-hot encoding of genotypes with $g_i^{AA}$, $g_i^{Aa}$ and $g_i^{aa}$ in order to obtain the separate counts for AA, Aa, and aa for each SNP, which are needed for the quality control procedure (Hardy-Weinberg equilibrium and heterozygosity filters). Note that while computing $x_i$ from $g_i^{AA}$, $g_i^{Aa}$, and $g_i^{aa}$ is easy, the reverse is quite expensive due to the need to perform several equality tests in order to extract each genotype. For a similar reason, missing genotypes are encoded in a separate vector $h_i$ as opposed to using a sentinel value in the genotype vector, which would also require equality tests to extract the information.

While all numbers in our data are binary-valued, it is straightforward to incorporate continuous values using the fixed-point representation (Supplementary Note 5). For instance, we can incorporate imputed genotypes by assigning probabilities (as FP values) to the corresponding, entries in $g^{AA}$, $g^{Aa}$, and $g^{aa}$. Covariate features and the phenotype encodings can also be continuous.

9.2 Initial Data Sharing

During the initial data sharing phase, each $SP_i$ samples a random seed for a PRG and sends it to $CP_1$ over a secure channel. This initializes $PRG_{CP_1,SP_i}$. Next, SP invokes ShareSecretSharedPRG (Protocol 25) to securely share its data with $CP_1$ and $CP_2$. Note that SP transfers data to only $CP_2$, since $CP_1$ non-interactively obtains its shares from $PRG_{CP_1,SP_i}$. After all n SPs have shared their data, $CP_1$ and $CP_2$ execute BeaverPartitionSharedPRG (Protocol 26) on the pooled data to prepare for the main computation phase. While this step requires communication bandwidth equal to the total size of input, it can be aggregated and transferred in a single batch. Thus, at the scale of tens of terabytes (when working with millions of genomes), we expect physically shipping hard drives to be a viable alternative for this step that may be more efficient than online transfer.

At the end of this procedure, the computing parties $CP_1$ and $CP_2$ have access to the shares $[g_i^{AA}]$, $[g_i^{Aa}]$, $[g_i^{aa}]$, $[h_i]$, $[c_i]$, and $[y_i]$, as well as their Beaver partitions for all $i \in \{1, \ldots, n\}$. We also assume CPs have non-interactively computed the minor allele dosages $$[x_i] \leftarrow [g_i^{Aa}] + 2[g_i^{aa}]$$

for all $i \in \{1, \ldots, n\}$. Note that the Beaver partitions of $[x_i]$ can be obtained for free by simply taking a linear combination of the Beaver partitions of $[g_i^{Aa}]$ and $[g_i^{aa}]$.

9.3 Phase 1: Quality Control

The first phase of the main GWAS computation includes common quality control filters for GWAS. In the following, we provide the list of filters we implemented. We write UB and LB to denote an upper bound and a lower bound, respectively, which take on different values for each filter. We assume that these bounds are public and fixed.

Heterozygosity of individual i:

$$LB \leq \frac{\sum_{j=1}^{m} g_{i,j}^{Aa}}{m - \sum_{j=1}^{m} h_{i,j}} < UB$$

Genotype missing rate of individual i:

$$\frac{\sum_{j=1}^{m} h_{ij}}{m} < UB.$$

Minor allele frequency (MAF) of SNP j:

$$LB \leq \frac{\sum_{j=1}^{n} x_{i,j}}{2\left(n - \sum_{j=1}^{n} h_{i,j}\right)} < UB$$

Genotype missing rate of SNP j:

$$\frac{\sum_{j=1}^{n} h_{ij}}{n} < UB$$

Hardy-Weinberg equilibrium (HWE) $\chi^2$ test statistic of SNP j (control cohort-only):

$$\sum_{t \in \{AA, Aa, aa\}} \frac{(O_j^t - E_j^t)^2}{E_j^t} < UB, \text{ where}$$

$$O_j^t := \sum_{i=1}^{n} (1 - y_i) g_{ij}^t, \forall t \in \{AA, Aa, aa\},$$

$$E_j^{AA} := \alpha_j^2 \left(n - \sum_{i=1}^{n} y_i\right)$$

$$E_j^{Aa} := 2\alpha_j (1 - a_j) \left(n - \sum_{i=1}^{n} y_i\right)$$

$$E_j^{aa} := (1 - a_j)^2 \left(n - \sum_{i=1}^{n} y_i\right), \text{ and}$$

$$\alpha_j := \frac{\sum_{i=1}^{n} y_i x_{ij}}{2\left(n - \sum_{i=1}^{n} y_i h_{ij}\right)}.$$

After the CPs compute each of the above quantities over the secret-shared values, they compare each quantity against the (public) thresholds using the LessThan or LessThan Public protocols (Protocols 20 and 21). For all filters except for HWE, we multiply the thresholds with the denominator of the term being compared to avoid invoking the relatively more expensive Divide protocol. This reduces the required computation (other than comparisons) to only affine functions over the secret shares, which can be computed non-interactively.

The HWE filter is the most complex among the quality control filters. First, the numerator and denominator of $\alpha_j$ are separately computed for all j, which is a depth-one computation with an overall output size 2m. Given this result, we use m parallel invocations of Divide to securely compute $\alpha_j$ for all j. After computing the terms $(O_j^t - E_j^t)^2$ and $E_j^t$ via secure multiplications, we use three rounds of m parallel invocations of Divide (one for each $t \in \{AA, Aa, as\}$) to calculate the ratios $(O_j^t - E_j^t)^2 / E_j^t$. Lastly, the results are added for each SNP to obtain the HWE test statistics, which are then compared with the threshold.

After the CPs have securely evaluated each of the above filters, the computing parties compute an AND over the filter outputs. The computing parties then publish their shares and reconstruct the binary inclusion/exclusion status for each individual or SNP (to be revealed also at the conclusion of GWAS along with the association statistics). We perform this step in advance to allow the CPs to directly filter the data sets for the subsequent steps, which cannot be done efficiently if the filtering results are kept hidden. As further explained at the end of this Supplementary Note, this information reveals only a single bit per SNP or per individual and therefore arguably poses a significantly smaller privacy risk than the publication of association statistics.

In practice, researchers may wish to apply some filters first and evaluate the remaining filters over the reduced data. For instance, if the data is pooled from different genotyping platforms, it may be desirable to filter out SNPs with high missing rates first in order to discard non-intersecting loci. In our experiments, we performed quality control in three stages: (i) locus missing rate filter, (ii) individual missing rate and heterozygosity filters, and (iii) locus HWE and MAF filters. The results from each stage was used to reduce the data set before proceeding to the next stage.

We use $n_{qc}$ and $m_{qc}$ to denote the number of individuals and SNPs passing all quality control filters, respectively.

9.4 Phase 2: Population Stratification Analysis

The next phase of the computation is population stratification analysis, where the goal is to obtain the top principal components of the genotype matrix via principal component analysis (PCA) to be included as covariates in the association tests.

SNP Selection.

The current standard practice is to perform PCA over a reduced set of SNPs that are largely independent from one another. Strong correlations among the SNPs, such as those arising from linkage disequilibrium (LD), can distort the PCA results and thus, need to be avoided [20]. In our protocol, we take the simplified approach of keeping only SNPs that are at least 100 Kb apart in order to minimize the impact of LD. Alternative approaches, such as directly computing pairwise correlations and filtering based on them, can be implemented at the expense of efficiency. Since annotations (e.g., genomic position) associated with each SNP in the input data is public, each party independently filters the SNPs according to the same procedure and obtains the reduced matrix non-interactively. Let $m_{pca}$ be the resulting number of SNPs to be used for PCA.

Computing Standardization Parameters.

We denote the filtered input matrix for PCA as $X \in \{0, 1, 2\}^{n_{qc} \times m_{pca}}$, which contains minor allele dosages. The corresponding missingness data is also represented as a matrix $H \in \{0, 1\}^{n_{qc} \times m_{pca}}$.

To standardize the matrix before performing PCA, we follow previous work [21] to compute the mean $\mu_j$ and standard deviation $\sigma_j$ of each SNP j as $$\mu_j := \frac{1 + \sum_{i=1}^{n_{qc}} X_{ij}}{2 + 2\left(n_{qc} - \sum_{i=1}^{n_{qc}} H_{ij}\right)},$$

$$\sigma_j := \sqrt{\mu_j(1-\mu_j)},$$

where the mean is computed over only the observed genotypes. Note $\mu_j$ is smoothed by adding a pseudocount for both allele types to avoid zero standard deviations.

To compute these parameters, the CPs first calculate the denominator and numerator of $\mu_j$ for all j, which are affine functions over the secret shares. Next, $\mu_j$ for all j are computed by $m_{pca}$ parallel invocations of Divide. Then $\mu_j$ and $1-\mu_j$ are securely multiplied and provided as input to $m_{pca}$ parallel invocations of SqrtAndSqrtInverse to obtain $1/\sigma_j$ for all j. We keep $1/\sigma_j$ instead of $\sigma_j$ in order to standardize the genotypes by multiplication, and not by division, as $$\tilde{X}_{ij} := (1/\sigma_j) \cdot (X_{ij} - \mu_j(1-H_{ij})),$$

where $\tilde{X}$ denotes the standardize input matrix for PCA. Note we subtract the mean only where the genotype is not missing.

Implicit Standardization.

Explicitly constructing the standardized matrix $\tilde{X}$ incurs a communication cost that scales quadratically in the dimension of the input data. This is because each element in $\tilde{X}$ corresponds to an output gate that needs to be reconstructed. Instead, we adopt a lazy computation scheme for standardizing X, where every occurrence of $\tilde{X}$ in the following computation is replaced with $$\tilde{X} \mapsto (X-HM)\Sigma^{-1},$$

with $$M := \begin{bmatrix} \mu_1 & & 0 \\ & \ddots & \\ 0 & & \mu_{m_{pca}} \end{bmatrix} \text{ and } \Sigma^{-1} := \begin{bmatrix} 1/\sigma_1 & & 0 \\ & \ddots & \\ 0 & & 1/\sigma_{m_{pca}} \end{bmatrix}.$$

In our PCA protocol, $\tilde{X}$ only appears in products where the resulting matrix is either tall-and-skinny or short-and-fat with the smaller dimension being a very small constant. After writing out each multiplication with the above substitution, we observe that we can evaluate matrix products involving $\tilde{X}$ in one of two different ways:

$$A\tilde{X} \mapsto A(X-HM)\Sigma^{-1} \mapsto (AX)\Sigma^{-1} - ((AH)M)\Sigma^{-1},$$

$$\tilde{X}B \mapsto (X-HM)\Sigma^{-1}B \mapsto X(\Sigma^{-1}B) - (M(\Sigma^{-1}B)),$$

where A is short-and-fat and B is tall-and-skinny. This way, each matrix multiplication involving X results in an intermediary matrix that has at least one very small dimension.

This means that the overall communication bandwidth scales linear in $m_{pca}$ and $n_{qc}$. Note that the computation results we obtain via this procedure is equivalent to directly working with $\tilde{X}$.

Randomized PCA.

Given the standardized genotype matrix $\tilde{X}$ (which is never explicitly constructed), the final step of Phase 2 is to securely perform PCA to obtain the top principal components (PCs) of the columns of $\tilde{X}$ (i.e., the left singular vectors of $\tilde{X}$). These principal component represent broad genetic patterns in the data that are thought to be indicative of population structure. Since PCA is a complex, iterative algorithm, directly performing PCA on $\tilde{X}$ is infeasible due to the large input dimensions involved in realistic GWAS scenarios. To illustrate, if we were to naively invoke Eigendecompose (Protocol 31) on the covariance matrix $\tilde{X}\tilde{X}^T$ to perform PCA, we would need to QR factorize a $n_{qc} \times n_{qc}$ matrix a multiple of $n_{qc}$ times. As a result, communication scales cubically in $n_{qc}$, which is infeasible. In this work, we instead use an efficient randomized algorithm for matrix factorization based on the techniques of [22].

We give a high-level sketch of the RandomizedPCA (Protocol 32, shown in FIG. 29) subroutine that we use. First, we obtain a matrix $Q \in \mathbb{R}^{m_{pca} \times (\psi+\alpha)}$ whose orthonormal columns satisfy $$\tilde{X}QQ^T \approx \tilde{X}.$$

Note $\psi$ is the desired number of top principal components, and $\alpha$ is a small oversampling parameter (set to 10 in our experiments) used to increase the stability and accuracy of the algorithm. Also, $\psi+\alpha \ll m_{pca}$. Such Q can be obtained by projecting $\tilde{X}$ onto a random subspace and extracting its orthonormal bases via QR factorization. We additionally apply the power iteration procedure to improve the approximation quality, as described in [22]. More precisely, $$Q \Sigma \mathbb{R}^{m_{pca} \times (\psi+\alpha)} := \text{Orthonormal bases of the row space of } \Pi \tilde{X}(\tilde{X}^T\tilde{X})^\rho,$$

where $\Pi \in \mathbb{R}^{(\psi+\alpha) \times m_{pca}}$ is a random projection matrix publicly known by all CPs (e.g., CountSketch [23], which is our method of choice), and $\rho$ is the number of power iterations (set to 20 in our experiments). To reduce communication, we derive $\Pi$ using a PRG, and have each of the computing parties generate it locally (from a globally shared PRG seed).

Next, we perform $\psi$-truncated singular value decomposition (SVD) on the matrix $Z := \tilde{X}Q \approx U_\psi \Sigma_\psi V_\psi^T$, where $U_\psi \Sigma_\psi (QV_\psi)^T$ is the IP-truncated SVD of $\tilde{X}QQ^T$, which is approximately $\tilde{X}$. Thus, $U_\psi$ approximates the desired left singular vectors of $\tilde{X}$.

In our adaptation of this algorithm, we take a step further and compute the SVD of Z by the eigendecomposition of an even smaller $(\psi+\alpha) \times (\psi+\alpha)$ matrix $$Z^T Z = Q'L'(Q')^T$$

with eigenvectors Q' and a diagonal L' containing the eigenvalues. Assuming the eigenvalues are sorted, we have $$Q'_{:,:\psi} = V_\psi \text{ and } L'_{:\psi,:\psi} = \Sigma_\psi^2.$$

Thus, we can recover $U_\psi$ given the eigendecomposition of $Z^T Z$ by computing $$U_\psi = ZQ'_{:,:\psi}(L'_{:\psi,:\psi})^{-1/2},$$

which concludes our algorithm.

Overall, our modified algorithm reduces the original problem of factorizing a large $n_{qc} \times m_{pca}$ matrix $\tilde{X}$ to an eigendecomposition of a tiny $(\psi+\alpha) \times (\psi+\alpha)$ matrix $Z^T Z$ whose dimensions only slightly exceed the number of top principal components we are interested in. Notably, the size of this subproblem does not depend on $n_{qc}$ or $m_{pca}$, and in typical GWAS scenarios, we expect $\psi+\alpha \leq 20$.

9.5 Phase 3: Association Tests

The final phase of GWAS is computing the association statistic for each SNP, which intuitively quantifies how informative each SNP is for predicting the phenotype of interest. In this work, we compute the $\chi^2$ statistics of Cochran-Armitage (CA) trend test. We use a generalized version of the CA test described in [21] that additionally corrects for covariates, which in our case, includes those provided in the input (e.g., age) as well as the principal components from Phase 2. Correction is performed by regressing out the covariate features from each genotype and phenotype vectors before computing the test statistic.

Given the secret shares of principal components $U_\psi \Sigma \in \mathbb{R}^{n_{qc} \times \psi}$ and representing $l$ input covariate features as a matrix $C \in \{0, 1\}^{n_{qc} \times l}$, the first step is to find the orthonormal bases of the subspace spanned by both. This is achieved by concatenating the two matrices and invoking QRFactorizeRectangle. We denote the resulting bases of the covariate subspace $Q \in \mathbb{R}^{n_{qc} \times (\psi+l)}$.

Let $x_j \in \{0, 1, 2\}^{n_{qc}}$ denote the genotype vector (minor allele dosages) of SNP $j$ and $y \in \{0, 1\}^{n_{qc}}$ be the phenotype vector of interest. Both vectors are first corrected for covariates by projecting them onto the null space of $Q$:

$$\hat{x}_j := (I_{n_{qc} \times n_{qc}} - QQ^T) x_j,$$

$$\hat{y} := (I_{n_{qc} \times n_{qc}} - QQ^T) y.$$

Next, the CA statistic is computed as the squared Pearson correlation coefficient between the corrected vectors $\hat{x}_j$ and $\hat{y}$, which can be expressed as $$r_j^2 := \frac{\left(n_{qc} \sum_i \hat{x}_{ji} \hat{y}_i - \sum_i \hat{x}_{ji} \sum_i \hat{y}_i\right)^2}{[n_{qc} \sum_i \hat{x}_{ji}^2 - (\sum_i \hat{x}_{ij})^2]} \quad (4)$$
$$[n_{qc} \sum_i \hat{y}_i^2 - (\sum_i \hat{y}_i)^2]$$

We include missing genotypes as zeros to maintain consistency with the PCA step. Note only SNPs and individuals with low missing rates are considered here as a result of Phase 1, so the impact of missing data is minimal.

Efficiently computing the above expression for $r_j^2$ every SNP is not trivial. For instance, explicitly constructing the corrected genotypes $\hat{x}_j$ for all SNPs should be avoided, as it would incur a communication cost equal to the size of the genotype matrix, which is naturally quadratic in the input dimensions. Here, we provide an alternative formulation for computing the CA statistics that requires only linear communication bandwidth.

First, observe that $\hat{y}$ can be explicitly computed, since it is only a single vector (unlike $\hat{x}_j$, which exists for each $j \in \{1, \ldots, m_{qc}\}$). We evaluate $\hat{y}$ as $y - Q(Q^T y)$ to ensure that all intermediary results have linear size. Once the secret shares of $\hat{y}$ are obtained, they are Beaver partitioned to use in future computation.

Next, note that computing the following summary statistics are sufficient for computing the CA statistics:

$$s_j^x := \Sigma_i \hat{x}_{ji}, \forall j \in \{1, \ldots, m_{qc}\},$$

$$s_j^{xx} := \Sigma_i \hat{x}_{ji}^2, \forall j \in \{1, \ldots, m_{qc}\},$$

$$s_j^{xy} := \Sigma_i \hat{x}_{ji} \hat{y}_i, \forall j \in \{1, \ldots, m_{qc}\},$$

$$s^y := \Sigma_i \hat{y}_i,$$

$$s^{yy} := \Sigma_i \hat{y}_i^2.$$

We can directly calculate $s^y$ and $s^{yy}$ from the secret shares of $\hat{y}$. In addition, note $s_j^{xy}$ can be computed using the uncorrected $x_j$, since taking the inner product with y, which is already projected onto the null space of Q, ensures that the component of x residing in the covariate space will be ignored. Thus, we compute $s_j^{xy}$ as $\Sigma_i x_{ji} \hat{y}_i$ for all j, which is a depth-one circuit with output size $m_{qc}$.

It remains to show how to compute $s_j^x$ and $s_j^{xx}$. Let X be an $n_{qc} \times m_{qc}$ matrix constructed by horizontally concatenating $x_j$ for all j (i.e., $x_j$ is placed in the j-th column of X). We express the required computation in terms of matrices as $$s^x = 1_{n_{qc}}^T (I_{n_{qc} \times n_{qc}} - QQ^T) X$$
$$= 1_{n_{qc}}^T X - (1_{n_{qc}}^T QQ^T) X,$$
$$s^{xx} = \text{diag}(X^T (I_{n_{qc} \times n_{qc}} - QQ^T) X)$$
$$= \text{diag}(X^T X) - \text{diag}((Q^T X)^T (Q^T X)),$$

where we write $1_{n_{qc}}$ to denote the $n_{qc}$-dimensional vector consisting of all ones. Next, we simplify the computation by defining $$u := QQ^T 1_{n_{qc}},$$

$$B := Q^T X,$$

both of which have size linear in the input dimensions and thus, can be evaluated without incurring a quadratic communication cost. The remainder of the computation is computed as $$s^x = 1_{n_{qc}}^T X - u^T X,$$

$$s^{xx} = \text{diag}(X^T X) - \text{diag}(B^T B),$$

which are depth-one circuits with output size only $m_{qc}$ each.

After all of the summary statistics have been computed, the CA statistics can be obtained via secure multiplications and invocations of SqrtAndSqrtInverse (or Divide) over length-$m_{qc}$ vectors in accordance with Eq. (4). We formally describe our procedure CochranArmitage for efficiently computing CA statistics in Protocol 33, shown in FIG. 30.

9.6 Output Reconstruction

At the end of our GWAS protocol, the computing parties $CP_1$ and $CP_2$ reveal their individual shares of the association statistics via ReconstructSecret (Protocol 2) and publish the results. In addition, they publish the results of the quality control filters from Phase 1 to facilitate the interpretation of the released GWAS statistics. For instance, one may wish to distinguish whether a particular SNP is deemed insignificant based on the association test or simply excluded from the analysis due to poor quality.

9.7 Precomputation

None of the computation by $CP_0$ in our overall protocol for GWAS depends on input values, and thus can be performed entirely in advance in a preprocessing phase. The one exception is the filtering step in Phase 1. The auxiliary computing party $CP_0$ needs the results of the filtering step to obtain the data dimensions used in the subsequent computation and use the appropriate Beaver partitions obtained during the initial data sharing phase. Thus, $CP_0$ performs the precomputation in stages: once before initial data sharing and once after each filtering stage in Phase 1. Note $CP_0$ can remain offline for the entirety of Phases 2 and 3.

9.8 Overall Complexity

To summarize, excluding the initial data sharing phase, our secure GWAS protocol requires communication complexity for both precomputation and online computation phases only linear in number of individuals and number of SNPs in the data. This is enabled by the following technical contributions:

- our generalized Beaver partitioning method, which allows for efficient evaluations of depth-one circuits (e.g., matrix multiplication) and effective reuse of Beaver partitioned data for multiple operations (Supplementary Note 3),
- our use of shared random streams (PRGs) to enable Beaver partitioning without any communication between $CP_0$ and the other computing parties (Supplementary Note 7),
- our use of a randomized PCA algorithm for population stratification analysis, which reduced a large matrix factorization problem to a tiny constant-sized matrix (Section 9.4), and
- our careful restructuring of the required computations to ensure that all intermediary results have linear sizes (e.g., Section 9.5).

9.9 Privacy Guarantees

The security of our end-to-end GWAS protocol reduces to the security of the underlying building blocks we use. More precisely, the view of each computing party in each of the subprotocols consist of uniformly random values (or values that are statistically close to uniform). As explained in the security section of Supplementary Note 5, we choose a large enough statistical security parameter κ to achieve an overall statistical distance (or equivalently, an adversary's distinguishing advantage) $<2^{-30}$ between each computing party's view and an ideal distribution where all of the messages exchanged in the protocol consist of uniformly random values. This ensures no information about the underlying input genotypes and phenotypes is leaked to the computing parties during the computation.

Therefore, the only information about the input that is "leaked" are the publicly-revealed GWAS results computed by our protocol, which include the association test statistics and the output of the quality control filters. The quality control results consist of binary-valued inclusion/exclusion status of each individual or SNP, and in realistic GWAS scenarios, do not pose a significant privacy risk for the participants. For example, our per-individual filter reveals only whether a study participant had poor genotyping (too many missing genotypes) or has too many or too few heterozygous sites across the whole genome. The link between such high-level and limited information (a single bit) and the raw genotypes at individual SNPs is extremely tenuous. On the other hand, the association results arguably contain more information about the raw genotypes. We can compose our protocols with techniques based on differential privacy [24] (as a post-processing step) to assuage these concerns [25, 26]. However, at the scale of a million individuals or more, we expect the risk of releasing such summary statistics to be considerably small.

Supplementary Note 10: Towards Stronger Security Guarantees

10.1 Relaxing the No-Collusion Assumption

The security of our protocol assumes the computing parties do not collude with each other. In settings where it is difficult to justify this assumption, we can introduce additional computing parties to ensure tolerance against a bounded number of collusions in the online (namely, input-dependent) phase of the computation. Note that we still need to assume a semi-honest (and non-colluding) $CP_0$ in the precomputation phase. In particular, instead of secret sharing the data between two main computing parties $CP_1$ and $CP_2$, we can distribute the private input x across n such entities $CP_1, \ldots, CP_n$ such that $CP_i$ for $1 \le i \le n-1$ holds an independent and uniformly random number as its share $([x]_i = r_i)$, and $CP_n$ holds $[x]_n = x - \Sigma_{i=1}^{n-1} r_i$. Analogous to the two-party case, we have the property that $\Sigma_2[x]_i = x$. Here, as long as there exists a single honest party that does not collude, x remains perfectly hidden. Our building block protocols can be easily extended to handle secret shares over more than two parties. In the extended version of our Beaver partitioning approach, $CP_0$ still obtains the blinding factors in the clear, so we require that $CP_0$ does not collude with the other parties. In summary, the relaxed security assumption in the (n+1)-party setting (including $CP_0$) is that $CP_0$ and at least one other CP are honest (i.e., do not collude with the other parties). The main benefit of this setup is that the protocol is able to tolerate collusion among the other n-1 computing parties in the online phase of the computation. As a tradeoff, however, the overall communication scales linearly with the number of computing parties involved.

10.2 Handling Active Adversaries

Our protocol provides security against semi-honest adversaries, namely adversaries that honestly follow the protocol execution, but may subsequently try to learn additional information about other parties' private inputs. In some scenarios, it may be necessary to ensure security even against malicious or active adversaries. For instance, if one of the computing parties is compromised or subverted during the computation, then it may deviate from the protocol specification in order to learn additional information about the participants' genomes.

In the last few years, an elegant line of work [3, 4, 6, 27] has introduced secret-sharing-based multiparty computation protocols with an optimal online phase which provides security against active (i.e., malicious) adversaries that may deviate from the protocol execution. The same techniques can be applied to our protocol to achieve security against active adversaries in the online phase of the computation. We describe the main idea used in the SPDZ protocol here [3] and how to extend it to our protocol. For simplicity, we describe our extension in the two-party setting, but everything generalizes naturally to the multiparty setting.

Secret-Shared Authenticated Values.

First, in the precomputation phase of the protocol, $CP_0$ samples a random field element $$\alpha \xleftarrow{R} \mathbb{Z}_q$$

and secret shares it with the computing parties $CP_1$ and $CP_2$. The secret element a serves as a secret key for an information-theoretic message authentication code (MAC) that is used to authenticate the secret-shared data and validate the outputs of the computation. Then, in the online phase of the computation, an authenticated secret-sharing of a value $x \in \mathbb{Z}_q$ is represented as follows:

$$[x] := \langle (\delta, [x]_1, [\alpha(x+\delta)]_1), (\delta, [x]_2, [\alpha(x+\delta)]_2) \rangle,$$

where $\delta \in \mathbb{Z}_q$ is some public scalar (known to all parties). At a high level, each computing party possesses a share of the input x as well as a share of the MAC αx on x.

Computing on Authenticated Shares.

It is straightforward to see that $$[x]+[y]=[x+y] \text{ and } a\cdot[x]=[ax] \text{ and } [x]+a=[x+a], \quad (5)$$

where $[x]+[y]$ denotes component-wise addition, $a\cdot[x]$ denotes component-wise scalar multiplication, and $$[x]+a := \langle (\delta-a,[x]_1+a,[\alpha(x+\delta)]_1),(\delta-\alpha,[x]_2,[\alpha(x+\delta)]_2) \rangle.$$

Thus, computing linear functions on secret-shared authenticated values is almost identical to computing linear functions of normal secret-shared values (Supplementary Note 2). Multiplication relies on Beaver multiplication triples as before. In particular, given two secret-shared authenticated values $[x]$, $[y]$, and an authenticated sharing of a multiplication triple $([a], [b], [c])$ where $c=ab$, the parties can compute an authenticated secret-sharing of the product $[xy]$. Specifically, the parties first reveal the values $x-a$ and $y-b$ (but not their MACs). Then, they compute $$[xy]:=(x-a)(y-b)+(x-a)[b]+(y-b)[a]+[c],$$

exactly as in Protocol 7 using the linear relations defined in Eq. (5). Moreover, our generalization of Beaver multiplication triples (Supplementary Note 3) directly applies to reduce the online communication costs of computing on authenticated values as our generalized Beaver partitioning method only requires computing linear relations over secret-shared authenticated values.

Validating the MAC. At the end of the computation, all of the computing parties have an authenticated secret-sharing $[y]$ of the output $y$. In the semi-honest version of the protocol, the computing parties would simply publish their shares of the output, and reconstruct the final output of the computation. In the actively-secure protocol, all of the parties first validate the MAC on the output and only if the MAC verification succeeds do the (honest) parties publish their shares. This step of the computation is identical to the output verification step in the SPDZ protocol described in [3, FIG. 1], and we refer the reader to there for the full description. Thus, we can apply the SPDZ techniques to provide active security in the online phase of the computation. The additional computational overhead needed to achieve active security in the online phase of the protocol is essentially a factor of two (since each party has to perform computations on both the secret-shared values as well as their MACs). The communication complexity in the online phase is unchanged since only the blinded inputs (and not their MACs) need to be revealed for each Beaver partitioning operation. The protocol also scales naturally to more than two parties (for instance, if we wanted to additionally apply the transformation in the previous section).

Initial Data Sharing.

To leverage the SPDZ techniques for active security in the online setting, we assumed that each of the computing parties have secret-shared authenticated values (rather than vanilla secret-shared values). Thus, we need to adapt the initial data sharing procedure (between the study participants SP and the computing parties CP) so that the computing parties possess authenticated shares of the participants' input. We achieve this using a simple adaptation of the SPDZ input-sharing procedure. To simplify the description, assume for now that each $SP_i$ contributes just a single input $x_i \in \mathbb{Z}_q$. The protocol naturally generalizes to the setting where each study participant contributes a vector of field elements. During the pre-computation phase, for each study participant $SP_i$, the auxiliary computing party $CP_0$ secret-shares a random value $[r_i]$ where $$r_i \xleftarrow{R} \mathbb{Z}_q$$

with each of the computing parties. To contribute its input to the study, $SP_i$ first interacts with $CP_0$ to obtain the blinding factor $r_i$. It then sends the blinded value $x_i - r_i$ to each of the computing parties. Since the computing parties possess an authenticated sharing of $[r_i]$, they can locally compute an authenticated secret-sharing of $[r_i]+(x_i-r_i)=[x_i]$, exactly as required for the online protocol. Note that here, we can use the same trick from Supplementary Note 7 and have $CP_0$ derive the randomness $r_i$ from a PRG. Then, the total communication between $CP_0$ and each $SP_i$ consists of only a single (short) PRG seed. Compared to the semi-honest protocol, there is increased communication between $CP_0$ and one of the computing parties $CP_i$ since $CP_0$ needs to send over a share of $r_i$ (the other shares can also be derived from a PRG as before). The communication from the study participant to the computing parties also increases, since it now needs to broadcast $x_i - r_i$ to all computing parties. However, the resulting protocol provides stronger security in the online setting.

Security Discussion.

By relying on the SPDZ protocol for the online phase of the computation, our online protocol is secure against even if one of the computing parties is actively malicious. More generally, in the extended setting with additional computing parties, the online phase provides security against an active adversary that corrupts all but a single computing party. However, the resulting protocol still relies on a semi-honest precomputation phase. In other words, security of the online phase relies on correctly-generated authenticated secret-shared (generalized) Beaver triples, as well as $CP_0$ not colluding with any of the computing parties in the online phase. While this may seem like a strong assumption, it is important to keep in mind that the precomputation phase is input-independent, and moreover, we only need $CP_0$ to be a "trusted dealer" (as opposed to a trusted party that possibly sees private inputs). More precisely, $CP_0$ can be modeled as a "write-only" party since we can structure the protocol such that it never needs to receive any message from another party during the protocol execution. This means that an adversary who only corrupts $CP_0$ does not compromise privacy of any of the study participants' inputs.

Supplementary Note 11: Other Cryptographic Frameworks

Here, we provide a ballpark assessment of the applicability of other existing cryptographic frameworks for secure computation, namely homomorphic encryption (HE) [28] and garbled circuits (GC) [12], for securely evaluating large-scale GWAS. HE refers to an encryption scheme that allows certain types of computation to be performed over the private input by manipulating the ciphertexts without decrypting them. Unlike our multiparty solution, HE computation can be carried out by a single party, albeit with greater computational overhead. The current state-of-the-art HE schemes can evaluate a single multiplication in 0.1 seconds [29]. Given that the number of multiplication gates in just the PCA computation is loosely lower-bounded by the number of elements in the genotype matrix, existing HE solutions already require over 30 years of computation to evaluate PCA over a matrix of one million individuals and a reduced set of 10K SNPs, which is clearly infeasible.

On the other hand, Yao's GC protocol is a two-party protocol that enables secure evaluation of arbitrary functionalities (represented as Boolean circuits). In Yao's protocol, one of the parties (i.e., the "garbler") takes the Boolean circuit, and encrypts and permutes (i.e., "garbles") the circuit. The other party (i.e., the "evaluator") is then able to evaluate the garbled circuit and learn the final output, but nothing else about the other party's input. While Yao's protocol require just two rounds of communication for arbitrary computation, the size of the Boolean circuit needed to evaluate our large-scale GWAS computation is prohibitively large. This is due to the fact that GWAS evaluation consists primarily of arithmetic operations. Converting an arithmetic circuit to a Boolean circuit incurs a non-negligible overhead, which is typically linear or quadratic in the bit-length of the values. For example, assuming the same number of bits (60) are used to represent a single number as in our method (using the fixed-point representation), a pairwise multiplication using the Karatsuba algorithm requires roughly 600 AND gates. At 128-bits of security, we require 32 bytes to represent a single AND gate in a garbled circuit [30]. Thus, a single pairwise multiplication requires 20.6 KB of communication. Using the same lower-bound for the number of multiplication gates as in our analysis of HE, communicating a garbled circuit for performing PCA requires roughly 190 PB for a million individuals and 10K SNPs. This is well beyond the feasible realm.

Note our estimates above are very loose lower-bounds, and thus we expect the computational burden of the current state-of-the-art HE and GC frameworks for large-scale GWAS to be even greater in practice.

Supplementary Note 12: Towards Logistic Regression Analysis

In case-control studies where the phenotype of interest is binary (e.g., disease status), logistic regression analysis is often used in conjunction with Cochran-Armitage (CA) trend tests to quantify the candidate SNP's impact on phenotypic odds ratio (e.g., disease risk). To this end, one typically trains a logistic regression model for each SNP that predicts the phenotype based on the SNP's minor allele dosage as well as other covariate features, such as age, gender, and population weights (captured by principal components). The estimated model parameter for minor allele dosage is interpreted as the marginal effect of the SNP on the odds ratio and is often reported with top GWAS hits.

Secure evaluation of logistic regression is very challenging. Unlike CA tests, where the required computation can be formulated as a few rounds of matrix multiplications and division (see Protocol 33), training a logistic regression model not only requires frequent evaluation of the sigmoid function (highly nonlinear), but also relies on iterative optimization techniques for parameter estimation (e.g., stochastic gradient descent). These aspects greatly increase the complexity of the overall computation. To illustrate, a recent work based on homomorphic encryption reported a runtime of 30 seconds for a single evaluation of the sigmoid function [31]. Applying this technique to GWAS with a million individuals would result in a runtime of almost a year for a single pass through the data set, which is clearly not feasible considering that gradient descent methods typically require many passes through the data.

The efficient secure computation techniques we introduced for GWAS offer a more tractable approach for performing logistic regression at large-scale. Notably, we approximate the sigmoid function (more precisely, its logarithm: $-\log(1+\exp(-x))$) as a piecewise-linear function (with 64 segments to ensure high accuracy). Given a private input, we perform secure binary search of depth six—implemented as a sequence of secure comparisons (Protocol 21)—to determine which segment the input belongs to. Then, we retrieve the coefficients of the corresponding linear function via secure table lookup (Protocol 11). Given these coefficients, the (approximate) output of sigmoid and its derivative can be easily computed, non-interactively.

The rest of the computation in logistic regression can be handled by our MPC framework in a straightforward manner. Importantly, our novel generalization of Beaver multiplication triples (Supplementary Note 3) is critical for obtaining an efficient protocol for the stochastic gradient descent (SGD) algorithm, which heavily depends on matrix multiplications and displays high data reuse patterns. In particular, a nave approach using Beaver multiplication triples would freshly blind/Beaver-partition the input matrix for every iteration, which is infeasible at our scale; with our technique, Beaver-partitioning is performed only once.

Even with our advances, logistic regression imposes an overwhelming computational burden when applied to hundreds of thousands of SNPs in a typical GWAS data set. In practice, we suggest a two-step approach where CA tests are first used to narrow down the set of candidate SNPs with tangible association signals and we consider only the chosen SNPs in a subsequent logistic regression analysis.

We implemented logistic regression in our secure MPC framework and tested it on our benchmark lung cancer data set. Our protocol accurately computed the odds ratios for 100 SNPs within a day of runtime (Supplementary FIG. 2). Extrapolating to a million-individual data set, we expect a runtime of approximately three months for computing the odds ratios for 100 SNPs. Note that the actual runtime may be substantial shorter as the number of passes through the data ("epochs") until the convergence of SGD may be smaller for larger data sets given that our models have only few predictive features. While further improvements are needed to achieve genome-wide scalability of secure logistic regression, our results suggest that obtaining the odds ratios for a small subset of SNPs is currently feasible as newly enabled by our techniques.

Recently, Mohassel and Zhang also introduced an implementation of privacy-preserving logistic regression by combining techniques from secret-sharing-based MPC with garbled circuits [32]. Although they show that their protocol achieves practical runtimes for data sets containing up to a million training instances, their improved scalability comes at the expense of accuracy. In particular, a key factor that contributed to the scalability of their protocol is their use of a coarse approximation of the sigmoid function (namely, as a piecewise linear function with three segments). While this approximation may suffice for obtaining competitive predictive performance (the focus of their work) for certain data sets, it is too inaccurate in our GWAS setting where the goal is to obtain an accurate estimate of the model parameters. Moreover, even with their coarse approximation, training a separate logistic regression model for each of the hundreds of thousands of SNPs in a typical GWAS data set still requires several years of computation. We also observed that, using our implementation, we can achieve runtimes that are comparable to their approach by reducing the quality of our approximation of the sigmoid function and taking a similar number of passes through the data set for SGD. This further illustrates the challenges of achieving a practical solution for genome-wide logistic regression analysis under secure computation frameworks.

SUPPLEMENTARY REFERENCES

[1] Ben-Or, M., Goldwasser, S. & Wigderson, A. Completeness theorems for non-cryptographic fault-tolerant distributed computation. In *STOC*, 1-10 (1988).

[2] Bendlin, R., Damgård, I., Orlandi, C. & Zakarias, S. Semi-homomorphic encryption and multiparty computation. In *EUROCRYPT*, 169-188 (2011).

[3] Damgård, I., Pastro, V., Smart, N. P. & Zakarias, S. Multiparty computation from somewhat homomorphic encryption. In *CRYPTO*, 643-662 (2012).

[4] Damgård, I. et al. Practical covertly secure MPC for dishonest majority—or: Breaking the SPDZ limits. In *ESORICS*, 1-18 (2013).

[5] Nielsen, J. B., Nordholt, P. S., Orlandi, C. & Burra, S. S. A new approach to practical active-secure two-party computation. In *CRYPTO*, 681-700 (2012).

[6] Keller, M., Orsini, E. & Scholl, P. MASCOT: faster malicious arithmetic secure computation with oblivious transfer. In *ACM CCS*, 830-842 (2016).

[7] Beaver, D. Efficient multiparty protocols using circuit randomization. In *CRYPTO*, 420-432 (1991).

[8] Kamara, S., Mohassel, P. & Raykova, M. Outsourcing multi-party computation. *IACR Cryptology ePrint Archive* 272 (2011).

[9] Bogdanov, D., Laur, S. & Willemson, J. Sharemind: A framework for fast privacy-preserving computations. In *ESORICS*, 192-206 (2008).

[10] Chandra, A., Fortune, S. & Lipton, R. Lower bounds for constant depth circuits for prefix problems. *Automata, Languages and Programming* 109-117 (1983).

[11] Damgard, I., Fitzi, M., Kiltz, E., Nielsen, J. B. & Toft, T. Unconditionally Secure Constant-Rounds Multi-party Computation for Equality, Comparison, Bits and Exponentiation. In *Theory of Cryptography*, 285-304 (Springer, 2006).

[12] Yao, A. C. Protocols for secure computations (extended abstract). In *FOCS*, 160-164 (1982).

[13] Catrina, O. & Saxena, A. Secure computation with fixed-point numbers. In *International Conference on Financial Cryptography and Data Security*, 35-50 (Springer, 2010).

[14] Goldreich, O. *The Foundations of Cryptography-Volume 1, Basic Techniques* (Cambridge University Press, 2001).

[15] Nishide, T. & Ohta, K. Multiparty computation for interval, equality, and comparison without bit-decomposition protocol. In *International Workshop on Public Key Cryptography*, 343-360 (Springer, 2007).

[16] Markstein, P. Software division and square root using goldschmidts algorithms. In *Proceedings of the 6th Conference on Real Numbers and Computers*, vol. 123, 146-157 (2004).

[17] Dahl, M., Ning, C. & Toft, T. On secure two-party integer division. In *International Conference on Financial Cryptography and Data Security*, 164-178 (2012).

[18] Ortega, J. M. & Kaiser, H. F. The llt and qr methods for symmetric tridiagonal matrices. *The Computer Journal* 6, 99-101 (1963).

[19] Wang, T.-L. Convergence of the tridiagonal qr algorithm. *Linear Algebra and Its Applications* 322, 1-17 (2001).

[20] Laurie, C. C. et al. Quality control and quality assurance in genotypic data for genome-wide association studies. *Genetic Epidemiology* 34, 591-602 (2010).

[21] Price, A. L. et al. Principal components analysis corrects for stratification in genome-wide association studies. *Nature Genetics* 38, 904-909 (2006).

[22] Halko, N., Martinsson, P.-G. & Tropp, J. A. Finding structure with randomness: Probabilistic algorithms for constructing approximate matrix decompositions. *SIAM Review* 53, 217-288 (2011).

[23] Charikar, M., Chen, K. & Farach-Colton, M. Finding frequent items in data streams. *Theoretical Computer Science* 312, 3-15 (2004).

[24] Dwork, C. Differential privacy. In *ICALP*, 1-12 (2006).

[25] Simmons, S., Sahinalp, C. & Berger, B. Enabling Privacy-Preserving GWASs in Heterogeneous Human Populations. *Cell Systems* 3, 54-61 (2016).

[26] Simmons, S. & Berger, B. Realizing Privacy Preserving Genome-Wide Association Studies. *Bioinformatics* 32, 1293-1300 (2016).

[27] Damgård, I. & Nielsen, J. Scalable and unconditionally secure multiparty computation. *Advances in Cryptology-CRYPTO 2007* 572-590 (2007).

[28] Gentry, C. Fully Homomorphic Encryption Using Ideal Lattices. *STOC* (2009).

[29] Chillotti, I., Gama, N., Georgieva, M. & Izabachene, M. Faster fully homomorphic encryption: Bootstrapping in less than 0.1 seconds. *ASIACRYPT* 10031, 3-33 (2016).

[30] Zahur, S., Rosulek, M. & Evans, D. Two halves make a whole: Reducing data transfer in garbled circuits using half gates. In *EUROCRYPT*, 220-250 (2015).

[31] Bos, J. W., Lauter, K. & Naehrig, M. Private predictive analysis on encrypted medical data. *Journal of Biomedical Informatics* 50, 234-243 (2014).

[32] Mohassel, P. & Zhang, Y. Secureml: A system for scalable privacy-preserving machine learning. *Cryptology ePrint Archive* 396 (2017).

[33] Seiler, M. C. & Seiler, F. A. Numerical recipes in c: the art of scientific computing. *Risk Analysis* 9, 415-416 (1989).

ENABLING TECHNOLOGIES

One or more functions of the computing platform of this disclosure may be implemented in a cloud-based architecture. As is well-known, cloud computing is a model of service delivery for enabling on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. Available services models that may be leveraged in whole or in part include: Software as a Service (SaaS) (the provider's applications running on cloud infrastructure); Platform as a service (PaaS) (the customer deploys applications that may be created using provider tools onto the cloud infrastructure); Infrastructure as a Service (IaaS) (customer provisions its own processing, storage, networks and other computing resources and can deploy and run operating systems and applications).

The platform may comprise co-located hardware and software resources, or resources that are physically, logically, virtually and/or geographically distinct. Communication networks used to communicate to and from the platform services may be packet-based, non-packet based, and secure or non-secure, or some combination thereof.

More generally, the techniques described herein are provided using a set of one or more computing-related entities (systems, machines, processes, programs, libraries, functions, or the like) that together facilitate or provide the described functionality described above. In a typical implementation, a representative machine on which the software executes comprises commodity hardware, an operating system, an application runtime environment, and a set of applications or processes and associated data, that provide the functionality of a given system or subsystem. As described, the functionality may be implemented in a stand-alone machine, or across a distributed set of machines.

A computing entity herein receives the secretly-shared data from a client device, which may even be an end user device. Thus for example, but without limitation, a client device is a mobile device, such as a smartphone, tablet, or wearable computing device. Such a device comprises a CPU (central processing unit), computer memory, such as RAM, and a drive. The device software includes an operating system (e.g., Google® Android™, or the like), and generic support applications and utilities.

The underlying network transport may be any communication medium including, without limitation, packet-based, cellular, wireless, Wi-Fi, small cell, and combinations thereof.

Each above-described process (e.g., each of the protocols set forth in the drawings) preferably is implemented in computer software as a set of computer program instructions executable in one or more processors, as a special-purpose machine.

Representative machines on which the subject matter herein is provided may be hardware processor-based computers running an operating system and one or more applications to carry out the described functionality.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

While the disclosed subject matter has been described in the context of a method or process, the subject matter also relates to apparatus for performing the operations herein. This apparatus may be a particular machine that is specially constructed for the required purposes, or it may comprise a computer otherwise selectively activated or reconfigured by a computer program stored in the computer. Such a computer program may be stored in a computer readable storage medium, such as, but is not limited to, any type of disk including an optical disk, a CDROM, and a magnetic-optical disk, a read-only memory (ROM), a random access memory (RAM), a magnetic or optical card, or any type of media suitable for storing electronic instructions, and each coupled to a computer system bus.

A given implementation of the computing platform is software that executes on a hardware platform running an operating system, such as Linux. A machine implementing the techniques herein comprises a hardware processor, and non-transitory computer memory holding computer program instructions that are executed by the processor to perform the above-described methods.

Communications herein (e.g., secret sharing of data, sharing of PRGs, etc.) preferably take place over secure connections. For machine-to-machine communications over a network, information typically is communicated over SSL/TLS links, or using any other protocol, although if significant trust is in place (e.g., machines being operated in a secure environment, or between entities that have a trust relationship, etc.) information may be transmitted in the clear.

In lieu of using physically-distinct computing entities, computations herein may be carried out within a cluster comprises a set of computing entities (e.g., processors). A grid computing architecture may also be utilized.

There is no limitation on the type of computing entity that may implement any connection (e.g. client-to-server). Any computing entity (system, machine, device, program, process, utility, or the like) may act as a client or a server.

While given components of the system have been described separately, one of ordinary skill will appreciate that some of the functions may be combined or shared in given instructions, program sequences, code portions, and the like. Any application or functionality described herein may be implemented as native code, by providing hooks into another application, by facilitating use of the mechanism as a plug-in, by linking to the mechanism, and the like.

The functionality may be co-located or various parts/components may be separately and run as distinct functions, perhaps in one or more locations (over a distributed network).

There may any number of computing parties that securely compute the GWAS statistics using the secretly-shared data sets (namely, the genome and phenotype data, and the random number data created during the pre-processing operation).

The entity that performs pre-processing (CP0) may also be a computing entity (e.g., CP1) in the MPC computation to generate the GWAS output.

The pre-processing may be provided as a service.

The secure computation of the genome and phenotype data may be provided as a service.

Computing entities herein may be independent from one another, or associated with one another. Multiple computing entities may be associated with a single enterprise entity, but are separate and distinct from one another with respect to the MPC secure computation itself over their respective secret shares.

Having described our invention, what we claim also is set forth below:

1. A method for large-scale association studies of genomic and phenotypic data shared by study participants, comprising:
  at a first computing entity $CP_1$:
  (a) receiving an input value [x] that has been secret-shared by the study participants to each of the first computing entity $CP_1$ and a second computing entity $CP_2$ so as not to reveal to either computing entity the genomic and phenotype data of any study participant;
  (b) subtracting from the input value [x] a secret random value [r] that has been secret-shared by an auxiliary computing entity $CP_0$, the auxiliary computing entity $CP_0$ having generated randomly chosen blinding factors $[r_i], \ldots [r_n]$ of the secret random value [r];
  (c) publishing shares of [x−r] to reveal a blinded value x−r;
  (d) performing a computation over at least the published shares to generate a result;
  (e) receiving results of additional computations by the auxiliary computing entity $CP_0$ over the blinding factors, the results of the additional computations having been secret-shared by the auxiliary computing entity $CP_0$ and comprising uniformly random values;
  (f) using the result of the computation together with the results of the additional computations to generate a share;
  (g) receiving a corresponding share from the second computing entity $CP_2$, the corresponding share having been generated at the second computing entity $CP_2$ according to steps (a)-(f) with respect to information independently secret-shared to the second computing entity $CP_2$ by the study participants and the auxiliary computing entity $CP_0$; and (h) using the share and the corresponding share received from the second computing entity $CP_2$ to construct an output.

2. The method as described in claim 1 wherein the output comprises a set of genome-wide association study (GWAS) statistics.

3. The method as described in claim 2 further including identifying genetic variants that are statistically-correlated with a phenotype of interest using the GWAS statistics.

4. The method as described in claim 1 wherein the results of additional computations are computed by the auxiliary computing entity $CP_0$ in advance of steps (a) through (h) occurring at the first computing entity $CP_1$.

5. The method as described in claim 4 wherein the results of additional computations are Beaver multiplication triples of correlated random values.

6. The method as described in claim 1 wherein the auxiliary computing entity $CP_0$ is different from the first computing entity $CP_1$ and from the second computing entity $CP_2$.

7. The method as described in claim 1 wherein the first computing entity $CP_1$ cannot reconstruct the corresponding share received from the second computing entity $CP_2$, thereby preserving privacy of the genomic and phenotypic data.

8. The method as described in claim 1 wherein the first computing entity $CP_1$ and the second computing entity $CP_2$ are computing entities that differ from one another.

* * * * *